US012059429B2

(12) United States Patent
Kelly

(10) Patent No.: US 12,059,429 B2
(45) Date of Patent: Aug. 13, 2024

(54) HORNERIN: A NOVEL NON-VEGF MEDIATED ANGIOGENIC PROTEIN EXPRESSED IN BOTH HUMAN AND MOUSE ANGIOGENIC ENDOTHELIAL CELLS AND HUMAN PANCREATIC CANCER CELLS

(71) Applicant: University of Virginia Patent Foundation, Charlottesville, VA (US)

(72) Inventor: Kimberly A. Kelly, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 155 days.

(21) Appl. No.: 16/572,234

(22) Filed: Sep. 16, 2019

(65) Prior Publication Data
US 2020/0155594 A1    May 21, 2020

Related U.S. Application Data

(60) Provisional application No. 62/731,311, filed on Sep. 14, 2018.

(51) Int. Cl.
| | |
|---|---|
| *C12N 15/113* | (2010.01) |
| *A61K 31/7105* | (2006.01) |
| *A61K 38/00* | (2006.01) |
| *A61K 45/06* | (2006.01) |
| *A61P 35/00* | (2006.01) |
| *C07K 7/06* | (2006.01) |
| *C07K 16/28* | (2006.01) |
| *C07K 16/30* | (2006.01) |

(52) U.S. Cl.
CPC .......... *A61K 31/7105* (2013.01); *A61P 35/00* (2018.01); *C07K 7/06* (2013.01); *C07K 16/2863* (2013.01); *C07K 16/30* (2013.01); *C12N 15/113* (2013.01); *A61K 38/00* (2013.01); *A61K 45/06* (2013.01)

(58) Field of Classification Search
CPC ... A61K 31/7105; A61K 31/713; A61P 35/00; C12N 15/113; C12N 2310/14
See application file for complete search history.

(56) References Cited

U.S. PATENT DOCUMENTS

2018/0360755 A1   12/2018   Klibanov

OTHER PUBLICATIONS

Craven et al (Cancer Letters 381 (2016) 201-210) (Year: 2016).*
Morton et al (Cancer Res; 76(21) Nov. 1, 2016) (Year: 2016).*
Seaman (Ph.D. Dissertation, University of Virginia, published online in the Libra ETD Repository, uploaded Apr. 29, 2014, retrieved from https://search.lib.virginia.edu/sources/uva_library/items/f7623c85x) (Year: 2014).*
Gutknecht et al (Nature Comm. 8:552, 14 pages, 2017) (Year: 2017).*
Seaman et al (In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr 3891) (Year: 2013).*
Seaman Dissertation "Item Details", retrieved from https://search.lib.virginia.edu/sources/uva_library/items/f7623c85x) (Year: 2014).*
Nakamura et al (Cancer Res 2006; 66: (18). Sep. 15, 2006) (Year: 2006).*
Tanaka et al (BMC Cancer (2015) 15:53, 14 pages) (Year: 2015).*
Chen et al (Oncology Reports 29: 260-268, 2013) (Year: 2013).*
Hauschild et al. Predictive value of serum S100B for monitoring patients with metastatic melanoma during chemotherapy and/or immunotherapy. Br. J. Dermatol. 140, 1065-1071 (1999).
Casanovas et al. Drug resistance by evasion of antiangiogenic targeting of VEGF signaling in late-stage pancreatic islet tumors. Cancer Cell 8, 299-309 (2005).
Fleming et al. Hornerin, an S100 family protein, is functional in breast cells and aberrantly expressed in breast cancer. BMC Cancer 12, 266 (2012).
Gupta et al. Differential expression of S100A2 and S100A4 during progression of human prostate adenocarcinoma. J. Clin. Oncol. 21, 106-112 (2003).
Henry et al. Hornerin is a component of the epidermal cornified cell envelopes. FASEB J. 25, 1567-1576 (2011).
Makino et al. Hornerin, a novel profilaggrin-like protein and differentiation-specific marker isolated from mouse skin. J. Biol. Chem. 276, 47445-47452 (2001).
Makino et al. J. Histochem. Cytochem. 51, 485-492 (2003).
Rachow et al. Occludin Is Involved in Adhesion, Apoptosis, Differentiation and Ca2+-Homeostasis of Human Keratinocytes: Implications for Tumorigenesis. PLoS One 8, e55116 (2013).
Takaishi et al. BMC Cancer (2015) 15:53, 14 pages.
Wu et al. Highly complex peptide aggregates of the S100 fused-type protein hornerin are present in human skin. J. Invest. Dermatol. 129, 1446-1458 (2009).

* cited by examiner

*Primary Examiner* — Richard A Schnizer
(74) *Attorney, Agent, or Firm* — Jenkins, Taylor & Hunt, P.A.

(57) ABSTRACT

Provided are compositions and methods for use of hornerin-binding molecules, including peptides and antibodies. In some embodiments, the presently disclosed subject matter provides compositions that include horning-binding molecules, including but not limited to peptides, uses for the disclosed compositions, including in methods for treating tumors, methods for increasing the survival of subject with tumor, methods for suppressing tumor growth in subjects, methods for reducing tumor vascularity in subjects, methods for treating diseases, disorders, and/or conditions associated with undesirable hornerin expression; methods for modulating hornerin biological activities, methods for imaging cells, tissues, and/or organs that expresses hornerin, and methods for delivering active agents to cells, tissues, and/or organ that expresses hornerin.

12 Claims, 31 Drawing Sheets
(17 of 31 Drawing Sheet(s) Filed in Color)
Specification includes a Sequence Listing.

| | | | | | | |
|---|---|---|---|---|---|---|
| ☑ | ✓ | (R)SSSRGPYESGSGHSSGLGHQE | 100% | 3.91 | 0.56 | 2 |
| ☑ | ✓ | (R)YGQQGSGSGQSPSP(G) | 100% | 2.91 | 0.65 | 2 |
| ☑ | ✓ | (R)GSGSGQSPSYGR(H) | 100% | 2.51 | 0.50 | 2 |
| ☑ | ✓ | (R)GSGSGQSPSYGR(H) | 100% | 2.62 | 0.47 | 2 |
| ☑ | ✓ | (R)GSGSGQSPSYGR(H) | 100% | 2.32 | 0.47 | 2 |
| ☑ | ✓ | (R)HGSGSGQSSGFGHK(S) | 100% | 3.09 | 0.68 | 2 |
| ☑ | ✓ | (R)HGSGSGQSSGFGHK(S) | 100% | 2.98 | 0.57 | 2 |
| ☑ | ✓ | (Q)HGSSSGSSSSYGQHGSGSR(Q) | 100% | 3.63 | 0.70 | 1 |
| ☑ | ✓ | (Q)HGSSSGSSSSYGQHGSGSR(Q) | 100% | 3.60 | 0.68 | 1 |
| ☑ | ✓ | (Q)HGSSSGSSSSYGQHGSGSR(Q) | 100% | 3.18 | 0.69 | 1 |
| ☑ | ✓ | (R)HGSGSGHSSSYGQHGSGSGW | 100% | 3.56 | 0.79 | 2 |

```
MPKLLQGVIT VIDVFYQYAT QHGEYDTLNK AELKELLENE FHQILKNPND PDTVDIILQS LDRDHNKKVD PTEYLLMIFK LVQARNKIIG KDYCQVSGSK
LRDDTHQHQE EQEETEKEEN KRQESSFSHS SWSAGENDSY SRNVRGSLKP GTESISRRLS FQRDFSGQHN SYSGQSSSYG EQNSDHQSS GRGQCGSGSG
QSPNYGQHGS GSGQSSSNDT HGSGSGQSSG FSQHKSSSGQ SSGYSQHGSG SGHSSGYGQH GSRSGQSSRE ERHSSSGSS SSYGQHGSGS RQSLGHGRQG
SGSRQSPSHV RHGSGSGHSS SHGQHGSGGS YSYSRGHYES GSGQTSGFGQ HESGSGQSSG YSKHGSGSGH SSSQGHGST SGQASSSGQH GSSSRQSSSY
GQHESASRHS SGRGQHSSGS GQSPGHGQRG SGSGQSPSSG QHGTGFGRSS SSGPYVSGSG YSSGFGHHES SSEHSSGYTQ HGSGSGHSSG HGQHGSRSGQ
SSRGERQGSS AGSSSSSYGQH GSGSRQSLGH SRHGSGSGQS PSPSRGRHES GSRQSSSYGP HGYGSGRSSS RGPYESGSGH SSGLGHQESR SGQSSSYGQH
GSSSSGHSSTH GQHGSTSGQS SSCGQHGATS GQSSSHGQHG SCSSSQSSRYG QQGSGSGQSP SRGRHGSDFC HSSSYGQHGS GSGWSSSNGP HGSVSGQSSG
PGHKSGSGQS SGYSQHGSGS SHSSGYRKHG SRSGQSSRSE QHGSSSGLSS SYGQHGSGSH QSSGHGRQGS GSGHSPSRVR HGSSSGHSSS HGQHGSGTSC
SSSCGHYESG SGQASGFGQH ESGSGQGYSQ HGSASGHFSS QGRHGSTSGQ SSSSGQHDSS SGQSSSYGQH ESASHHASGR GRHGSGSGQS PGHGQRGSGS
GQSPSYGRHG SGSGRSSSSG RHGSGSGQSS GFGHKSSSGQ SSGYTQHGSG SGHSSSYEQH GSRSGQSSRS EQHGSSSGSS SSYGQHGSGS RQSLGHGQHG
SGSGQSPSPS RGRHGSGSGQ SSSYGPYRSG SGWSSSRGPV ESGSGHSSGL GHRESRSGQS SGYGQHGSSS GHSSTHGQHG STSGQSSSCG QHGASSGQSS
SHGQHGSGSS QSSGYGRQGS GSGQSPGHGQ RGSGSRQSPS YGRHGSGSGR SSSSGQHGSG LGESSGFGHH ESSSGQSSSY SQHGSGSHS SGYGQHGSRS
GQSSRGERHG SSSGSSSHYG QHGSGSRQSS GHGRQGSGSG HSPSRGRHGS GLGHSSSHGQ HGSGSGRSSS RGPYESRSGH SSVFGQHESG SGHSSAYSQH
GSGSGHFCSQ GQHGSTSGQS STFDQEGSST GQSSSYGHRG SGSSQSSGYG RHGAGSGQSP SRGRHGSGSG HSSSYGQHGS GSGWSSSSSGR HGSGSGQSSG
FGHHESSSWQ SSGCTQHGSG SGHSSSYEQH GSRSGQSSRG ERHGSSSGSS SSYGQHGSGS RQSLGHGQHG SGSGQSPSPS RGRHGSGSGQ SSSYSPYGSG
SGWSSSRGPY ESGSSHSSGL GHRESRSGQS SGYGQHGSSS GHSSTHGQHG STSGQSSSCG QHGASSGQSS SHGQHGSGSS QSSGYGRQGS GSGQSPGHGQ
RGSGSRQSPS YGRHGSGSGR SSSSGQHGSG LGESSGFGHH ESSSGQSSSY SQHGSGSHS SGYGQHGSRS GQSSRGERHG SSSRSSSRYG QHGSGSRQSS
GHGRQGSGSG QSPSRGRHGS GLGHSSSHGQ HGSGSGRSSS RGPYESRSGH SSVFGQHESG SGHSSAYSQH GSGSGHFCSQ GQHGSTSGQS STFDQEGSST
GQSSSHGQHG SGSSQSSSYG QQGSGSGQSP SRGRHGSGSG HSSSYGQHGS GSGWSSSSGR HGSGSGQSSG FGHHESSSWQ SSGYTQHGSG SGHSSSYEQH
GSRSGQSSRG EQHGSSSGSS SSYGQHGSGS RQSLGHGQHG SGSGQSPSPS RGRHGSGSGQ SSSYGPYGSG SGWSSSRGPY ESGSGHSSGL GHRESRSGQS
SGYGQHGSSS GHSSTHGQHG SASGQSSSCG QHGASSGQSS SHGQHGSGSS QSSGYGRQGS GSGQSPGHGQ RGSGSRQSPS YGRHGSGSGR SSSSGQHGPG
LGESSGFGHH ESSSGQSSSY SQHGSGSHS SGYGQHGSRS GQSSRGERHG SSSGSSSRYG QHGSGSRQSS GHGRQGSGSG HSPSRGRHGS SGHSSSHGQ
HGSGSGRSSS RGPYESRSGH SSVFGQHESG SGHSSAYSQH GSGSGHFCSQ GQHGSTSGQS STFDQEGSST GQSSSYGHRG SGSSQSSSYG QQGSGSGQSP
SRGRHGSGSG HSSSYGQHGS GSGWSSSGR HGSGSGQSSG FGHHESSSWQ SSGYTQHGSG SGHSSSYEQH GSRSGQSSRG ERHGSSSGSS SSYGQHGSGS
RQSLGHGQHG SGSGQSPSPS RGRHGSGSGQ SSSYSPYGSG SGWSSSRGPY ESGSGHSSGL GHRESRSGQS SGYGQHGSSS GHSSTHGQHG STSGQSSSCG
QHGASSGQSS SHGQHGSGSS QSSGYGRQGS GSGQSPGHGQ RGSGSRQSPS YGRHGSGSGR SSSSGQHGSG LGESSGFGHH ESSSGQSSSY SQHGSGSHS
SGYGQHGSRS GQSSRGERHG SSSGSSSHYG QHGSGSRQSS GHGRQGSGSG QSPSRGRHGS GLGHSSSHGQ HGSGSGRSSS RGPYESRLGH SSVFGQHESG
SGHSSAYSQH GSGSGHFCSQ GQHGSTSGQS STFDQEGSST GQSSSYGHRG SGSSQSSGYG RHGAGSGQSL SHGRHGSGSG QSSSYGQHGS GSGQSSGYSQ
HGSGSGQDGY SYCKGGSNHD GGSSGSYFLS FPSSTSPYEY VQEQRCYFYQ
```

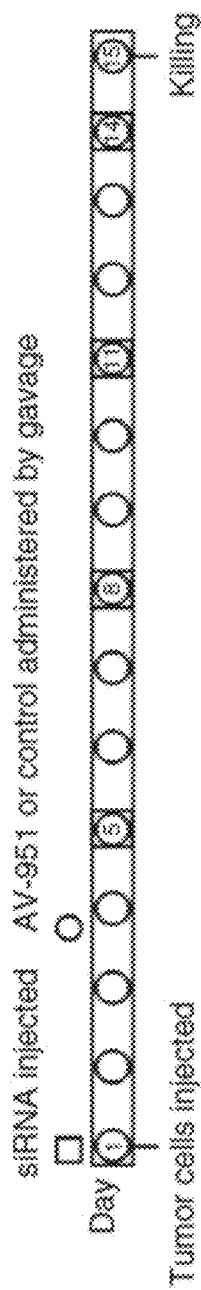
*FIG. 14A*
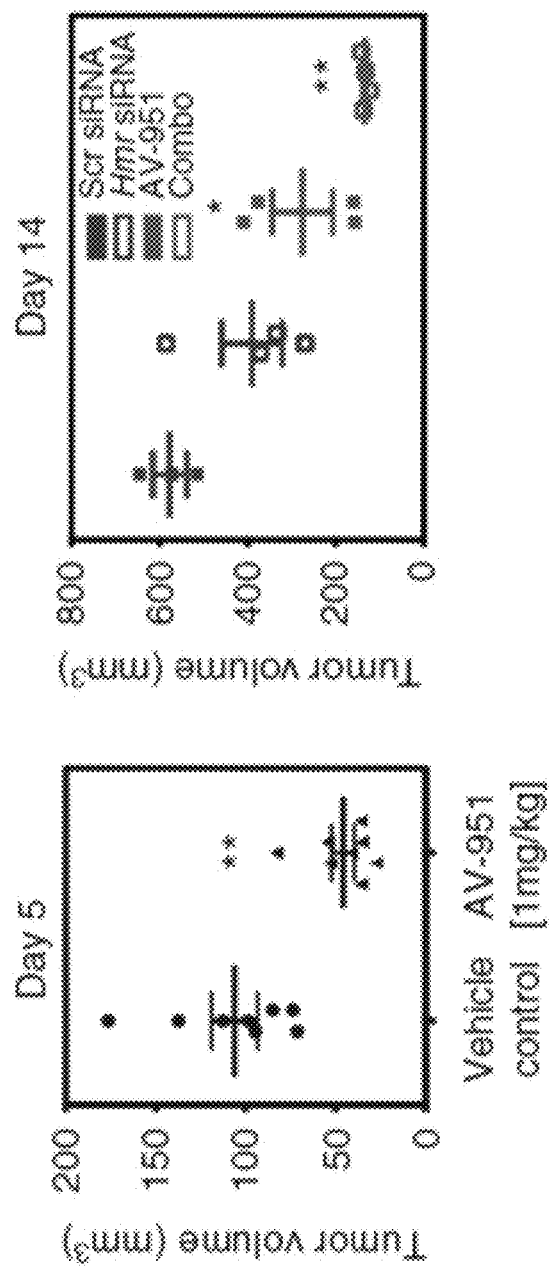
*FIG. 14C*
*FIG. 14B*

```
                         SEQUENCE LISTING

<160> NUMBER OF SEQ ID NOS: 56

<210> SEQ ID NO 1
<211> LENGTH: 7
<212> TYPE: PRT
<213> ORGANISM: Homo sapiens

<400> SEQUENCE: 1

Glu Asp Arg Ala Asn Arg Gln
1               5

<210> SEQ ID NO 2
<211> LENGTH: 7
<212> TYPE: PRT
<213> ORGANISM: Homo sapiens

<400> SEQUENCE: 2

Ser Ala Pro Ser Ser Lys Asn
1               5

<210> SEQ ID NO 3
<211> LENGTH: 7
<212> TYPE: PRT
<213> ORGANISM: Homo sapiens

<400> SEQUENCE: 3

Thr Ser Leu Ser Met Pro Ser
1               5

<210> SEQ ID NO 4
<211> LENGTH: 7
<212> TYPE: PRT
<213> ORGANISM: Homo sapiens

<400> SEQUENCE: 4

Leu Pro Thr Pro Pro Tyr Ala
1               5

<210> SEQ ID NO 5
<211> LENGTH: 7
<212> TYPE: PRT
<213> ORGANISM: Homo sapiens

<400> SEQUENCE: 5

Met Thr Ser Gln His Pro Lys
1               5
```

```
<210> SEQ ID NO 6
<211> LENGTH: 7
<212> TYPE: PRT
<213> ORGANISM: Homo sapiens

<400> SEQUENCE: 6

Asn Gln Leu Pro Leu His Ala
1               5

<210> SEQ ID NO 7
<211> LENGTH: 7
<212> TYPE: PRT
<213> ORGANISM: Homo sapiens

<400> SEQUENCE: 7

Thr Thr Val Met Gly Asn Leu
1               5

<210> SEQ ID NO 8
<211> LENGTH: 7
<212> TYPE: PRT
<213> ORGANISM: Homo sapiens

<400> SEQUENCE: 8

Ala Met Leu Pro Tyr Thr Phe
1               5

<210> SEQ ID NO 9
<211> LENGTH: 7
<212> TYPE: PRT
<213> ORGANISM: Homo sapiens

<400> SEQUENCE: 9

Ser Leu Leu Asn Arg Met Pro
1               5

<210> SEQ ID NO 10
<211> LENGTH: 7
<212> TYPE: PRT
<213> ORGANISM: Homo sapiens

<400> SEQUENCE: 10

Gly Lys Pro Met Pro Pro Met
1               5

<210> SEQ ID NO 11
<211> LENGTH: 7
<212> TYPE: PRT
<213> ORGANISM: Homo sapiens

<400> SEQUENCE: 11

Val Ala His Gln Leu Ser Arg
1               5

<210> SEQ ID NO 12
<211> LENGTH: 7
<212> TYPE: PRT
<213> ORGANISM: Homo sapiens

<400> SEQUENCE: 12

His Ala Ile Tyr Pro Arg His
1               5
```

```
<210> SEQ ID NO 13
<211> LENGTH: 7
<212> TYPE: PRT
<213> ORGANISM: Homo sapiens

<400> SEQUENCE: 13

Ile Pro Thr Leu Pro Ser Ser
1               5

<210> SEQ ID NO 14
<211> LENGTH: 7
<212> TYPE: PRT
<213> ORGANISM: Homo sapiens

<400> SEQUENCE: 14

Glu Pro Leu Gln Leu Lys Met
1               5

<210> SEQ ID NO 15
<211> LENGTH: 7
<212> TYPE: PRT
<213> ORGANISM: Homo sapiens

<400> SEQUENCE: 15

Ser His Gly Asn Trp Trp Arg
1               5

<210> SEQ ID NO 16
<211> LENGTH: 7
<212> TYPE: PRT
<213> ORGANISM: Homo sapiens

<400> SEQUENCE: 16

Leu His Arg Pro Tyr Ser Thr
1               5

<210> SEQ ID NO 17
<211> LENGTH: 7
<212> TYPE: PRT
<213> ORGANISM: Homo sapiens

<400> SEQUENCE: 17

His Ala Ile Tyr Pro Arg His
1               5

<210> SEQ ID NO 18
<211> LENGTH: 7
<212> TYPE: PRT
<213> ORGANISM: Homo sapiens

<400> SEQUENCE: 18

Gln Ile Leu Ala Phe Asn Ser
1               5

<210> SEQ ID NO 19
<211> LENGTH: 7
<212> TYPE: PRT
<213> ORGANISM: Homo sapiens

<400> SEQUENCE: 19

Ser Ala Pro Ser Ser Lys Asn
1               5

<210> SEQ ID NO 20
<211> LENGTH: 7
```

```
<212> TYPE: PRT
<213> ORGANISM: Homo sapiens

<400> SEQUENCE: 20

Thr Leu His Ser Leu Pro Pro
1               5

<210> SEQ ID NO 21
<211> LENGTH: 7
<212> TYPE: PRT
<213> ORGANISM: Homo sapiens

<400> SEQUENCE: 21

Trp Thr Ile Thr Lys His Pro
1               5

<210> SEQ ID NO 22
<211> LENGTH: 7
<212> TYPE: PRT
<213> ORGANISM: Homo sapiens

<400> SEQUENCE: 22

Ser Pro Thr Gln Pro Lys Ser
1               5

<210> SEQ ID NO 23
<211> LENGTH: 7
<212> TYPE: PRT
<213> ORGANISM: Homo sapiens

<400> SEQUENCE: 23

Gly Lys Val Gln Ala Gln Ser
1               5

<210> SEQ ID NO 24
<211> LENGTH: 7
<212> TYPE: PRT
<213> ORGANISM: Homo sapiens

<400> SEQUENCE: 24

Gly Arg Pro His Ser Ala Leu
1               5

<210> SEQ ID NO 25
<211> LENGTH: 7
<212> TYPE: PRT
<213> ORGANISM: Homo sapiens

<400> SEQUENCE: 25

Ala Thr Leu Thr His Pro Pro
1               5

<210> SEQ ID NO 26
<211> LENGTH: 7
<212> TYPE: PRT
<213> ORGANISM: Homo sapiens

<400> SEQUENCE: 26

Ser Thr Pro Ile Gln Gln Pro
1               5

<210> SEQ ID NO 27
<211> LENGTH: 7
<212> TYPE: PRT
<213> ORGANISM: Homo sapiens
```

<400> SEQUENCE: 27

Ser Leu Tyr Lys Trp Thr Ile
1               5

<210> SEQ ID NO 28
<211> LENGTH: 7
<212> TYPE: PRT
<213> ORGANISM: Homo sapiens

<400> SEQUENCE: 28

Ala Asn Thr Thr Pro Arg His
1               5

<210> SEQ ID NO 29
<211> LENGTH: 7
<212> TYPE: PRT
<213> ORGANISM: Homo sapiens

<400> SEQUENCE: 29

His Thr Ala Pro Asn Phe Ala
1               5

<210> SEQ ID NO 30
<211> LENGTH: 7
<212> TYPE: PRT
<213> ORGANISM: Homo sapiens

<400> SEQUENCE: 30

Ala Asn Ser Thr Pro Pro Ile
1               5

<210> SEQ ID NO 31
<211> LENGTH: 21
<212> TYPE: DNA
<213> ORGANISM: Homo sapiens

<400> SEQUENCE: 31
cctttagtgg tacctttcta t                                         21

<210> SEQ ID NO 32
<211> LENGTH: 21
<212> TYPE: DNA
<213> ORGANISM: Homo sapiens

<400> SEQUENCE: 32
gccctcatag ttagcgtaac g                                         21

<210> SEQ ID NO 33
<211> LENGTH: 9632
<212> TYPE: DNA
<213> ORGANISM: Homo sapiens

<400> SEQUENCE: 33
agcaccctga aagctgtttc tgtctctacc ctacttgttc ctctggtgag ctaggttact    60
caaacttgca aaaaaaaaa tgcctaaact cctacaaggc gtcatcactg tcatcgatgt   120
tttctaccaa tatgccaccc agcatgggga gtatgatacg ttgaacaagg cagagctgaa   180
agaacttctg gaaaatgagt ttcatcaaat tctgaagaat ccaaacgatc cagatactgt   240
ggatatcatc ttgcaaagtc tggatcgaga ccataacaag aaagtggatt ttactgagta   300
tcttctgatg atattcaagc tggttcaggc tcgtaataaa atcattggca aagattactg   360

-continued

```
ccaagtttca gggtcaaagc tgagagatga cactcaccag caccaagagg aacaagaaga    420
aactgaaaaa gaggagaaca aacggcaaga atcctctttt agtcattcaa gttggagtgc    480
aggagagaat gattcctatt ccagaaacgt cagaggaagt cttaaacctg ggactgaatc    540
catatccaga agactgagtt ttcaaagaga cttttctggc aacataact cctactcagg     600 tcagtcttcc agctatggtg agcaaaactc cgactcccat cagtcttcag gccgcggcca    660
atgtgggtct gggtcagggc agtctcccaa ctatggccaa cacggctctg gctccggaca    720
gtcttccagc aatgacacac atgggtctgg ctcaggccag tcttctggct ttagtcaaca    780
caagtctagc tcagggcagt cctctggtta cagtcagcat ggatctggct caggtcactc    840
ctctggctac ggacaacacg gctctaggtc aggacagtca tctaggggtg aacgacacag    900
atctagctca ggttcgtctt ccagctatgg tcagcatggg tctggttccc gtcagtcttt    960
gggccacggc cgacaagggt ctggatctcg ccagtctcct agccacgtcc gacatgggtc   1020
cggttcgggg cactcctcca gccacggcca cacgggtct ggctcaagtt actcttacag    1080
ccgtggccat tatgagtctg gctcaggcca gacttctggc tttgggcaac atgagtctgg   1140
ctcaggacag tcctctggct atagtaagca tggttctggc tcaggtcact cctctagcca   1200
gggacaacat ggatctacgt cagggcaggc atcaagctct ggccaacatg gctccagctc   1260
acgtcagtct tccagctatg gtcagcatga gtctgcctcc cgtcactctt caggccgcgg   1320
ccaacacagc tctggatctg ccagtctcc aggccacggc cagcgtgggt ctgggtcagg    1380
gcagtctccc agctccggcc aacatgggac tggctttggt cgatcttcca gcagtggccc   1440
atatgtgtct ggttcaggct actcttctgg ctttggtcac cacgagtcta gctcagagca   1500
ttcctctggt tacactcagc atggatctgg ctcaggtcac tcctccggcc acggacaaca   1560
cggctctagg tcaggacagt catctagggg tgaacgacaa ggatctagtg caggttcatc   1620
ttccagctat ggtcagcatg gtctggctc cgtcaatct ttgggacaca gccgacatgg    1680
gtctggatct ggccagtctc ctagccctag ccgtggccga catgagtctg ttccaggca    1740 gtcttccagc tatggcccac atgggtatgg ctcagggagg tcttcaagcc gtggcccata   1800
tgagtctggc tccggtcact cttctggctt aggtcaccaa gagtctcgct caggacagtc   1860
ctctggctac ggtcaacacg gatctagctc gggtcattcc tctacccatg gcaacatgg    1920 ttctacatca ggacagtcat cgagctgtgg ccaacatgga gctacctcag gtcagtcttc   1980
cagccacggt cagcatggct ctggctcaag tcagtcttct cgctatggcc aacagggctc   2040
tggatctggc cagtctccta gtcgcggccg acatgggtcc gattttgggc actcttccag   2100
ctacggccaa catgggtctg ctccggttg gtcttcaagc aatggccac atgggtctgt     2160 ctcaggccag tcttccggct ttggtcacaa gtctggctca gggcagtcct ctggttacag   2220
tcagcatgga tctggctcaa gtcactcctc cggctacaga aaacacggct ctaggtcagg   2280
acagtcatct aggagtgaac aacacggatc tagctcaggt ttgtcttcca gctatggtca   2340
gcatgggtcg ggctcccatc aatcttcggg ccacggccga caagggtctg gatctggcca   2400
ctctcctagc cgtgtccgac atgggtccag ttcagggcac tcctccagcc acggccaaca   2460
cgggtctggc acaagttgtt cttccagctg tggccattat gagtctggct caggccaggc   2520
ttctggtttt gggcaacacg agtctggctc aggacagggc tatagtcagc atggttctgc   2580
ctcaggtcac ttctctagcc agggacgaca tggatctacg tcaggcagt catcaagctc    2640 cggccaacat gactctagct caggtcaatc ttccagctat ggtcagcatg agtctgcctc   2700
ccatcacgct tcgggccgcg gccgacatgg ctctggatct ggccagtctc caggccacgg   2760
```

```
ccagcgtggg tctgggtcag ggcagtctcc cagctatggc cgacatgggt ctggctccgg    2820
tcggtcttcc agcagtggcc gacatgggtc tggctcaggc cagtcttctg gctttggtca    2880
caagtctagc tcagggcagt cctctggtta cactcagcat ggatctggct caggtcactc    2940
ctccagctac gaacaacacg gctctaggtc aggacagtca tctaggagcg aacaacatgg    3000
atctagctca ggttcgtctt ccagctatgg tcagcatggg tctggctccc gtcagtcttt    3060
gggccacggc caacatgggt ctggatctgg ccagtctcct agccctagcc gtggccgaca    3120
tgggtctggt tccgggcagt cttccagcta tgcccatat aggtctggct cagggtggtc    3180
ttcaagccgt ggcccatatg agtctggctc cggtcactct tctggcttag gtcaccgaga    3240
gtctcgctca ggacagtcct ctggctacgg tcaacatgga tctagctcag gtcattcctc    3300
tacccatggg caaacggtt ctacatcagg acagtcatcg agctgtggcc aacatggagc    3360
tagctcaggt cagtcttcca gccacggtca gcatggctct ggctcaagtc agtcttctgg    3420
ctatggccga cagggctctg gatctggcca gtctccaggc cacggccagc gtgggtctgg    3480
gtcaaggcag tctcccagct acggccgaca tgggtctggc tccggtcggt cttccagcag    3540
tggccaacat gggtctggct taggcgagtc ttctggcttt ggtcaccacg agtctagctc    3600
agggcagtcc tctagttaca gtcagcatgg gtctggctca ggtcactcct ctggctacgg    3660 acaaacggc tctagatcag gacagtcatc taggggtgaa cgacacggat ctagctcagg    3720
ttcgtcttcc cactatggtc agcatgggtc tggctcccgt cagtcttcgg ccacggccg    3780 acaagggtct ggatctggcc attccctag ccgcggccga catgggtccg gtttggggca    3840
ctcctccagc cacggccaac atgggtctgg ctcaggtcgt tcttccagcc gtggcccata    3900
tgagtctcgc tcgggtcact cttctgtctt tggtcaacat gagtctggct caggacattc    3960
ctctgcttac agtcagcatg gtagtggctc agggcacttc tgtagccaag gacagcatgg    4020
ttctacatca ggacagtcat caacctttga ccaggaggga tctagcacag gccagtcttc    4080
cagctatggc caccgtggct ctggctccag tcagtcttct ggctatggcc gacatggggc    4140
tggatctggc cagtctccta gtcgcggccg acatgggtcc ggttctgggc actcttccag    4200
ctacggccaa catgggtctg ctccggttg gtcttccagc agtggccgac atgggtctgg    4260
ctcaggtcag tcttctggat ttggtcacca cgagtctagc tcatggcagt cctctggttg    4320
cactcagcat ggatctggct caggtcactc ctccagctac gaacaacacg gctctaggtc    4380
aggacagtca tctaggggtg aacgacacgg atctagctca ggttcatctt ccagctatgg    4440
tcagcatggg tctggctccc gtcagtcttt gggccacggc caacatgggt ctggatctgg    4500
ccagtctcct agccctagcc gtggccgaca tgggtctggt tctgggcagt cttccagcta    4560
cagcccatat gggtctggct cagggtggtc ttccagccgt ggcccatatg agtctggctc    4620
cagtcactct tctggcttag gtcaccgaga gtctcgctca ggacagtcct ctggctacgg    4680
tcaacatgga tctagctcag gtcattcctc tacccatggg caaacatggtt ctacatcagg    4740 acagtcatcg agctgtggcc aacatggagc tagctcaggt cagtcttcca gccacggtca    4800
gcatggctct ggctcaagtc agtcttctgg ctatggccga cagggctctg gatctggcca    4860
gtctccaggc cacggccagc gtgggtctgg gtcaaggcag tctcccagct acggccgaca    4920
tgggtctggc tccggtcggt cttccagcag tggccaacat gggtctggct taggcgagtc    4980
ttctggcttt ggtcaccacg agtctagctc agggcagtcc tctagttaca gtcagcatgg    5040
gtctggctca ggtcactcct ctggctacgg acaaacggc tctagatcag gacagtcatc    5100
```

```
tagggggtgaa cgacacggat ctagctcacg ttcgtcttcc cgctatggtc agcatgggtc   5160
tggctcccgt cagtcttcgg gccacggccg acaagggtct ggatctggcc agtcccctag   5220
ccgcggccga catgggtccg gtttggggca ctcctccagc cacggccaac atgggtctgg   5280
ctcaggtcgt tcttccagcc gtggcccata tgagtctcgc tcgggtcact cttctgtctt   5340
tggtcaacat gagtctggct caggacattc ctctgcttac agtcagcatg gtagtggctc   5400
agggcacttc tgtagccaag gacagcatgg ttctacatca ggacagtcat caacctttga   5460
ccaggaggga tctagcacag gtcagtcttc agccacggt cagcatggct ctggctcaag   5520
tcagtcttct agctatggcc aacagggctc tggatctggc cagtctccta gtcgcggccg   5580
acatgggtcc ggttccgggc actcttccag ctacggccaa catgggtctg ctccggttg   5640
gtcttccagc agtggccgac atgggtctgg ctcaggtcag tcttctggat ttggtcacca   5700
tgagtctagc tcatggcagt cctctggtta cactcagcat ggatctggct caggtcactc   5760
ctccagctac gaacaacacg gctctaggtc aggacagtca tctagggtg aacaacacgg   5820
atctagctca ggttcatctt ccagctatgg tcagcatggg tctggctccc gtcagtcttt   5880
gggccacggc caacatgggt ctggatctgc ccagtctcct agccctagcc gtggccgaca   5940
tgggtctggt tctgggcagt cttccagcta cggcccatat gggtctggct cagggtggtc   6000
ttccagccgt ggcccatatg agtctggctc cggtcactct tctggcttag gtcaccgaga   6060
gtctcgctca ggacagtcct ctggctacgg tcaacatgga tctagctcag gtcattcctc   6120
tacccatggg caacatggtt ctgcatcagg acagtcatcg agctgtggcc aacatggagc   6180
tagctcaggt cagtcttcca gccacggtca gcatggctct ggctcaagtc agtcttctgg   6240
ctatggccga cagggctctg gatctggcca gtctccaggc cacggccagc gtgggtctgg   6300
gtcaaggcag tctcccagct atggccgaca tgggtctggc tccggtcggt cttccagcag   6360
tggccaacat gggcctggct taggcgagtc ttctggcttt ggtcaccacg agtctagctc   6420
agggcagtcc tctagttaca gtcagcatgg gtctggctca ggtcactcct ctggctacgg   6480
acaacacggc tctagatcag gacagtcatc tagggggtgaa cgacacggat ctagctcagg   6540
ttcgtcttcc cgctatggtc agcatgggtc tggctcccgt cagtcttcgg gccacggccg   6600
acaagggtct ggatctggcc attcccctag ccgcggccga catgggtccg gttcggggca   6660
ctcctccagc cacggccaac atgggtctgg ctcaggtcgt tcttccagcc gtggcccata   6720
tgagtctcgc tcgggtcact cttctgtctt tggtcaacat gagtctggct caggacattc   6780
ctctgcttac agtcagcatg gtagtggctc agggcacttc tgtagccaag gacagcatgg   6840
ttctacatca ggacagtcat caacctttga ccaggaggga tctagcacag gtcagtcttc   6900
cagccacggt cagcatggct ctggctcaag tcagtcttct agctatggcc aacagggctc   6960
tggatctggc cagtctccta gtcgcggccg acatgggtcc ggttccgggc actcttccag   7020
ctacggccaa catgggtctg ctccggttg gtcttccagc agtggccgac atgggtctgg   7080
ctcaggtcag tcttctggat ttggtcacca cgagtctagc tcatggcagt cctctggtta   7140
cactcagcat ggatctggct caggtcactc ctccagctac gaacaacacg gctctaggtc   7200
aggacagtca tctagggtg aacgacacgg atctagctca ggttcatctt ccagctatgg   7260
tcagcatggg tctggctccc gtcagtcttt gggccacggc caacatgggt ctggatctgg   7320
ccagtctcct agccctagcc gtggccgaca tgggtctggt tctgggcagt cttccagcta   7380
cagcccatat gggtctggct cagggtggtc ttccagccgt ggcccatatg agtctggctc   7440
cggtcactct tctggcttag gtcaccgaga gtctcgctca ggacagtcct ctggctacgg   7500
```

```
tcaacatgga tctagctcag gtcattcctc tacccatggg caacatggtt ctacatcagg    7560
acagtcatcg agctgtggcc aacatggagc tagctcaggt cagtcttcca gccacggtca    7620
gcatggctct ggctcaagtc agtcttctgg ctatggccga cagggctctg gatctggcca    7680
gtctccaggc cacggccagc gtgggtctgg gtcaaggcag tctcccagct acggccgaca    7740
tgggtctggc tccggtcggt cttccagcag tggccaacat gggtctggct taggcgagtc    7800
ttctggcttt ggtcaccacg agtctagctc agggcagtcc tctagttaca gtcagcatgg    7860
gtctggctca ggtcactcct ctggctacgg acaacacggc tctagatcag gacagtcatc    7920 tagggggtgaa cgacacggat ctagctcagg ttcgtcttcc cactatggtc agcatgggtc    7980
tggctcccgt cagtcttcgg gccacggccg acaagggtct ggatctggcc agtcccctag    8040
ccgcggccga catgggtccg gtttggggca ctcctccagc cacggccaac atgggtctgg    8100
ctcaggtcgt tcttccagcc gtggcccata tgagtctcgc ttgggtcact cttctgtctt    8160
tggtcaacat gagtctggct caggacattc tctgcttac agtcagcatg gtagtggctc    8220
agggcacttc tgtagccaag acagcatgg ttctacatca ggacagtcat caacctttga    8280
ccaggaggga tctagcacag gccagtcttc cagctatggc caccgtggct ctggctccag    8340
tcagtcttct ggctatggcc gacatggggc tggatctggc cagtctctta gccacggccg    8400
acacgggtct ggttcaggc agtcttccag ctacggccaa catgggtctg gctcaggaca    8460
gtcctctggt tatagtcagc atggaagtgg ctcagggcaa gatgggtatt cttattgcaa    8520
aggaggaagt aaccatgatg ggggaagttc tggctcatat tttctcagtt ttcctagtag    8580
cacttcaccc tatgaatatg tccaagagca gaggtgctac ttttatcagt gaataataaa    8640
cataaatgca atttactcaa gtagcaattt aagaaatagg aaagtcatct atgaattcat    8700
catgaaagac aagcaatcca tcatgaaatt cgttctaaaa gtgaatcaat gcatttctgt    8760
ctctttcttt agagcctaaa actgtagcat atatcttgtt atggggttcc ttccaaagac    8820
tgttaggcat ttgtgctact tgttagaaaa atactgagtg gaataacttg ttagaatgag    8880
ggttaaactt tgaggaataa tgaaaagctt ttaaagagct ttgggtttag ttggagttgt    8940 cttttttgaga gctcatcatt catttataga tggtgccaaa gctaacctta catttcttag    9000
aagcaaaata ttacaaatgc attaccagtc ctagatacaa agctttgttt tacagcaatt    9060
agtgtaccct aattttttagt gtgccccaag tttggtgtgt cccaattttt ggtattgtgg    9120
cagaaggtga aggctctgaa agcaaagatg cagcagcggt agtgtcttta cttatcaaaa    9180
ccatcaagtc ctttttcttg ggtatatatt taatcagtaa gttaattagt ggcataaaaa    9240
agtagcatca gggtcttttc ccaagccagt gagcaagagc attatttcat aaagaatagg    9300
gatttatcat ttcaggaaaa aaaaaaacat tcaaatgtgg gctttagctt gttttcagca    9360
gaaagatctt gctccctatt tctaagaggc tgctcaatat tgggaaatat attgaggagt    9420
tattccatgg aaatacaatg cttttccacct actactgtag ttcaataacg tttccacctg    9480
aaaaaatatc atccatgccc agatgaaaag gaagagtatc tgtcactgct acatagttcc    9540
ttaatttgac tgtaacacat ttgtttcaag tctttggatt caaacaaccg gattgtatta    9600
aaattgacaa taaataaatg ttgattaaat ac                                 9632
```

<210> SEQ ID NO 34
<211> LENGTH: 2850
<212> TYPE: PRT
<213> ORGANISM: Homo sapiens

<400> SEQUENCE: 34

```
Met Pro Lys Leu Leu Gln Gly Val Ile Thr Val Ile Asp Val Phe Tyr
1               5                   10                  15

Gln Tyr Ala Thr Gln His Gly Glu Tyr Asp Thr Leu Asn Lys Ala Glu
            20                  25                  30

Leu Lys Glu Leu Leu Glu Asn Glu Phe His Gln Ile Leu Lys Asn Pro
        35                  40                  45

Asn Asp Pro Asp Thr Val Asp Ile Ile Leu Gln Ser Leu Asp Arg Asp
    50                  55                  60

His Asn Lys Lys Val Asp Phe Thr Glu Tyr Leu Leu Met Ile Phe Lys
65                  70                  75                  80

Leu Val Gln Ala Arg Asn Lys Ile Ile Gly Lys Asp Tyr Cys Gln Val
                85                  90                  95

Ser Gly Ser Lys Leu Arg Asp Asp Thr His Gln His Gln Glu Glu Gln
            100                 105                 110

Glu Glu Thr Glu Lys Glu Glu Asn Lys Arg Gln Glu Ser Ser Phe Ser
        115                 120                 125

His Ser Ser Trp Ser Ala Gly Glu Asn Asp Ser Tyr Ser Arg Asn Val
    130                 135                 140

Arg Gly Ser Leu Lys Pro Gly Thr Glu Ser Ile Ser Arg Arg Leu Ser
145                 150                 155                 160

Phe Gln Arg Asp Phe Ser Gly Gln His Asn Ser Tyr Ser Gly Gln Ser
                165                 170                 175

Ser Ser Tyr Gly Glu Gln Asn Ser Asp Ser His Gln Ser Ser Gly Arg
            180                 185                 190

Gly Gln Cys Gly Ser Gly Ser Gly Gln Ser Pro Asn Tyr Gly Gln His
        195                 200                 205

Gly Ser Gly Ser Gly Gln Ser Ser Asn Asp Thr His Gly Ser Gly
    210                 215                 220

Ser Gly Gln Ser Ser Gly Phe Ser Gln His Lys Ser Ser Ser Gly Gln
225                 230                 235                 240

Ser Ser Gly Tyr Ser Gln His Gly Ser Gly Ser Gly His Ser Ser Gly
                245                 250                 255

Tyr Gly Gln His Gly Ser Arg Ser Gly Gln Ser Ser Arg Gly Glu Arg
            260                 265                 270

His Arg Ser Ser Ser Gly Ser Ser Ser Tyr Gly Gln His Gly Ser
        275                 280                 285

Gly Ser Arg Gln Ser Leu Gly His Gly Arg Gln Gly Ser Gly Ser Arg
    290                 295                 300

Gln Ser Pro Ser His Val Arg His Gly Ser Gly Ser Gly His Ser Ser
305                 310                 315                 320

Ser His Gly Gln His Gly Ser Gly Ser Ser Tyr Ser Tyr Ser Arg Gly
                325                 330                 335

His Tyr Glu Ser Gly Ser Gly Gln Thr Ser Gly Phe Gly Gln His Glu
            340                 345                 350

Ser Gly Ser Gly Gln Ser Ser Gly Tyr Ser Lys His Gly Ser Gly Ser
        355                 360                 365

Gly His Ser Ser Ser Gly Gln His Gly Ser Thr Ser Gly Gln Ala
    370                 375                 380

Ser Ser Ser Gly Gln His Gly Ser Ser Ser Arg Gln Ser Ser Ser Tyr
385                 390                 395                 400

Gly Gln His Glu Ser Ala Ser Arg His Ser Ser Gly Arg Gly Gln His
                405                 410                 415
```

```
Ser Ser Gly Ser Gly Gln Ser Pro Gly His Gly Gln Arg Gly Ser Gly
            420                 425                 430

Ser Gly Gln Ser Pro Ser Ser Gly Gln His Gly Thr Gly Phe Gly Arg
        435                 440                 445

Ser Ser Ser Ser Gly Pro Tyr Val Ser Gly Ser Gly Tyr Ser Ser Gly
    450                 455                 460

Phe Gly His His Glu Ser Ser Glu His Ser Ser Gly Tyr Thr Gln
465             470                 475                 480

His Gly Ser Gly Ser Gly His Ser Gly His Gly Gln His Gly Ser
                485                 490                 495

Arg Ser Gly Gln Ser Ser Arg Gly Glu Arg Gln Gly Ser Ser Ala Gly
            500                 505                 510

Ser Ser Ser Ser Tyr Gly Gln His Gly Ser Gly Ser Arg Gln Ser Leu
        515                 520                 525

Gly His Ser Arg His Gly Ser Gly Ser Gly Gln Ser Pro Ser Pro Ser
    530                 535                 540

Arg Gly Arg His Glu Ser Gly Ser Arg Gln Ser Ser Tyr Gly Pro
545                 550                 555                 560

His Gly Tyr Gly Ser Gly Arg Ser Ser Ser Arg Gly Pro Tyr Glu Ser
            565                 570                 575

Gly Ser Gly His Ser Ser Gly Leu Gly His Gln Glu Ser Arg Ser Gly
        580                 585                 590

Gln Ser Ser Gly Tyr Gly Gln His Gly Ser Ser Ser Gly His Ser Ser
        595                 600                 605

Thr His Gly Gln His Gly Ser Thr Ser Gly Gln Ser Ser Ser Cys Gly
            610                 615                 620

Gln His Gly Ala Thr Ser Gly Gln Ser Ser His Gly Gln His Gly
625                 630                 635                 640

Ser Gly Ser Ser Gln Ser Ser Arg Tyr Gly Gln Gln Gly Ser Gly Ser
            645                 650                 655

Gly Gln Ser Pro Ser Arg Gly Arg His Gly Ser Asp Phe Gly His Ser
        660                 665                 670

Ser Ser Tyr Gly Gln His Gly Ser Gly Ser Gly Trp Ser Ser Ser Asn
    675                 680                 685

Gly Pro His Gly Ser Val Ser Gly Gln Ser Ser Gly Phe Gly His Lys
    690                 695                 700

Ser Gly Ser Gly Gln Ser Ser Gly Tyr Ser Gln His Gly Ser Gly Ser
705                 710                 715                 720

Ser His Ser Ser Gly Tyr Arg Lys His Gly Ser Arg Ser Gly Gln Ser
            725                 730                 735

Ser Arg Ser Glu Gln His Gly Ser Ser Ser Gly Leu Ser Ser Ser Tyr
        740                 745                 750

Gly Gln His Gly Ser Gly Ser His Gln Ser Ser Gly His Gly Arg Gln
        755                 760                 765

Gly Ser Gly Ser Gly His Ser Pro Ser Arg Val Arg His Gly Ser Ser
        770                 775                 780

Ser Gly His Ser Ser His Gly Gln His Gly Ser Gly Thr Ser Cys
785                 790                 795                 800

Ser Ser Ser Cys Gly His Tyr Glu Ser Gly Ser Gly Gln Ala Ser Gly
            805                 810                 815

Phe Gly Gln His Glu Ser Gly Ser Gly Gln Gly Tyr Ser Gln His Gly
            820                 825                 830
```

```
Ser Ala Ser Gly His Phe Ser Gln Gly Arg His Gly Ser Thr Ser
        835                 840                 845
Gly Gln Ser Ser Ser Gly Gln His Asp Ser Ser Gly Gln Ser
    850                 855                 860
Ser Ser Tyr Gly Gln His Glu Ser Ala Ser His His Ala Ser Gly Arg
865                 870                 875                 880
Gly Arg His Gly Ser Gly Ser Gly Gln Ser Pro Gly His Gly Gln Arg
                885                 890                 895
Gly Ser Gly Ser Gly Gln Ser Pro Ser Tyr Gly Arg His Gly Ser Gly
                900                 905                 910
Ser Gly Arg Ser Ser Ser Ser Gly Arg His Gly Ser Gly Ser Gly Gln
            915                 920                 925
Ser Ser Gly Phe Gly His Lys Ser Ser Ser Gly Gln Ser Ser Gly Tyr
    930                 935                 940
Thr Gln His Gly Ser Gly Ser Gly His Ser Ser Ser Tyr Glu Gln His
945                 950                 955                 960
Gly Ser Arg Ser Gly Gln Ser Ser Arg Ser Glu Gln His Gly Ser Ser
                965                 970                 975
Ser Gly Ser Ser Ser Ser Tyr Gly Gln His Gly Ser Gly Ser Arg Gln
    980                 985                 990
Ser Leu Gly His Gly Gln His Gly Ser Gly Ser Gly Gln Ser Pro Ser
        995                 1000                1005
Pro Ser Arg Gly Arg His Gly Ser Gly Ser Gly Gln Ser Ser Ser
    1010                1015                1020
Tyr Gly Pro Tyr Arg Ser Gly Ser Gly Trp Ser Ser Arg Gly
    1025                1030                1035
Pro Tyr Glu Ser Gly Ser Gly His Ser Ser Gly Leu Gly His Arg
    1040                1045                1050
Glu Ser Arg Ser Gly Gln Ser Ser Gly Tyr Gly Gln His Gly Ser
    1055                1060                1065
Ser Ser Gly His Ser Ser Thr His Gly Gln His Gly Ser Thr Ser
    1070                1075                1080
Gly Gln Ser Ser Ser Cys Gly Gln His Gly Ala Ser Ser Gly Gln
    1085                1090                1095
Ser Ser Ser His Gly Gln His Gly Ser Gly Ser Ser Gln Ser Ser
    1100                1105                1110
Gly Tyr Gly Arg Gln Gly Ser Gly Ser Gly Gln Ser Pro Gly His
    1115                1120                1125
Gly Gln Arg Gly Ser Gly Ser Arg Gln Ser Pro Ser Tyr Gly Arg
    1130                1135                1140
His Gly Ser Gly Ser Gly Arg Ser Ser Ser Ser Gly Gln His Gly
    1145                1150                1155
Ser Gly Leu Gly Glu Ser Gly Phe Gly His His Glu Ser Ser
    1160                1165                1170
Ser Gly Gln Ser Ser Ser Tyr Ser Gln His Gly Ser Gly Ser Gly
    1175                1180                1185
His Ser Ser Gly Tyr Gly Gln His Gly Ser Arg Ser Gly Gln Ser
    1190                1195                1200
Ser Arg Gly Glu Arg His Gly Ser Ser Gly Ser Ser Ser His
    1205                1210                1215
Tyr Gly Gln His Gly Ser Gly Ser Arg Gln Ser Ser Gly His Gly
    1220                1225                1230
Arg Gln Gly Ser Gly Ser Gly His Ser Pro Ser Arg Gly Arg His
```

```
                    1235                1240                1245
Gly Ser Gly Leu Gly His Ser Ser His Gly Gln His Gly Ser
         1250                1255                1260
Gly Ser Gly Arg Ser Ser Arg Gly Pro Tyr Glu Ser Arg Ser
         1265                1270                1275
Gly His Ser Ser Val Phe Gly Gln His Glu Ser Ser Gly His
         1280                1285                1290
Ser Ser Ala Tyr Ser Gln His Gly Ser Gly Ser Gly His Phe Cys
         1295                1300                1305
Ser Gln Gly Gln His Gly Ser Thr Ser Gly Gln Ser Ser Thr Phe
         1310                1315                1320
Asp Gln Glu Gly Ser Ser Thr Gly Gln Ser Ser Tyr Gly His
         1325                1330                1335
Arg Gly Ser Gly Ser Ser Gln Ser Ser Gly Tyr Gly Arg His Gly
         1340                1345                1350
Ala Gly Ser Gly Gln Ser Pro Ser Arg Gly Arg His Gly Ser Gly
         1355                1360                1365
Ser Gly His Ser Ser Ser Tyr Gly Gln His Gly Ser Gly Ser Gly
         1370                1375                1380
Trp Ser Ser Ser Ser Gly Arg His Gly Ser Gly Ser Gly Gln Ser
         1385                1390                1395
Ser Gly Phe Gly His His Glu Ser Ser Ser Trp Gln Ser Ser Gly
         1400                1405                1410
Cys Thr Gln His Gly Ser Gly Ser Gly His Ser Ser Ser Tyr Glu
         1415                1420                1425
Gln His Gly Ser Arg Ser Gly Gln Ser Ser Arg Gly Glu Arg His
         1430                1435                1440
Gly Ser Ser Ser Gly Ser Ser Ser Ser Tyr Gly Gln His Gly Ser
         1445                1450                1455
Gly Ser Arg Gln Ser Leu Gly His Gly Gln His Gly Ser Gly Ser
         1460                1465                1470
Gly Gln Ser Pro Ser Pro Ser Arg Gly Arg His Gly Ser Gly Ser
         1475                1480                1485
Gly Gln Ser Ser Ser Tyr Ser Pro Tyr Gly Ser Gly Ser Gly Trp
         1490                1495                1500
Ser Ser Ser Arg Gly Pro Tyr Glu Ser Gly Ser Ser His Ser Ser
         1505                1510                1515
Gly Leu Gly His Arg Glu Ser Arg Ser Gly Gln Ser Ser Gly Tyr
         1520                1525                1530
Gly Gln His Gly Ser Ser Ser Gly His Ser Ser Thr His Gly Gln
         1535                1540                1545
His Gly Ser Thr Ser Gly Gln Ser Ser Ser Cys Gly Gln His Gly
         1550                1555                1560
Ala Ser Ser Gly Gln Ser Ser Ser His Gly Gln His Gly Ser Gly
         1565                1570                1575
Ser Ser Gln Ser Ser Gly Tyr Gly Arg Gln Gly Ser Gly Ser Gly
         1580                1585                1590
Gln Ser Pro Gly His Gly Gln Arg Gly Ser Gly Ser Arg Gln Ser
         1595                1600                1605
Pro Ser Tyr Gly Arg His Gly Ser Gly Ser Gly Arg Ser Ser Ser
         1610                1615                1620
Ser Gly Gln His Gly Ser Gly Leu Gly Glu Ser Ser Gly Phe Gly
         1625                1630                1635
```

His His Glu Ser Ser Ser Gly Gln Ser Ser Tyr Ser Gln His
    1640                1645                1650

Gly Ser Gly Ser Gly His Ser Gly Tyr Gly Gln His Gly Ser
    1655                1660                1665

Arg Ser Gly Gln Ser Ser Arg Gly Glu Arg His Gly Ser Ser Ser
    1670                1675                1680

Arg Ser Ser Ser Arg Tyr Gly Gln His Gly Ser Gly Ser Arg Gln
    1685                1690                1695

Ser Ser Gly His Gly Arg Gln Gly Ser Gly Ser Gly Gln Ser Pro
    1700                1705                1710

Ser Arg Gly Arg His Gly Ser Gly Leu Gly His Ser Ser Ser His
    1715                1720                1725

Gly Gln His Gly Ser Gly Ser Gly Arg Ser Ser Ser Arg Gly Pro
    1730                1735                1740

Tyr Glu Ser Arg Ser Gly His Ser Ser Val Phe Gly Gln His Glu
    1745                1750                1755

Ser Gly Ser Gly His Ser Ser Ala Tyr Ser Gln His Gly Ser Gly
    1760                1765                1770

Ser Gly His Phe Cys Ser Gln Gly Gln His Gly Ser Thr Ser Gly
    1775                1780                1785

Gln Ser Ser Thr Phe Asp Gln Glu Gly Ser Ser Thr Gly Gln Ser
    1790                1795                1800

Ser Ser His Gly Gln His Gly Ser Gly Ser Ser Gln Ser Ser Ser
    1805                1810                1815

Tyr Gly Gln Gln Gly Ser Gly Ser Gly Gln Ser Pro Ser Arg Gly
    1820                1825                1830

Arg His Gly Ser Gly Ser Gly His Ser Ser Ser Tyr Gly Gln His
    1835                1840                1845

Gly Ser Gly Ser Gly Trp Ser Ser Ser Ser Gly Arg His Gly Ser
    1850                1855                1860

Gly Ser Gly Gln Ser Ser Gly Phe Gly His His Glu Ser Ser Ser
    1865                1870                1875

Trp Gln Ser Ser Gly Tyr Thr Gln His Gly Ser Gly Ser Gly His
    1880                1885                1890

Ser Ser Ser Tyr Glu Gln His Gly Ser Arg Ser Gly Gln Ser Ser
    1895                1900                1905

Arg Gly Glu Gln His Gly Ser Ser Ser Gly Ser Ser Ser Ser Tyr
    1910                1915                1920

Gly Gln His Gly Ser Gly Ser Arg Gln Ser Leu Gly His Gly Gln
    1925                1930                1935

His Gly Ser Gly Ser Gly Gln Ser Pro Ser Pro Ser Arg Gly Arg
    1940                1945                1950

His Gly Ser Gly Ser Gly Gln Ser Ser Ser Tyr Gly Pro Tyr Gly
    1955                1960                1965

Ser Gly Ser Gly Trp Ser Ser Ser Arg Gly Pro Tyr Glu Ser Gly
    1970                1975                1980

Ser Gly His Ser Ser Gly Leu Gly His Arg Glu Ser Arg Ser Gly
    1985                1990                1995

Gln Ser Ser Gly Tyr Gly Gln His Gly Ser Ser Ser Gly His Ser
    2000                2005                2010

Ser Thr His Gly Gln His Gly Ser Ala Ser Gly Gln Ser Ser Ser
    2015                2020                2025

-continued

Cys Gly Gln His Gly Ala Ser Ser Gly Gln Ser Ser Ser His Gly
    2030                2035                2040

Gln His Gly Ser Gly Ser Ser Gln Ser Ser Gly Tyr Gly Arg Gln
    2045                2050                2055

Gly Ser Gly Ser Gly Gln Ser Pro Gly His Gly Gln Arg Gly Ser
    2060                2065                2070

Gly Ser Arg Gln Ser Pro Ser Tyr Gly Arg His Gly Ser Gly Ser
    2075                2080                2085

Gly Arg Ser Ser Ser Gly Gln His Gly Pro Gly Leu Gly Glu
    2090                2095                2100

Ser Ser Gly Phe Gly His His Glu Ser Ser Ser Gly Gln Ser Ser
    2105                2110                2115

Ser Tyr Ser Gln His Gly Ser Gly Ser Gly His Ser Ser Gly Tyr
    2120                2125                2130

Gly Gln His Gly Ser Arg Ser Gly Gln Ser Ser Arg Gly Glu Arg
    2135                2140                2145

His Gly Ser Ser Ser Gly Ser Ser Ser Arg Tyr Gly Gln His Gly
    2150                2155                2160

Ser Gly Ser Arg Gln Ser Ser Gly His Gly Arg Gln Gly Ser Gly
    2165                2170                2175

Ser Gly His Ser Pro Ser Arg Gly Arg His Gly Ser Gly Ser Gly
    2180                2185                2190

His Ser Ser Ser His Gly Gln His Gly Ser Gly Ser Gly Arg Ser
    2195                2200                2205

Ser Ser Arg Gly Pro Tyr Glu Ser Arg Ser Gly His Ser Ser Val
    2210                2215                2220

Phe Gly Gln His Glu Ser Gly Ser Gly His Ser Ser Ala Tyr Ser
    2225                2230                2235

Gln His Gly Ser Gly Ser Gly His Phe Cys Ser Gln Gly Gln His
    2240                2245                2250

Gly Ser Thr Ser Gly Gln Ser Ser Thr Phe Asp Gln Glu Gly Ser
    2255                2260                2265

Ser Thr Gly Gln Ser Ser Ser His Gly Gln His Gly Ser Gly Ser
    2270                2275                2280

Ser Gln Ser Ser Ser Tyr Gly Gln Gln Gly Ser Gly Ser Gly Gln
    2285                2290                2295

Ser Pro Ser Arg Gly Arg His Gly Ser Gly Ser Gly His Ser Ser
    2300                2305                2310

Ser Tyr Gly Gln His Gly Ser Gly Ser Gly Trp Ser Ser Ser Ser
    2315                2320                2325

Gly Arg His Gly Ser Gly Ser Gly Gln Ser Ser Gly Phe Gly His
    2330                2335                2340

His Glu Ser Ser Ser Trp Gln Ser Ser Gly Tyr Thr Gln His Gly
    2345                2350                2355

Ser Gly Ser Gly His Ser Ser Ser Tyr Glu Gln His Gly Ser Arg
    2360                2365                2370

Ser Gly Gln Ser Ser Arg Gly Glu Arg His Gly Ser Ser Ser Gly
    2375                2380                2385

Ser Ser Ser Ser Tyr Gly Gln His Gly Ser Gly Ser Arg Gln Ser
    2390                2395                2400

Leu Gly His Gly Gln His Gly Ser Gly Ser Gly Gln Ser Pro Ser
    2405                2410                2415

Pro Ser Arg Gly Arg His Gly Ser Gly Ser Gly Gln Ser Ser Ser

-continued

Tyr Ser Pro Tyr Gly Ser Gly Ser Gly Trp Ser Ser Arg Gly
2435             2440             2445

Pro Tyr Glu Ser Gly Ser Gly His Ser Ser Gly Leu Gly His Arg
2450             2455             2460

Glu Ser Arg Ser Gly Gln Ser Ser Gly Tyr Gly Gln His Gly Ser
2465             2470             2475

Ser Ser Gly His Ser Ser Thr His Gly Gln His Gly Ser Thr Ser
2480             2485             2490

Gly Gln Ser Ser Ser Cys Gly Gln His Gly Ala Ser Ser Gly Gln
2495             2500             2505

Ser Ser Ser His Gly Gln His Gly Ser Gly Ser Ser Gln Ser Ser
2510             2515             2520

Gly Tyr Gly Arg Gln Gly Ser Gly Ser Gly Gln Ser Pro Gly His
2525             2530             2535

Gly Gln Arg Gly Ser Gly Ser Arg Gln Ser Pro Ser Tyr Gly Arg
2540             2545             2550

His Gly Ser Gly Ser Gly Arg Ser Ser Ser Ser Gly Gln His Gly
2555             2560             2565

Ser Gly Leu Gly Glu Ser Ser Gly Phe Gly His His Glu Ser Ser
2570             2575             2580

Ser Gly Gln Ser Ser Ser Tyr Ser Gln His Gly Ser Gly Ser Gly
2585             2590             2595

His Ser Ser Gly Tyr Gly Gln His Gly Ser Arg Ser Gly Gln Ser
2600             2605             2610

Ser Arg Gly Glu Arg His Gly Ser Ser Ser Gly Ser Ser Ser His
2615             2620             2625

Tyr Gly Gln His Gly Ser Gly Ser Arg Gln Ser Ser Gly His Gly
2630             2635             2640

Arg Gln Gly Ser Gly Ser Gly Gln Ser Pro Ser Arg Gly Arg His
2645             2650             2655

Gly Ser Gly Leu Gly His Ser Ser Ser His Gly Gln His Gly Ser
2660             2665             2670

Gly Ser Gly Arg Ser Ser Ser Arg Gly Pro Tyr Glu Ser Arg Leu
2675             2680             2685

Gly His Ser Ser Val Phe Gly Gln His Glu Ser Gly Ser Gly His
2690             2695             2700

Ser Ser Ala Tyr Ser Gln His Gly Ser Gly Ser Gly His Phe Cys
2705             2710             2715

Ser Gln Gly Gln His Gly Ser Thr Ser Gly Gln Ser Ser Thr Phe
2720             2725             2730

Asp Gln Glu Gly Ser Ser Thr Gly Gln Ser Ser Ser Tyr Gly His
2735             2740             2745

Arg Gly Ser Gly Ser Ser Gln Ser Ser Gly Tyr Gly Arg His Gly
2750             2755             2760

Ala Gly Ser Gly Gln Ser Leu Ser His Gly Arg His Gly Ser Gly
2765             2770             2775

Ser Gly Gln Ser Ser Ser Tyr Gly Gln His Gly Ser Gly Ser Gly
2780             2785             2790

Gln Ser Ser Gly Tyr Ser Gln His Gly Ser Gly Ser Gly Gln Asp
2795             2800             2805

Gly Tyr Ser Tyr Cys Lys Gly Gly Ser Asn His Asp Gly Gly Ser
2810             2815             2820

Ser Gly Ser Tyr Phe Leu Ser Phe Pro Ser Ser Thr Ser Pro Tyr
            2825                2830                2835

Glu Tyr Val Gln Glu Gln Arg Cys Tyr Phe Tyr Gln
     2840                2845                2850

<210> SEQ ID NO 35
<211> LENGTH: 23
<212> TYPE: PRT
<213> ORGANISM: Homo sapiens

<400> SEQUENCE: 35

Ser Ser Ser Arg Gly Pro Tyr Glu Ser Gly Ser Gly His Ser Ser Gly
1               5                   10                  15

Leu Gly His Gln Glu Ser Arg
            20

<210> SEQ ID NO 36
<211> LENGTH: 23
<212> TYPE: PRT
<213> ORGANISM: Homo sapiens

<400> SEQUENCE: 36

Arg Ser Glu Gln His Gly Leu Gly Ser Ser His Gly Ser Gly Ser Glu
1               5                   10                  15

Tyr Pro Gly Arg Ser Ser Ser
            20

<210> SEQ ID NO 37
<211> LENGTH: 14
<212> TYPE: PRT
<213> ORGANISM: Homo sapiens

<400> SEQUENCE: 37

Tyr Gly Gln Gln Gly Ser Gly Ser Gly Gln Ser Pro Ser Arg
1               5                   10

<210> SEQ ID NO 38
<211> LENGTH: 14
<212> TYPE: PRT
<213> ORGANISM: Homo sapiens

<400> SEQUENCE: 38

Arg Ser Pro Ser Gln Gly Ser Gly Ser Gly Gln Gln Gly Tyr
1               5                   10

<210> SEQ ID NO 39
<211> LENGTH: 12
<212> TYPE: PRT
<213> ORGANISM: Homo sapiens

<400> SEQUENCE: 39

Gly Ser Gly Ser Gly Gln Ser Pro Ser Tyr Gly Arg
1               5                   10

<210> SEQ ID NO 40
<211> LENGTH: 12
<212> TYPE: PRT
<213> ORGANISM: Homo sapiens

<400> SEQUENCE: 40

Arg Gly Tyr Ser Pro Ser Gln Gly Ser Gly Ser Gly
1               5                   10

<210> SEQ ID NO 41
<211> LENGTH: 14
<212> TYPE: PRT
<213> ORGANISM: Homo sapiens

<400> SEQUENCE: 41

His Gly Ser Gly Ser Gly Gln Ser Ser Gly Phe Gly His Lys
1               5                   10

<210> SEQ ID NO 42
<211> LENGTH: 14
<212> TYPE: PRT
<213> ORGANISM: Homo sapiens

<400> SEQUENCE: 42

Lys His Gly Phe Gly Ser Ser Gln Gly Ser Gly Ser Gly His
1               5                   10

<210> SEQ ID NO 43
<211> LENGTH: 19
<212> TYPE: PRT
<213> ORGANISM: Homo sapiens

<400> SEQUENCE: 43

His Gly Ser Ser Ser Gly Ser Ser Ser Tyr Gly Gln His Gly Ser
1               5                   10                  15

Gly Ser Arg

<210> SEQ ID NO 44
<211> LENGTH: 19
<212> TYPE: PRT
<213> ORGANISM: Homo sapiens

<400> SEQUENCE: 44

Arg Ser Gly Ser Gly His Gln Gly Tyr Ser Ser Ser Gly Ser Ser
1               5                   10                  15

Ser Gly His

<210> SEQ ID NO 45
<211> LENGTH: 26
<212> TYPE: PRT
<213> ORGANISM: Homo sapiens

<400> SEQUENCE: 45

His Gly Ser Gly Ser Gly His Ser Ser Tyr Gly Gln His Gly Ser
1               5                   10                  15

Gly Ser Gly Trp Ser Ser Ser Ser Gly Arg
                20                  25

<210> SEQ ID NO 46
<211> LENGTH: 26
<212> TYPE: PRT
<213> ORGANISM: Homo sapiens

<400> SEQUENCE: 46

Arg Gly Ser Ser Ser Ser Trp Gly Ser Gly Ser Gly His Gln Gly Tyr
1               5                   10                  15

Ser Ser Ser His Gly Ser Gly Ser Gly His
                20                  25

<210> SEQ ID NO 47
<211> LENGTH: 10658

<212> TYPE: DNA
<213> ORGANISM: Mus musculus

<400> SEQUENCE: 47

| | | | | |
|---|---|---|---|---|
| accctgcaag | caacatcagt | ctccatccct | actgttcctc | tggtgaacca | ggttaacttg | 60 |
| aatttgcaac | aagatgccta | aactcctgga | aagcattgtc | actgtcatcg | atgttttcta | 120 |
| ccagtatgcc | actgaatatg | ggaactgtga | catgttaagc | aaagaagaga | tgaaagaact | 180 |
| tctggtaaca | gagtttcacc | aaattctgaa | gaatccagat | gatccagaca | ccgtagatat | 240 |
| catcatgcaa | aatctggatc | gagatcataa | ccacaaagtg | gattttactg | agtatcttct | 300 |
| gatgatactc | aagctgacta | aggcttgtaa | taaaattatt | ggcaaagatt | actgccaagc | 360 |
| ttcagggtca | aagcagaaaa | atcacagtca | ccagcaccaa | gaggaacaga | gtaaaaaaga | 420 |
| aacagaaaac | aaggagcaaa | aaggctcttt | aagttctagt | gcaggagaga | atgactctta | 480 |
| ttccaggggc | tcaagaggaa | gcaataaaag | caaatccaaa | aaactaagaa | aagggaagga | 540 |
| gcaaagttct | aaacaaacaa | caaaatcaaa | ttcaagtgat | cacgaaaata | gtgaggatta | 600 |
| tgaacaaggc | cagcatgaat | caggattttc | taactcatct | ggcaacggga | gacctagctc | 660 |
| aaggaaagct | tctggcttcc | ctcaacctgg | ttcagaacca | ggacaatctt | ctagctccag | 720 |
| tacaaaagga | tctggcgaat | gttattcttc | tggtaatgga | aaacatggtt | catcatcagg | 780 |
| aggatcagca | gtttctggct | caggtcactc | taacacctat | ggtaaacaag | gaacaggatc | 840 |
| aaggcattca | tcaagcaaca | ggagaagcag | gtctacctca | agggaatctt | ctggctccca | 900 |
| agaatatagc | tctggatcat | cagaagaacc | tggctttaca | catggatctg | gtcgaaaaaa | 960 |
| ctcttctact | tgtggaaaaa | acggttccta | ctctggacag | tcaacaggca | gacatcaaca | 1020 |
| aggatttgga | tctagtcatg | aattagaatc | cggtcaatca | atcacctctg | ctaaccatgg | 1080 |
| ctctcattct | aatcagtcat | catgcagtgg | cacaagagag | tgtgggtcta | gcgagtcttc | 1140 |
| catgaagaag | acccatgttt | ctggttcagg | acactcttca | agtacaggta | aatatacatc | 1200 |
| cacttcagga | caaaattata | actccactag | acaaggttgc | ggacaaggca | agtcttctgg | 1260 |
| gtctgaacaa | tatggtgcct | catcaggaca | gtcttcaggc | tgttcgtcag | gtcagtccac | 1320 |
| tcgctatggt | gaacaaggtt | caggatcacg | taactcatct | acccaaagca | gaggcaggtc | 1380 |
| tacctcaagg | gagtcttcta | catctcaaca | gtttggatct | ggctcaggaa | gatcttctgg | 1440 |
| ctttagtcaa | ggtggatctg | ggcaaggtcg | atcttctcgt | ggtggacagc | agggttcctt | 1500 |
| ctctggacag | acagaaggca | gtcaacagca | tggatcttgt | tgcggtcagt | cttctgggta | 1560 |
| tggtcaaaat | gaatatggct | caggtcattc | tgccagctct | ggtcagcagg | ctctcatta | 1620 |
| cagtcagtct | tccagctatg | gcacacataa | ctcaggtgga | agcccgtctt | ccagccagag | 1680 |
| gggacatggc | tctcgttctg | gacgatcttc | aggtttaggt | caatatggat | ccccttcagg | 1740 |
| acaaacttct | agctccacta | gacagggttc | tggacaaggt | caggcctctg | ggtcaggacg | 1800 |
| atatggtgcc | tcatcaggac | agacttcagg | ctgtgggtca | ggtcagtcca | ctcgctatgg | 1860 |
| tgaacaaggt | tcaggatcac | gtaactcatc | tacccaaagc | agaggcaggt | ctacctcaag | 1920 |
| ggagtcttct | acatctcaaa | ggtatggatc | tggctcagga | gaatcttctg | gctttagtca | 1980 |
| aggtggatct | gggcaaggtc | gatcttctcg | tggtggacaa | cagggttcgt | tctctggaca | 2040 |
| gacatcaggt | agaagtcagc | atcaatctgg | ctccaggcat | ggatctggct | caggacagtt | 2100 |
| tcccatctct | ggacagcagg | gctctcatca | cggtcattct | tccagttctg | gcacacataa | 2160 |
| ctcagggtca | agccagtctt | cttccaccca | gtggagtcac | ggttctggtt | cagaacagtc | 2220 |

```
ttctggtttg ggtcattatg gttccacatc aggacaaact gctagctcca ctagacaggg    2280
ttctggacaa ggtcaggcct ctgggtcagg acgatgtggc gcctcatcag gacagacttc    2340
aggctgtggg tcaggtcagt ccactcgcta tggtgaacaa ggttcaggat cacgtaactc    2400
atctacccaa agcagaggca ggtctacctc aagggagtct tctacatctc aaaggtatgg    2460
atctggctca ggaggatctt ctggctttag tcaaggtgga tctgggcaag gtcgatcttc    2520
tcgtggtgga cagcagggtt ccttctctgg acagacagaa ggcagtcaac agcatggatc    2580
ttgttgcggt cagtcttctg ggtatggtca aaatgaatat ggctcaggtc attctgccag    2640
ctctggtcag cagggctctc attacagtca gtcttccagc tatggcacac ataactcagg    2700
tggaagcccc tcttccagcc agaggggaca tggctctcgt tctggacgat cttcaggttt    2760
aggtcaatat ggatcccctt caggacaaac ttctagctcc actagacagg gttctggaca    2820
aggtcaggcc tctgggtcag gacgatatgg tgcctcatca ggacagactt caggctgtgg    2880
gtcaggtcag tccactcgct atggtgaaca aggttcagga tcacgtaact catctaccca    2940
aagcagaggc aggtctacct caaggagtc ttctacatct caaaggtatg gatctggctc    3000
aggagaatct tctggcttta gtcaaggtgg atctgggcaa ggtcgatctt ctcgtggtgg    3060
acaacagggt tcgttctctg gacagacatc aggtagaagt cagcatcaat ctggctccag    3120
gcatggatct ggctcaggac agtttcccat ctctggacag cagggctctc atcacggtca    3180
ttcttccagt tctggcacac ataactcagg gtcaagccag tcttcttcca cccagtggag    3240
tcacggttct ggttcagaac agtcttctgg tttgggtcat tatggttcca catcaggaca    3300
aactgctagc tccactagac accgttctgg acaaggtcag gcctctgggt caggacgatg    3360
tggcgcctca tcaggacaga cttcaggctg tgggtcaggt cagtccactc gctatgatga    3420
acaaggttca ggatcacgta actcatctac ccaaagcaga ggcaggtcta cctcaaggga    3480
gtcttctaca tctcaacggt ttggatctgg ctcaggagga tcttctggct ttagtcaagg    3540
tagatctggg caaggtcgat cttctcgtgg tggacagcag ggttccttct ctggacagac    3600
agaaggcagt caacagcatg gatcttgttg cggtcagtct tctgggtatg gtcaaaatga    3660
atatggctca ggtcattctg ccagctctgg tcagcagggc tctcattaca gtcagtcttc    3720
cagctatggc acacataact caggtggaag ccccctcttcc agccagaggg gacatggctc    3780
tcgttctgga cgatcttcag gtttaggtca atatggatcc ccttcaggac aaacttctag    3840
ctccactaga cagggttctg gacaaggtca ggcctctggg tcaggacgat atggtgcctc    3900
atcaggacag acttcaggct gtgggtcagg tcagtccact cgctatggtg aacaaggttc    3960
aggatcacgt aactcatcta cccaaagcag aggcaggtct acctcaaggg agtcttctac    4020
atctcaaagg tatggatctg gctcaggaga atcttctggc tttagtcaag gtggatctgg    4080
gcaaggtcga tcttctcgtg gtggacaaca gggttcgttc tctggacaga catcaggtag    4140
aagtcagcat caatctggct ccaggcatgg atctggctca ggacagtttc ccatctctgg    4200
acagcagggc tctcatcacg gtcattcttc cagttctggc acacataact cagggtcaag    4260
ccagtcttct tccacccagt ggagtcacgg ttctggttca gaacagtctt ctggtttggg    4320
tcattatggt tccacatcag acaaactgc tagctccact agacagggtt ctggacaagg    4380
tcaggcctct gggtcaggac gatgtggcgc ctcatcagga cagacttcag gctgtgggtc    4440
aggtcagtcc actcgctatg gtgaacaagg ttcaggatca cgtaactcat ctacccaaag    4500
cagaggcagg tctacctcaa gggagtcttc tacatctcaa cggtttggat ctggctcagg    4560
aggatcttct ggctttagtc aaggtagatc tgggcaaggt cgatcttctc gtggtggaca    4620
```

-continued

```
gcagggttcc ttctctggac agacagaagg cagtcaacag catggatctt gttgcggtca   4680
gtcttctggg tatggtcaaa atgaatatgg ctcaggtcat tctgccagct ctggtcagca   4740
gggctctcat tacagtcagt cttccagcta tggcacacat aactcaggtg aagcccctc    4800 ttccagccag aggggacatg gctctcgttc tggacgatct tcaggtttag gtcaatatgg   4860
atccccttca ggacaaactt ctagctccac tagacagggt tctggacaag gtcaggcctc   4920
tgggtcagga cgatatggtg cctcatcagg acagacttca ggctgtgggt caggtcagtc   4980
cactcgctat ggtgaacaag gttcaggatc acgtaactca tctacccaaa gcagaggcag   5040
gtctacctca agggagtctt ctacatctca aggtatggat ctggctcag gagaatcttc    5100 tggctttagt caaggtggat ctgggcaagg tcgatcttct cgtggtggac aacagggttc   5160
gttctctgga cagacatcag gtagaagtca gcatcaatct ggctccaggc atggatctgg   5220
ctcaggacag tttcccatct ctggacagca gggctctcat cacggtcatt cttccagttc   5280
tggcacacat aactcaggt caagccagtc ttcttccacc cagtggagtc acggttctgg    5340
ttcagaacag tcttctggtt tgggtcatta tggttccaca tcaggacaaa ctgctagctc   5400
cactagacag ggttctggac aaggtcaggc ctctgggtca ggacgatgtg cgcctcatc    5460 aggacagact tcaggctgtg gtcaggtca gtccactcgc tatggtgaac aaggttcagg    5520
atcacgtaac tcatctaccc aaagcagagg caggtctacc tcaagggagt cttctacatc   5580
tcaaaggtat ggatctggct caggaggatc ttctggcttt agtcaaggtg gatctgggca   5640
aggtcgatct tctcgtggtg gacagcaggg ttccttctct ggacagacag aaggcagtca   5700
acagcatgga tcttgttgcg gtcagtcttc tgggtatggt caaaatgaat atggctcagg   5760
tcattctgcc agctctggtc agcagggctc tcattacagt cagtcttcca gctatggcac   5820
acataactca ggtggaagcc cctcttccag ccagagggga catggctctc gttctggacg   5880
atcttcaggt ttaggtcaat atggatcccc ttcaggacaa acttctagct ccactagaca   5940
gggttctgga caaggtcagg cctctgggtc aggacgatat ggtgcctcat caggacagac   6000
ttcaggctgt gggtcaggtc agtccactcg ctatggtgaa caaggttcag gatcacgtaa   6060
ctcatctacc caaagcagag gcaggtctac ctcaagggag tcttctacat ctcaaaggta   6120
tggatctggc tcaggagaat cttctggctt tagtcaaggt ggatctgggc aaggtcgatc   6180
ttctcgtggt ggacaacagg gttcgttctc tggacagaca tcaggtagaa gtcagcatca   6240
atctggctcc aggcatggat ctggctcagg acagtttccc atctctggac agcagggctc   6300
tcatcacggt cattcttcca gttctggcac acataactca gggtcaagcc agtcttcttc   6360
cacccagtgg agtcacggtt ctggttcaga acagtcttct ggtttgggtc attatggttc   6420
cacatcagga caaactgcta gctccactag acagggttct ggacaaggtc aggcctctgg   6480
gtcaggacga tgtggcgcct catcaggaca gacttcaggc tgtgggtcag gtcagtccac   6540
tcgctatggt gaacaaggtt caggatcacg taactcatct acccaaagca gaggcaggtc   6600
tacctcaagg gagtcttcta catctcaaag gtatggatct ggctcaggag atcttctgg    6660 ctttagtcaa ggtggatctg gcaaggtcg atcttctcgt ggtggacaac agggttcgtt    6720
ctctggacag acatcaggta gaagtcagca tcaatctggc tccaggcatg gatctggctc   6780
aggacagttt cccatctctg gacagcaggg ctctcatcac ggtcattctt ccagttctgg   6840
cacacataac tcagggtcaa gccagtcttc ttccacccag tggagtcacg gttctggttc   6900
agaacagtct tctggtttag gtcaatatgg atccccttca ggacaaactt ctagctccac   6960
```

```
tagacagggt tctggacaag gtcaggcctc tgggtcagga cgatatggtg cctcatcagg    7020
acagacttca ggctgtgggt caggtcagtc cactcgctat ggtgaacaag gttcaggatc    7080
acgtaactca tctacccaaa gcagaggcag gtctacctca agggagtctt ctacatctca    7140
aaggtatgga tctggctcag gagaatcttc tggctttagt caaggtggat ctgggcaagg    7200
tcgatcttct cgtggtggac aacagggttc gttctctgga cagacatcag gtagaagtca    7260
gcatcaatct ggctccaggc atggatctgg ctcaggacag tttcccatct ctggacagca    7320
gggctctcat cacggtcatt cttccagttc tggcacacat aactcagggt caagccagtc    7380
ttcttccacc cagtggagtc acggttctgg ttcagaacag tcttctggtt tgggtcatta    7440
tggttccaca tcaggacaaa ctgctagctc cactagacag ggttctggac aaggtcaggc    7500
ctctgggtca ggacgatgtg cgcctcatc aggacagact tcaggctgtg gtcaggtca     7560 gtccactcgc tatggtgaac aaggttcagg atcacgtaac tcatctaccc aaagcagagg    7620
caggtctacc tcaagggagt cttctacatc tcaacggttt ggatctggct caggaggatc    7680
ttctggcttt agtcaaggta gatctgggca aggtcgatct ctcgtggtg acagcaggg     7740 ttccttctct ggacagacag aaggcagtca acagcatgga tcttgttgcg gtcagtcttc    7800
tgggtatggt caaaatgaat atggctcagg tcattctgcc agctctggtc agcagggctc    7860
tcattacagt cagtcttcca gctatggcac acataactca ggtggaagcc cctcttccag    7920
ccagagggga catggctctc gttctggacg atcttcaggt ttaggtcaat atggatcccc    7980
ttcaggacaa acttctagct ccactagaca gggttctgga caaggtcagg cctctgggtc    8040
aggacgatat ggtgcctcat caggacagac ttcaggctgt gggtcaggtc agtccactcg    8100
ctatggtgaa caaggttcag gatcacgtaa ctcatctacc caaagcagag gcaggtctac    8160
ctcaagggag tcttctacat ctcaaaggta tggatctggc tcaggagaat cttctggctt    8220
tagtcaaggt ggatctgggc aaggtcgatc ttctcgtggt ggacaacagg gttcgttctc    8280
tggacagaca tcaggtagaa gtcagcatca atctggctcc aggcatggat ctggctcagg    8340
acagtttccc atctctggac agcagggctc tcatcacggt cattcttcca gttctggcac    8400
acataactca gggtcaagcc agtcttcttc cacccagtgg agtcacggtt ctggttcaga    8460
acagtcttct ggtttgggtc attatggttc cacatcagga caaactgcta gctccactag    8520
acagggttct ggacaaggtc aggcctctgg gtcaggacga tgtggcgcct catcaggaca    8580
gacttcaggc tgtgggtcag gtcagtccac tcgctatggt gaacaaggtt caggatcacg    8640
taactcatct acccaaagca gaggcaggtc tacctcaagg gagtcttcat gttcccaaca    8700
cgatgtttca ggctcaggag agtcttctag ctttagtcag catcggtctt gtcaaagcca    8760
ggcctctcac aatgggcaat gtggtccttt ttctggacaa tcatctggtc atattcaaca    8820
tggaccttgt tttggtcaaa ctgaaggctc atttcagtca tctaactgtg acagcaggg    8880 tactacttca taccaatctt ctggttttga ccagcaaagg tctggattac atcagtcttt    8940
tccctgtagt aatcatgagt ccacctctca agagtattct agctttggat catgtgtgtc    9000
tggttcagga gaatgttctg gctttggtaa ccaagtatct agaccaagtc agtctactta    9060
tgagcatcat gaatctaata gaaatcaatc ttctggctat agacaatata atactgcatc    9120
aggacagtca tactgcggtg gtcagtgtgg atctaattca aaccaatcct ctagctacag    9180
agaacaggga cttggttcaa atcagtcttc tcagtatggc caatatagat gtccctcaag    9240
tcattactct agccagagcc aacatggagt tgggtgtagt catggtttta acactggtca    9300
atatgggtct ggttcctatc cctcttctaa ctccagacaa aactgtccag gatctggtct    9360
```

```
atgccctact tcagaacaat atgggtctgg ttcatgtcag tcctttagtc ctggatcatg    9420
tggttctgga tatggtcaat attctaactt tgaacaacct cagtcaaata ggagatgcgg    9480
aaaccagtgg gaatctggct gtagctcctc aaattgtaat gaaaatcaat caataagagt    9540
gcatagacaa gtagaaacct cctcaggctg tggctttgga caattttctt cacaggaaca    9600
gattagatct gatactactg gtaaattgtc actttgtaat gtggacaata gacaaggtaa    9660
ctgtaagtat cagataatca agggaagtaa ctttggaatg agaaacacag tctcaggacc    9720
tcatagtttc aatagtagca ctccactgta tgagtatgtc caagagcaga gacgctaatt    9780
ctcatagtaa ataagaact gtgataaaat taacataaat gttaatttaa gaatgagaa     9840 attatgatag ttaagaagct catcatgaaa ttcctttctc aatctggaca tatctgctct    9900
catccattta aaatgaaaat tagcgtatat ttctagttat tgggttcctt ccaaataaca    9960
tatgatagct gggttactta ggatctatta cagtggataa atgtttggtt taagggaatt   10020
aagttaggaa gaataatttg aagaatatgg gatttaatta agtatctatc taaaagatta   10080
ttatttagtt aagaatgatg ctaaagctaa gcttatagtt ttaaagggca atatattata   10140
aatgtatcat cagtccagtt gccaaagctt tactttacat taacagtcta atttttaatg   10200
tataaaatgt tagatggcaa aagcaagact tatatgtatg tgtgtttcta ttcttacaca   10260
aatcaccaag atactctggc acagtttaaa tcaataaatg gacaagtggc actaagctat   10320
tgttccagat gcatattccc agccaatgga aaagtggtgc aggagcaaag gatccaaatg   10380
tggactttac ctttatttca gcaagagata tcctggcttc catttgtaag aaattgtttt   10440
agattagaaa agtttatcca tagtacatac agctttgaag tctaagtagt ttactggtct   10500
tcccatgtgg agatatcatt aataacaaga cagaaaggaa gcttgccatt gttataaaga   10560
tctttgtttg actgtaatgt atttctttca cgtctttgga ttcaaacaac tggattacat   10620
taatattgac aataaattgg atggtgatta aatactaa                           10658
```

<210> SEQ ID NO 48
<211> LENGTH: 3234
<212> TYPE: PRT
<213> ORGANISM: Mus musculus

<400> SEQUENCE: 48

```
Met Pro Lys Leu Leu Glu Ser Ile Val Thr Val Ile Asp Val Phe Tyr
 1               5                  10                  15

Gln Tyr Ala Thr Glu Tyr Gly Asn Cys Asp Met Leu Ser Lys Glu Glu
            20                  25                  30

Met Lys Glu Leu Leu Val Thr Glu Phe His Gln Ile Leu Lys Asn Pro
        35                  40                  45

Asp Asp Pro Asp Thr Val Asp Ile Ile Met Gln Asn Leu Asp Arg Asp
    50                  55                  60

His Asn His Lys Val Asp Phe Thr Glu Tyr Leu Leu Met Ile Leu Lys
65                  70                  75                  80

Leu Thr Lys Ala Cys Asn Lys Ile Ile Gly Lys Asp Tyr Cys Gln Ala
                85                  90                  95

Ser Gly Ser Lys Gln Lys Asn His Ser His Gln His Gln Glu Glu Gln
            100                 105                 110

Ser Lys Lys Glu Thr Glu Asn Lys Glu Gln Lys Gly Ser Leu Ser Ser
        115                 120                 125

Ser Ala Gly Glu Asn Asp Ser Tyr Ser Arg Gly Ser Arg Gly Ser Asn
    130                 135                 140
```

```
Lys Ser Lys Ser Lys Leu Arg Lys Gly Lys Glu Gln Ser Ser Lys
145                 150                 155                 160

Gln Thr Thr Lys Ser Asn Ser Ser Asp His Glu Asn Ser Glu Asp Tyr
                165                 170                 175

Glu Gln Gly Gln His Glu Ser Gly Phe Ser Asn Ser Ser Gly Asn Gly
            180                 185                 190

Arg Pro Ser Ser Arg Lys Ala Ser Gly Phe Pro Gln Pro Gly Ser Glu
        195                 200                 205

Pro Gly Gln Ser Ser Ser Ser Thr Lys Gly Ser Gly Glu Cys Tyr
    210                 215                 220

Ser Ser Gly Asn Gly Lys His Gly Ser Ser Gly Gly Ser Ala Val
225                 230                 235                 240

Ser Gly Ser Gly His Ser Asn Thr Tyr Gly Lys Gln Gly Thr Gly Ser
                245                 250                 255

Arg His Ser Ser Ser Asn Arg Arg Ser Arg Ser Thr Ser Arg Glu Ser
            260                 265                 270

Ser Gly Ser Gln Glu Tyr Ser Ser Gly Ser Ser Glu Glu Pro Gly Phe
        275                 280                 285

Thr His Gly Ser Gly Arg Lys Asn Ser Ser Thr Cys Gly Lys Asn Gly
    290                 295                 300

Ser Tyr Ser Gly Gln Ser Thr Gly Arg His Gln Gln Gly Phe Gly Ser
305                 310                 315                 320

Ser His Glu Leu Glu Ser Gly Gln Ser Ile Thr Ser Ala Asn His Gly
                325                 330                 335

Ser His Ser Asn Gln Ser Ser Cys Ser Gly Thr Arg Glu Cys Gly Ser
            340                 345                 350

Ser Glu Ser Ser Met Lys Lys Thr His Val Ser Gly Ser Gly His Ser
        355                 360                 365

Ser Ser Thr Gly Lys Tyr Thr Ser Thr Ser Gly Gln Asn Tyr Asn Ser
370                 375                 380

Thr Arg Gln Gly Cys Gly Gln Gly Lys Ser Ser Gly Ser Glu Gln Tyr
385                 390                 395                 400

Gly Ala Ser Ser Gly Gln Ser Ser Gly Cys Ser Ser Gly Gln Ser Thr
                405                 410                 415

Arg Tyr Gly Glu Gln Gly Ser Gly Ser Arg Asn Ser Ser Thr Gln Ser
            420                 425                 430

Arg Gly Arg Ser Thr Ser Arg Glu Ser Ser Thr Ser Gln Gln Phe Gly
        435                 440                 445

Ser Gly Ser Gly Arg Ser Ser Gly Phe Ser Gln Gly Gly Ser Gly Gln
    450                 455                 460

Gly Arg Ser Ser Arg Gly Gly Gln Gln Gly Ser Phe Ser Gly Gln Thr
465                 470                 475                 480

Glu Gly Ser Gln Gln His Gly Ser Cys Cys Gly Gln Ser Ser Gly Tyr
                485                 490                 495

Gly Gln Asn Glu Tyr Gly Ser Gly His Ser Ala Ser Ser Gly Gln Gln
            500                 505                 510

Gly Ser His Tyr Ser Gln Ser Ser Tyr Gly Thr His Asn Ser Gly
        515                 520                 525

Gly Ser Pro Ser Ser Ser Gln Arg Gly His Gly Ser Arg Ser Gly Arg
    530                 535                 540

Ser Ser Gly Leu Gly Gln Tyr Gly Ser Pro Ser Gly Gln Thr Ser Ser
545                 550                 555                 560
```

```
Ser Thr Arg Gln Gly Ser Gly Gln Gly Gln Ala Ser Gly Ser Gly Arg
            565                 570                 575

Tyr Gly Ala Ser Ser Gly Gln Thr Ser Gly Cys Gly Ser Gly Gln Ser
            580                 585                 590

Thr Arg Tyr Gly Glu Gln Gly Ser Gly Ser Arg Asn Ser Ser Thr Gln
            595                 600                 605

Ser Arg Gly Arg Ser Thr Ser Arg Glu Ser Ser Thr Ser Gln Arg Tyr
            610                 615                 620

Gly Ser Gly Ser Gly Glu Ser Ser Gly Phe Ser Gln Gly Gly Ser Gly
625                 630                 635                 640

Gln Gly Arg Ser Ser Arg Gly Gln Gln Gly Ser Phe Ser Gly Gln
            645                 650                 655

Thr Ser Gly Arg Ser Gln His Gln Ser Gly Ser Arg His Gly Ser Gly
            660                 665                 670

Ser Gly Gln Phe Pro Ile Ser Gly Gln Gln Gly Ser His His Gly His
            675                 680                 685

Ser Ser Ser Ser Gly Thr His Asn Ser Gly Ser Ser Gln Ser Ser Ser
690                 695                 700

Thr Gln Trp Ser His Gly Ser Gly Ser Glu Gln Ser Ser Gly Leu Gly
705                 710                 715                 720

His Tyr Gly Ser Thr Ser Gly Gln Thr Ala Ser Ser Thr Arg Gln Gly
                    725                 730                 735

Ser Gly Gln Gly Gln Ala Ser Gly Ser Gly Arg Cys Gly Ala Ser Ser
            740                 745                 750

Gly Gln Thr Ser Gly Cys Gly Ser Gly Gln Ser Thr Arg Tyr Gly Glu
            755                 760                 765

Gln Gly Ser Gly Ser Arg Asn Ser Ser Thr Gln Ser Arg Gly Arg Ser
            770                 775                 780

Thr Ser Arg Glu Ser Ser Thr Ser Gln Arg Tyr Gly Ser Gly Ser Gly
785                 790                 795                 800

Gly Ser Ser Gly Phe Ser Gln Gly Gly Ser Gly Gln Gly Arg Ser Ser
                    805                 810                 815

Arg Gly Gln Gln Gly Ser Phe Ser Gly Gln Thr Glu Gly Ser Gln
            820                 825                 830

Gln His Gly Ser Cys Cys Gly Gln Ser Ser Gly Tyr Gly Gln Asn Glu
            835                 840                 845

Tyr Gly Ser Gly His Ser Ala Ser Ser Gly Gln Gln Gly Ser His Tyr
            850                 855                 860

Ser Gln Ser Ser Ser Tyr Gly Thr His Asn Ser Gly Gly Ser Pro Ser
865                 870                 875                 880

Ser Ser Gln Arg Gly His Gly Ser Arg Ser Gly Arg Ser Ser Gly Leu
                    885                 890                 895

Gly Gln Tyr Gly Ser Pro Ser Gly Gln Thr Ser Ser Ser Thr Arg Gln
            900                 905                 910

Gly Ser Gly Gln Gly Gln Ala Ser Gly Ser Gly Arg Tyr Gly Ala Ser
            915                 920                 925

Ser Gly Gln Thr Ser Gly Cys Gly Ser Gly Gln Ser Thr Arg Tyr Gly
            930                 935                 940

Glu Gln Gly Ser Gly Ser Arg Asn Ser Ser Thr Gln Ser Arg Gly Arg
945                 950                 955                 960

Ser Thr Ser Arg Glu Ser Ser Thr Ser Gln Arg Tyr Gly Ser Gly Ser
                    965                 970                 975

Gly Glu Ser Ser Gly Phe Ser Gln Gly Gly Ser Gly Gln Gly Arg Ser
```

```
                980             985             990
Ser Arg Gly Gly Gln Gln Gly Ser Phe Ser Gly Gln Thr Ser Gly Arg
            995             1000            1005
Ser Gln His Gln Ser Gly Ser Arg His Gly Ser Gly Ser Gly Gln
    1010            1015            1020
Phe Pro Ile Ser Gly Gln Gln Gly Ser His His Gly His Ser Ser
    1025            1030            1035
Ser Ser Gly Thr His Asn Ser Gly Ser Ser Gln Ser Ser Ser Thr
    1040            1045            1050
Gln Trp Ser His Gly Ser Gly Ser Glu Gln Ser Ser Gly Leu Gly
    1055            1060            1065
His Tyr Gly Ser Thr Ser Gly Gln Thr Ala Ser Ser Thr Arg His
    1070            1075            1080
Arg Ser Gly Gln Gly Gln Ala Ser Gly Ser Gly Arg Cys Gly Ala
    1085            1090            1095
Ser Ser Gly Gln Thr Ser Gly Cys Gly Ser Gly Gln Ser Thr Arg
    1100            1105            1110
Tyr Asp Glu Gln Gly Ser Gly Ser Arg Asn Ser Ser Thr Gln Ser
    1115            1120            1125
Arg Gly Arg Ser Thr Ser Arg Glu Ser Ser Thr Ser Gln Arg Phe
    1130            1135            1140
Gly Ser Gly Ser Gly Gly Ser Ser Gly Phe Ser Gln Gly Arg Ser
    1145            1150            1155
Gly Gln Gly Arg Ser Ser Arg Gly Gly Gln Gln Gly Ser Phe Ser
    1160            1165            1170
Gly Gln Thr Glu Gly Ser Gln Gln His Gly Ser Cys Cys Gly Gln
    1175            1180            1185
Ser Ser Gly Tyr Gly Gln Asn Glu Tyr Gly Ser Gly His Ser Ala
    1190            1195            1200
Ser Ser Gly Gln Gln Gly Ser His Tyr Ser Gln Ser Ser Ser Tyr
    1205            1210            1215
Gly Thr His Asn Ser Gly Gly Ser Pro Ser Ser Ser Gln Arg Gly
    1220            1225            1230
His Gly Ser Arg Ser Gly Arg Ser Ser Gly Leu Gly Gln Tyr Gly
    1235            1240            1245
Ser Pro Ser Gly Gln Thr Ser Ser Ser Thr Arg Gln Gly Ser Gly
    1250            1255            1260
Gln Gly Gln Ala Ser Gly Ser Gly Arg Tyr Gly Ala Ser Ser Gly
    1265            1270            1275
Gln Thr Ser Gly Cys Gly Ser Gly Gln Ser Thr Arg Tyr Gly Glu
    1280            1285            1290
Gln Gly Ser Gly Ser Arg Asn Ser Ser Thr Gln Ser Arg Gly Arg
    1295            1300            1305
Ser Thr Ser Arg Glu Ser Ser Thr Ser Gln Arg Tyr Gly Ser Gly
    1310            1315            1320
Ser Gly Glu Ser Ser Gly Phe Ser Gln Gly Gly Ser Gly Gln Gly
    1325            1330            1335
Arg Ser Ser Arg Gly Gly Gln Gln Gly Ser Phe Ser Gly Gln Thr
    1340            1345            1350
Ser Gly Arg Ser Gln His Gln Ser Gly Ser Arg His Gly Ser Gly
    1355            1360            1365
Ser Gly Gln Phe Pro Ile Ser Gly Gln Gln Gly Ser His His Gly
    1370            1375            1380
```

-continued

His Ser Ser Ser Ser Gly Thr His Asn Ser Gly Ser Ser Gln Ser
1385                1390                1395

Ser Ser Thr Gln Trp Ser His Gly Ser Gly Ser Glu Gln Ser Ser
1400                1405                1410

Gly Leu Gly His Tyr Gly Ser Thr Ser Gly Gln Thr Ala Ser Ser
1415                1420                1425

Thr Arg Gln Gly Ser Gly Gln Gly Gln Ala Ser Ser Gly Arg
1430                1435                1440

Cys Gly Ala Ser Ser Gly Gln Thr Ser Gly Cys Gly Ser Gly Gln
1445                1450                1455

Ser Thr Arg Tyr Gly Glu Gln Gly Ser Gly Ser Arg Asn Ser Ser
1460                1465                1470

Thr Gln Ser Arg Gly Arg Ser Thr Ser Arg Glu Ser Ser Thr Ser
1475                1480                1485

Gln Arg Phe Gly Ser Gly Ser Gly Gly Ser Ser Gly Phe Ser Gln
1490                1495                1500

Gly Arg Ser Gly Gln Gly Arg Ser Ser Arg Gly Gly Gln Gln Gly
1505                1510                1515

Ser Phe Ser Gly Gln Thr Glu Gly Ser Gln Gln His Gly Ser Cys
1520                1525                1530

Cys Gly Gln Ser Ser Gly Tyr Gly Gln Asn Glu Tyr Gly Ser Gly
1535                1540                1545

His Ser Ala Ser Ser Gly Gln Gln Gly Ser His Tyr Ser Gln Ser
1550                1555                1560

Ser Ser Tyr Gly Thr His Asn Ser Gly Gly Ser Pro Ser Ser Ser
1565                1570                1575

Gln Arg Gly His Gly Ser Arg Ser Gly Arg Ser Ser Gly Leu Gly
1580                1585                1590

Gln Tyr Gly Ser Pro Ser Gly Gln Thr Ser Ser Thr Arg Gln
1595                1600                1605

Gly Ser Gly Gln Gly Gln Ala Ser Gly Ser Gly Arg Tyr Gly Ala
1610                1615                1620

Ser Ser Gly Gln Thr Ser Gly Cys Gly Ser Gly Gln Ser Thr Arg
1625                1630                1635

Tyr Gly Glu Gln Gly Ser Gly Ser Arg Asn Ser Ser Thr Gln Ser
1640                1645                1650

Arg Gly Arg Ser Thr Ser Arg Glu Ser Ser Thr Ser Gln Arg Tyr
1655                1660                1665

Gly Ser Gly Ser Gly Glu Ser Ser Gly Phe Ser Gln Gly Gly Ser
1670                1675                1680

Gly Gln Gly Arg Ser Ser Arg Gly Gly Gln Gln Gly Ser Phe Ser
1685                1690                1695

Gly Gln Thr Ser Gly Arg Ser Gln His Gln Ser Gly Ser Arg His
1700                1705                1710

Gly Ser Gly Ser Gly Gln Phe Pro Ile Ser Gly Gln Gln Gly Ser
1715                1720                1725

His His Gly His Ser Ser Ser Ser Gly Thr His Asn Ser Gly Ser
1730                1735                1740

Ser Gln Ser Ser Ser Thr Gln Trp Ser His Gly Ser Gly Ser Glu
1745                1750                1755

Gln Ser Ser Gly Leu Gly His Tyr Gly Ser Thr Ser Gly Gln Thr
1760                1765                1770

```
Ala Ser Ser Thr Arg Gln Gly Ser Gly Gln Gly Gln Ala Ser Gly
    1775                1780                1785

Ser Gly Arg Cys Gly Ala Ser Ser Gly Gln Thr Ser Gly Cys Gly
    1790                1795                1800

Ser Gly Gln Ser Thr Arg Tyr Gly Glu Gln Gly Ser Gly Ser Arg
    1805                1810                1815

Asn Ser Ser Thr Gln Ser Arg Gly Arg Ser Thr Ser Arg Glu Ser
    1820                1825                1830

Ser Thr Ser Gln Arg Tyr Gly Ser Gly Ser Gly Ser Ser Gly
    1835                1840                1845

Phe Ser Gln Gly Gly Ser Gly Gln Gly Arg Ser Ser Arg Gly Gly
    1850                1855                1860

Gln Gln Gly Ser Phe Ser Gly Gln Thr Glu Gly Ser Gln Gln His
    1865                1870                1875

Gly Ser Cys Cys Gly Gln Ser Ser Gly Tyr Gly Gln Asn Glu Tyr
    1880                1885                1890

Gly Ser Gly His Ser Ala Ser Ser Gly Gln Gln Gly Ser His Tyr
    1895                1900                1905

Ser Gln Ser Ser Ser Tyr Gly Thr His Asn Ser Gly Gly Ser Pro
    1910                1915                1920

Ser Ser Ser Gln Arg Gly His Gly Ser Arg Ser Gly Arg Ser Ser
    1925                1930                1935

Gly Leu Gly Gln Tyr Gly Ser Pro Ser Gly Gln Thr Ser Ser Ser
    1940                1945                1950

Thr Arg Gln Gly Ser Gly Gln Gly Gln Ala Ser Gly Ser Gly Arg
    1955                1960                1965

Tyr Gly Ala Ser Ser Gly Gln Thr Ser Gly Cys Gly Ser Gly Gln
    1970                1975                1980

Ser Thr Arg Tyr Gly Glu Gln Gly Ser Gly Ser Arg Asn Ser Ser
    1985                1990                1995

Thr Gln Ser Arg Gly Arg Ser Thr Ser Arg Glu Ser Ser Thr Ser
    2000                2005                2010

Gln Arg Tyr Gly Ser Gly Ser Gly Glu Ser Ser Gly Phe Ser Gln
    2015                2020                2025

Gly Gly Ser Gly Gln Gly Arg Ser Ser Arg Gly Gly Gln Gln Gly
    2030                2035                2040

Ser Phe Ser Gly Gln Thr Ser Gly Arg Ser Gln His Gln Ser Gly
    2045                2050                2055

Ser Arg His Gly Ser Gly Ser Gly Gln Phe Pro Ile Ser Gly Gln
    2060                2065                2070

Gln Gly Ser His His Gly His Ser Ser Ser Ser Gly Thr His Asn
    2075                2080                2085

Ser Gly Ser Ser Gln Ser Ser Ser Thr Gln Trp Ser His Gly Ser
    2090                2095                2100

Gly Ser Glu Gln Ser Ser Gly Leu Gly His Tyr Gly Ser Thr Ser
    2105                2110                2115

Gly Gln Thr Ala Ser Ser Thr Arg Gln Gly Ser Gly Gln Gly Gln
    2120                2125                2130

Ala Ser Gly Ser Gly Arg Cys Gly Ala Ser Ser Gly Gln Thr Ser
    2135                2140                2145

Gly Cys Gly Ser Gly Gln Ser Thr Arg Tyr Gly Glu Gln Gly Ser
    2150                2155                2160

Gly Ser Arg Asn Ser Ser Thr Gln Ser Arg Gly Arg Ser Thr Ser
```

```
                 2165                2170                2175

Arg Glu Ser Ser Thr Ser Gln Arg Tyr Gly Ser Gly Ser Gly Gly
        2180                2185                2190

Ser Ser Gly Phe Ser Gln Gly Gly Ser Gly Gln Gly Arg Ser Ser
        2195                2200                2205

Arg Gly Gly Gln Gln Gly Ser Phe Ser Gly Gln Thr Ser Gly Arg
        2210                2215                2220

Ser Gln His Gln Ser Gly Ser Arg His Gly Ser Gly Ser Gly Gln
        2225                2230                2235

Phe Pro Ile Ser Gly Gln Gln Gly Ser His His Gly His Ser Ser
        2240                2245                2250

Ser Ser Gly Thr His Asn Ser Gly Ser Ser Gln Ser Ser Ser Thr
        2255                2260                2265

Gln Trp Ser His Gly Ser Gly Ser Glu Gln Ser Ser Gly Leu Gly
        2270                2275                2280

Gln Tyr Gly Ser Pro Ser Gly Gln Thr Ser Ser Ser Thr Arg Gln
        2285                2290                2295

Gly Ser Gly Gln Gly Gln Ala Ser Gly Ser Gly Arg Tyr Gly Ala
        2300                2305                2310

Ser Ser Gly Gln Thr Ser Gly Cys Gly Ser Gly Gln Ser Thr Arg
        2315                2320                2325

Tyr Gly Glu Gln Gly Ser Gly Ser Arg Asn Ser Ser Thr Gln Ser
        2330                2335                2340

Arg Gly Arg Ser Thr Ser Arg Glu Ser Ser Thr Ser Gln Arg Tyr
        2345                2350                2355

Gly Ser Gly Ser Gly Glu Ser Ser Gly Phe Ser Gln Gly Gly Ser
        2360                2365                2370

Gly Gln Gly Arg Ser Ser Arg Gly Gly Gln Gln Gly Ser Phe Ser
        2375                2380                2385

Gly Gln Thr Ser Gly Arg Ser Gln His Gln Ser Gly Ser Arg His
        2390                2395                2400

Gly Ser Gly Ser Gly Gln Phe Pro Ile Ser Gly Gln Gln Gly Ser
        2405                2410                2415

His His Gly His Ser Ser Ser Gly Thr His Asn Ser Gly Ser
        2420                2425                2430

Ser Gln Ser Ser Ser Thr Gln Trp Ser His Gly Ser Gly Ser Glu
        2435                2440                2445

Gln Ser Ser Gly Leu Gly His Tyr Gly Ser Thr Ser Gly Gln Thr
        2450                2455                2460

Ala Ser Ser Thr Arg Gln Gly Ser Gly Gln Gly Gln Ala Ser Gly
        2465                2470                2475

Ser Gly Arg Cys Gly Ala Ser Ser Gly Gln Thr Ser Gly Cys Gly
        2480                2485                2490

Ser Gly Gln Ser Thr Arg Tyr Gly Glu Gln Gly Ser Gly Ser Arg
        2495                2500                2505

Asn Ser Ser Thr Gln Ser Arg Gly Arg Ser Thr Ser Arg Glu Ser
        2510                2515                2520

Ser Thr Ser Gln Arg Phe Gly Ser Gly Ser Gly Ser Ser Gly
        2525                2530                2535

Phe Ser Gln Gly Arg Ser Gly Gln Gly Arg Ser Ser Arg Gly Gly
        2540                2545                2550

Gln Gln Gly Ser Phe Ser Gly Gln Thr Glu Gly Ser Gln Gln His
        2555                2560                2565
```

```
Gly Ser Cys Cys Gly Gln Ser Ser Gly Tyr Gly Gln Asn Glu Tyr
    2570            2575            2580

Gly Ser Gly His Ser Ala Ser Ser Gly Gln Gln Gly Ser His Tyr
    2585            2590            2595

Ser Gln Ser Ser Ser Tyr Gly Thr His Asn Ser Gly Gly Ser Pro
    2600            2605            2610

Ser Ser Ser Gln Arg Gly His Gly Ser Arg Ser Gly Arg Ser Ser
    2615            2620            2625

Gly Leu Gly Gln Tyr Gly Ser Pro Ser Gly Gln Thr Ser Ser Ser
    2630            2635            2640

Thr Arg Gln Gly Ser Gly Gln Gly Gln Ala Ser Gly Ser Gly Arg
    2645            2650            2655

Tyr Gly Ala Ser Ser Gly Gln Thr Ser Gly Cys Gly Ser Gly Gln
    2660            2665            2670

Ser Thr Arg Tyr Gly Glu Gln Gly Ser Gly Ser Arg Asn Ser Ser
    2675            2680            2685

Thr Gln Ser Arg Gly Arg Ser Thr Ser Arg Glu Ser Ser Thr Ser
    2690            2695            2700

Gln Arg Tyr Gly Ser Gly Ser Gly Glu Ser Ser Gly Phe Ser Gln
    2705            2710            2715

Gly Gly Ser Gly Gln Gly Arg Ser Ser Arg Gly Gly Gln Gln Gly
    2720            2725            2730

Ser Phe Ser Gly Gln Thr Ser Gly Arg Ser Gln His Gln Ser Gly
    2735            2740            2745

Ser Arg His Gly Ser Gly Ser Gly Gln Phe Pro Ile Ser Gly Gln
    2750            2755            2760

Gln Gly Ser His His Gly His Ser Ser Ser Ser Gly Thr His Asn
    2765            2770            2775

Ser Gly Ser Ser Gln Ser Ser Ser Thr Gln Trp Ser His Gly Ser
    2780            2785            2790

Gly Ser Glu Gln Ser Ser Gly Leu Gly His Tyr Gly Ser Thr Ser
    2795            2800            2805

Gly Gln Thr Ala Ser Ser Thr Arg Gln Gly Ser Gly Gln Gly Gln
    2810            2815            2820

Ala Ser Gly Ser Gly Arg Cys Gly Ala Ser Ser Gly Gln Thr Ser
    2825            2830            2835

Gly Cys Gly Ser Gly Gln Ser Thr Arg Tyr Gly Glu Gln Gly Ser
    2840            2845            2850

Gly Ser Arg Asn Ser Ser Thr Gln Ser Arg Gly Arg Ser Thr Ser
    2855            2860            2865

Arg Glu Ser Ser Cys Ser Gln His Asp Val Ser Gly Ser Gly Glu
    2870            2875            2880

Ser Ser Ser Phe Ser Gln His Arg Ser Cys Gln Ser Gln Ala Ser
    2885            2890            2895

His Asn Gly Gln Cys Gly Pro Phe Ser Gly Gln Ser Ser Gly His
    2900            2905            2910

Ile Gln His Gly Pro Cys Phe Gly Gln Thr Glu Gly Ser Phe Gln
    2915            2920            2925

Ser Ser Asn Cys Gly Gln Gln Gly Thr Thr Ser Tyr Gln Ser Ser
    2930            2935            2940

Gly Phe Asp Gln Gln Arg Ser Gly Leu His Gln Ser Phe Pro Cys
    2945            2950            2955
```

```
Ser Asn His Glu Ser Thr Ser Gln Glu Tyr Ser Ser Phe Gly Ser
    2960                2965                2970

Cys Val Ser Gly Ser Gly Glu Cys Ser Gly Phe Gly Asn Gln Val
    2975                2980                2985

Ser Arg Pro Ser Gln Ser Thr Tyr Glu His His Glu Ser Asn Arg
    2990                2995                3000

Asn Gln Ser Ser Gly Tyr Arg Gln Tyr Asn Thr Ala Ser Gly Gln
    3005                3010                3015

Ser Tyr Cys Gly Gly Gln Cys Gly Ser Asn Ser Asn Gln Ser Ser
    3020                3025                3030

Ser Tyr Arg Glu Gln Gly Leu Gly Ser Asn Gln Ser Ser Gln Tyr
    3035                3040                3045

Gly Gln Tyr Arg Cys Pro Ser Ser His Tyr Ser Ser Gln Ser Gln
    3050                3055                3060

His Gly Val Gly Cys Ser His Gly Phe Asn Thr Gly Gln Tyr Gly
    3065                3070                3075

Ser Gly Ser Tyr Pro Ser Ser Asn Ser Arg Gln Asn Cys Pro Gly
    3080                3085                3090

Ser Gly Leu Cys Pro Thr Ser Glu Gln Tyr Gly Ser Gly Ser Cys
    3095                3100                3105

Gln Ser Phe Ser Pro Gly Ser Cys Gly Ser Gly Tyr Gly Gln Tyr
    3110                3115                3120

Ser Asn Phe Glu Gln Pro Gln Ser Asn Arg Arg Cys Gly Asn Gln
    3125                3130                3135

Trp Glu Ser Gly Cys Ser Ser Ser Asn Cys Asn Glu Asn Gln Ser
    3140                3145                3150

Ile Arg Val His Arg Gln Val Glu Thr Ser Ser Gly Cys Gly Phe
    3155                3160                3165

Gly Gln Phe Ser Ser Gln Glu Gln Ile Arg Ser Asp Thr Thr Gly
    3170                3175                3180

Lys Leu Ser Leu Cys Asn Val Asp Asn Arg Gln Gly Asn Cys Lys
    3185                3190                3195

Tyr Gln Ile Ile Lys Gly Ser Asn Phe Gly Met Arg Asn Thr Val
    3200                3205                3210

Ser Gly Pro His Ser Phe Asn Ser Ser Thr Pro Leu Tyr Glu Tyr
    3215                3220                3225

Val Gln Glu Gln Arg Arg
    3230

<210> SEQ ID NO 49
<211> LENGTH: 21
<212> TYPE: DNA
<213> ORGANISM: Artificial Sequence
<220> FEATURE:
<223> OTHER INFORMATION: Artificially synthesized siRNA

<400> SEQUENCE: 49
gcauggaucu uguugcggut t                                              21

<210> SEQ ID NO 50
<211> LENGTH: 25
<212> TYPE: DNA
<213> ORGANISM: Artificial Sequence
<220> FEATURE:
<223> OTHER INFORMATION: Artificially synthesized siRNA

<400> SEQUENCE: 50
```

-continued

```
ggaauuaagu uaggaagaau aautt                                 25

<210> SEQ ID NO 51
<211> LENGTH: 25
<212> TYPE: DNA
<213> ORGANISM: Artificial Sequence
<220> FEATURE:
<223> OTHER INFORMATION: Artificially synthesized siRNA

<400> SEQUENCE: 51
agagugcaua gacaaguaga aacct                                 25

<210> SEQ ID NO 52
<211> LENGTH: 25
<212> TYPE: DNA
<213> ORGANISM: Artificial Sequence
<220> FEATURE:
<223> OTHER INFORMATION: Artificially synthesized siRNA

<400> SEQUENCE: 52
cccuacuuca gaacaauaug gguct                                 25

<210> SEQ ID NO 53
<211> LENGTH: 19
<212> TYPE: DNA
<213> ORGANISM: Mus musculus

<400> SEQUENCE: 53
tgccggagtc gacaatgat                                        19

<210> SEQ ID NO 54
<211> LENGTH: 21
<212> TYPE: DNA
<213> ORGANISM: Mus musculus

<400> SEQUENCE: 54
tggagagcac caagacagac a                                     21

<210> SEQ ID NO 55
<211> LENGTH: 21
<212> TYPE: DNA
<213> ORGANISM: Mus musculus

<400> SEQUENCE: 55
cctggaaagc attgtcactg t                                     21

<210> SEQ ID NO 56
<211> LENGTH: 19
<212> TYPE: DNA
<213> ORGANISM: Mus musculus

<400> SEQUENCE: 56
cggtgtctgg atcatctgg                                        19
```

HORNERIN: A NOVEL NON-VEGF MEDIATED ANGIOGENIC PROTEIN EXPRESSED IN BOTH HUMAN AND MOUSE ANGIOGENIC ENDOTHELIAL CELLS AND HUMAN PANCREATIC CANCER CELLS

CROSS REFERENCE TO RELATED APPLICATION

The presently disclosed subject matter claims the benefit of U.S. Provisional Patent Application Ser. No. 62/731,311, filed Sep. 14, 2018, the disclosure of which is incorporated herein by reference in its entirety.

GRANT STATEMENT

This invention was made with government support under R01CA137071 awarded by the National Institutes of Health. The government has certain rights in the invention.

TECHNICAL FIELD

The presently disclosed subject matter relates to methods for employing hornerin inhibitors as anti-tumor agents. Also provided are methods for increasing the survival of subjects with tumors, for reducing tumor vascularity in subjects, for decreasing tumor leakiness, for increasing tumor oxygenation, for increasing apoptosis of tumor cells and/or the tumor-associated endothelial cells, and for reducing tumor growth.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list all possible combinations of such features.

In various embodiments, the presently disclosed subject matter provides the following: In some embodiments, the presently disclosed subject matter provides methods for treating tumors. In some embodiments, the presently disclosed methods comprise contacting a tumor cell and/or a tumor-associated endothelial cell with an effective amount of a hornerin inhibitor to reduce a biological activity of a hornerin gene product in the tumor cell and/or the tumor-associated endothelial cell, thereby treating the tumor.

In some embodiments, the presently disclosed subject matter provides methods for increasing the survival of a subject with a tumor. In some embodiments, the presently disclosed methods comprise administering to the subject an amount of a hornerin inhibitor effective to reduce a biological activity of a hornerin gene product in a tumor cell and/or a tumor-associated endothelial cell, thereby increasing the survival of the subject relative to a subject to whom the hornerin inhibitor has not been administered.

In some embodiments, the presently disclosed subject matter provides methods for suppressing tumor growth in a subject. In some embodiments, the presently disclosed methods comprise administering to a subject bearing a tumor an effective amount of a composition comprising a hornerin inhibitor, optionally wherein the comprising further comprises a second anti-tumor therapeutic agent.

In some embodiments, the presently disclosed subject matter provides methods for reducing tumor vascularity in a subject. In some embodiments, the presently disclosed methods comprise administering to a subject bearing a tumor an effective amount of a composition comprising a hornerin-binding molecule, optionally a hornerin inhibitor, optionally wherein the comprising further comprises a second anti-tumor therapeutic agent.

In some embodiments of the presently disclosed methods, the effective amount of the hornerin inhibitor is effective to decrease tumor leakiness, increase tumor oxygenation, increase apoptosis of the tumor cell and/or the tumor-associated endothelial cell, reduce growth of the tumor, or any combination thereof in order to treat the tumor.

In some embodiments of the presently disclosed methods, the hornerin inhibitor comprises an siRNA that is designed to hybridize to a hornerin gene product present within the tumor cell and/or the tumor-associated endothelial cell to thereby inhibit a biological activity of the hornerin gene product in the tumor cell and/or the tumor-associated endothelial cell.

In some embodiments of the presently disclosed methods, the tumor cell and/or the tumor-associated endothelial cell is present within a subject, optionally a human subject.

In some embodiments of the presently disclosed methods, the contacting results from administering an effective amount of an anti-hornerin siRNA into the tumor.

In some embodiments, the presently disclosed methods further comprise contacting the tumor and/or administering to the subject one or more additional anti-tumor treatments. In some embodiments, the one or more additional anti-tumor treatments are selected from the group consisting of radiotherapy, chemotherapy, immunotherapy, anti-inflammatory therapy, and combinations thereof. In some embodiments, the one or more additional anti-tumor treatments comprises an anti-VEGF therapy, optionally an anti-VEGFR2 therapy. In some embodiments, the anti-VEGFR2 therapy comprises use of an anti-VEGFR2 antibody or VEGFR2-binding fragment thereof and/or a small molecule anti-VEGFR2 inhibitor. In some embodiments, the anti-VEGFR2 antibody or VEGFR2-binding fragment thereof is selected from the group consisting of ramucirumab or a VEGFR2-binding fragment thereof. In some embodiments, the small molecule anti-VEGFR2 inhibitor is selected from the group consisting of tivozanib (1-[2-chloro-4-(6,7-dimethoxyquinolin-4-yl)oxyphenyl]-3-(5-methyl-1,2-oxazol-3-yl)urea), axitinib (N-Methyl-2-[[3-[(E)-2-pyridin-2-ylethenyl]-1H-indazol-6-yl]sulfanyl]benzamide), lenvatinib (4-[3-Chloro-4-(cyclopropylcarbamoylamino)phenoxy]-7-methoxy-quinoline-6-carboxamide), pazopanib (5-({4-[(2,3-Dimethyl-2H-indazol-6-yl)methylamino]pyrimidin-2-yl}amino)-2-methylbenzenesulfonamide), regorafenib (4-[4-({[4-Chloro-3-(trifluoromethyl)phenyl]carbamoyl}amino)-3-fluorophenoxy]-N-methylpyridine-2-carboxamide hydrate), sorafenib (4-[4-[[4-chloro-3-(trifluoromethyl)phenyl]carbamoylamino]phenoxy]-N-methyl-pyridine-2-carboxamide), sunitinib (N-(2-Diethylaminoethyl)-5-[(Z)-(5-fluoro-2-oxo-1H-indol-3-ylidene)methyl]-2,4-dimethyl-1H-pyrrole-3-carboxamide), vandetanib (N-(4-bromo-2-fluorophenyl)-6-methoxy-7-[(1-methylpiperidin-4-yl)methoxy]quinazolin-4-amine), pharmaceutically acceptable salts thereof, and combinations thereof. In some embodiments, the anti-VEGF therapy comprises use of an anti-VEGF antibody or a VEGF-binding fragment thereof. In some embodiments, the anti-VEGF antibody or VEGF-binding fragment thereof is selected from the group consisting of bevacizumab and ranibizumab.

In some embodiments of the presently disclosed methods, the tumor is a tumor of the pancreas, breast, ovary, colon, or rectum, and/or a metastatic cell derived therefrom characterized by expression of a hornerin gene product in a cell of the tumor and/or an endothelial cell associated therewith.

In some embodiments, the presently disclosed subject matter provides methods for treating diseases, disorders, and/or conditions associated with undesirable hornerin expression. In some embodiments, the methods comprise contacting a cell, tissue, or organ that is characterized by undesirable hornerin expression with an effective amount of a hornerin inhibitor to reduce a biological activity of a hornerin gene product in the cell, tissue, or organ to thereby treat the disease, disorder, or condition. In some embodiments, the disease, disorder, or condition is a cardiovascular disease, disorder, or condition, optionally heart disease.

In some embodiments, the presently disclosed subject matter provides methods for modulating hornerin biological activities in vivo, in vitro, or ex vivo. In some embodiments, methods comprise contacting a hornerin gene product with a modulator, optionally a hornerin-binding molecule, wherein the hornerin biological activity is modulated. In some embodiments, the modulator is a hornerin inhibitor, and the hornerin biological activity is reduced or inhibited. In some embodiments, the modulator is an anti-hornerin antibody or a small molecule or peptide that binds to hornerin to modulate its activity.

In some embodiments, the presently disclosed subject matter also provides compositions comprising one or more hornerin-binding molecules, which in some embodiments are hornerin inhibitors. In some embodiments, the one or more hornerin inhibitors is/are an anti-hornerin antibody, a small molecule, or a peptide, or any combination thereof, which binds to a hornerin gene product to inhibit a biological activity of the hornerin gene product. In some embodiments, the hornerin inhibitor is conjugated to or otherwise associated with an active agent, optionally wherein the active agent is selected from the group consisting of a detectable moiety and a therapeutic moiety. In some embodiments, the composition is a pharmaceutical composition that further comprises at least one pharmaceutically acceptable carrier, diluent, and/or excipient, optionally wherein the pharmaceutical composition is pharmaceutically acceptable for use in a human. In some embodiments, the therapeutic moiety is selected from the group consisting of a chemotherapeutic agent, a toxin, a radiotherapeutic agent, or a combination thereof. In some embodiments, the chemotherapeutic agent is selected from the group consisting of an anti-tumor drug, a cytokine, an anti-metabolite, an alkylating agent, a hormone, methotrexate, doxorubicin, daunorubicin, cytosine arabinoside, etoposide, 5-fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof. In some embodiments, the toxin is selected from the group consisting of Russell's Viper Venom, activated Factor IX, activated Factor X, thrombin, phospholipase C, cobra venom factor, ricin, ricin A chain, *Pseudomonas* exotoxin, diphtheria toxin, bovine pancreatic ribonuclease, pokeweed antiviral protein, abrin, abrin A chain, gelonin, saporin, modeccin, viscumin, volkensin, and combinations thereof. In some embodiments, the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{212}$Pb, $^{212}$Bi, $^{32}$P, $^{33}$P, $^{77}$As, $^{103}$Pb, $^{105}$Rb, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, and $^{197}$Hg. In some embodiments, the hornerin-binding molecule is a peptide comprising an amino acid sequence comprising SLLNRMP (SEQ ID NO: 9).

In some embodiments, the presently disclosed subject matter also provides methods for imaging cells, tissues, and/or organs that express hornerin. In some embodiments, the presently disclosed methods comprise contacting the cell, tissue, and/or organ with a composition as disclosed herein, wherein the active agent is a detectable agent, optionally wherein the detectable agent comprises an imaging agent selected from the group consisting of a paramagnetic ion, a radioactive ion, and a fluorogenic ion. In some embodiments, the radioactive imaging agent is selected from the group consisting of gamma-emitters, positron-emitters and x-ray-emitters. In some embodiments, the radioactive imaging agent is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb and $^{206}$Bi.

The presently disclosed subject matter also provides in some embodiments methods for imaging cells, tissues, and/or organs that expresses hornerin. In some embodiments, the methods comprise contacting the cell, tissue, or organ with a composition as disclosed herein, wherein the active agent is a detectable agent, optionally wherein the detectable agent comprises an imaging agent selected from the group consisting of a paramagnetic ion, a radioactive ion, and a fluorogenic ion.

The presently disclosed subject matter also provides in some embodiments methods for delivering active agents to cells, tissues, and/or organs that expresses hornerin. In some embodiments, the methods comprise contacting the cell, tissue, and/or organ with the composition as disclosed herein, wherein the active agent is selected from the group consisting of a detectable agent and a therapeutic agent. In some embodiments, the detectable agent comprising an imaging agent selected from the group consisting of a paramagnetic ion, a radioactive ion, and a fluorogenic ion. In some embodiments, the therapeutic moiety is selected from the group consisting of a chemotherapeutic agent, a toxin, a radiotherapeutic agent, or a combination thereof.

In some embodiments of the presently disclosed compositions and methods, the hornerin-binding molecule is a peptide comprising an amino acid sequence comprising SLLNRMP (SEQ ID NO: 9).

The presently disclosed subject matter also provides any and all devices, systems, apparatuses, uses, and/or methods shown and/or described expressly or by implication in the information provided herewith, including but not limited to features that may be apparent and/or understood by those of skill in the art.

Thus, it is an object of the presently disclosed subject matter to provide compositions that bind to hornerin present in cells, tissues, and/or organs (including but not limited to tumors and endothelial cells associated therewith), and methods for using the same to image, target, and/or treat those cells, tissues, and/or organs that are characterized by undesirable hornerin expression and associated biological activities.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A: Orthotopic pancreatic tumor section showing co-localization of FITC-labeled "PRH" motif phage clones (green) with PCAM1-positive vessels (red). Relative affinity and fold increase over normal (adjacent, unaffected pancreas vessels) of the "PRH" pool is presented below the image. FIG. 1B: Venn diagram generated after phage-based ELISA and two-way ANOVA analysis that illustrates specificity of phage clone binding to VEGFCM- and/or TCM-treated HUVECs. FIG. 1C: Quantification of the specificity (fold over vehicle control (VC)) for each clone in the Venn diagram. N=6 for each clone. FIG. 1D: Immunoblot detection of hornerin in lysates generated from M13KE (control; lane 1) and PTEM 9 (lane 2) phage pulldowns. FIG. 1E: Representative immunoblot of lysate preparations from VC (lane 1), VEGFCM (lane 2), and TCM (lane 3)-treated HUVECs display the levels of hornerin protein. HSP90 is shown as a loading control. Molecular weight is indicated in kilodaltons (kDa). FIG. 1F: Relative densitometry measured as hornerin fold expression over HSP90. N=3 for each condition. FIG. 1G: Immunofluorescence detection of hornerin (column 1) on non-permeabilized HUVECs following treatment with VC (top row), VEGFCM (middle row), or TCM (bottom row). Wheat germ agglutinin (WGA; column 2) was included in the stain to highlight the plasma membrane. The merged image (column 3) displays hornerin and WGA co-localization. Scale bar=50 µm. Graphs represent the mean±SEM. *P≤0.05 by unpaired two-tailed t-test, treatment compared to vehicle control.

FIG. 2A: ELISA data from PTEM 9 is organized in matrix format, forming the input to two-way ANOVA analysis. Two independent experiments (DS1 and DS2; three replicates in each) were analyzed. Analysis yields three probabilities or P values: fold-over vehicle control (FVC), between data sets (BDS), and an interaction (INT). FIG. 2B: Heatmap showing P values for the comparisons TCM versus VC (left) and VEGFCM versus VC (right). An intensity scale is located below the heatmap. FIG. 2C: ELISA with PTEM 9 clone using two different phage concentrations. Graphs represent average PTEM 9 selective binding over M13KE control phage (no peptide displayed) under the three conditions VC, TCM, and VEGFCM, as determined by ELISA. Samples were run in triplicate for each condition.

FIGS. 3A and 3B. PTEM 9 pulldown. FIG. 3A: Sequences of the 11 identified peptides following MS/MS analysis of the gel band derived from the PTEM 9 pulldown assay. Sequences (boxed in red; SEQ ID NOS: 35, 37, 39, 41, 43, and 45) were overlaid on the amino acid sequence of human hornerin (SEQ ID NO: 34). The percent coverage (MS/MS peptides/hornerin amino acid sequence) is 3.5%. FIG. 3B: The spectra for each of the 11 identified peptides. First panel: SEQ ID NOS: 35 and 36. Second panel: SEQ ID NOs: 37 and 38. Third through fifth panels: SEQ ID NOS: 39 and 40. Sixth and seventh panels: SEQ ID NOs: 41 and 42. Eighth through tenth panels: SEQ ID NOs: 43 and 44. Eleventh panel: SEQ ID NOs: 45 and 46.

FIGS. 4A-4D: Comparative hornerin expression in normal pancreas and resected human PDAC tumors. Images of normal unaffected pancreas and vessels (designated as "V"; FIG. 4A) and PDAC (arrowheads) and associated vessels ("V") following anti-hornerin immunohistochemistry (FIG. 4B). Endothelial cells are marked with black arrows in FIGS. 4A and 4B. FIG. 4C: bar graph showing overall histologic score of tumor endothelium (TE; n=10) and normal pancreas endothelium (NPE; n=5). FIG. 4D: Hornerin was detected by immunohistochemistry in the tumor microarray specimens listed on the x-axis and scored by a certified pathologist. n=2-12/tumor type. Scale bar=100 µm. Graphs represent the mean±SEM. **P<0.005 by unpaired two-tailed t-test.

FIG. 6A: The murine epidermal keratinocyte cell line COCA was treated with either an siRNA targeting murine Hrnr (SEQ ID NO: 49) or a scrambled sequence siRNA (Scr siRNA) for 24 hours, lysed in RIPA buffer, and hornerin protein expression was determined by immunoblot. Beta actin expression was used as a loading control. Image depicts ~60% hornerin knockdown, as determined by densitometry, in Hrnr siRNA treated COCA cells compared to Scr siRNA control cells. FIG. 6B: Hornerin was expressed at near equivalent levels (~90%) in human keratinocytes treated under similar siRNA conditions. Molecular weight is indicated in kilodlatons (kDa). Representative hornerin band indicated by arrow.

FIG. 7A: L3.6pl PDAC cells were injected subcutaneously into the mouse flank and tumor volume was determined upon termination of the experiment (day 13 post implantation). Tumors were injected with either mouse hornerin (Hrnr siRNA; SEQ ID NO: 49) or scrambled control (Scr siRNA) siRNA every other day starting on day 7. Graph displays the mean calculated tumor volume derived from caliper measurements ((tumor length×tumor width$^2$)/2). N=4 tumors/group. FIG. 7B: RNA was isolated from FACS-sorted CD31$^+$ CD45$^-$ tumor endothelial cells and subjected to qPCR. The graph displays the normalized hornerin mRNA transcript levels (reference gene cyclophilin B) from Scr siRNA- and Hrnr siRNA-treated mice. The data points represent sorted endothelial cell sample preparations from two independent experiments run in quadruplicate. N=8 (Scr), 6 (Hrnr siRNA; SEQ ID NO: 49). FIG. 7C: End-point qPCR samples from the above reaction were resolved on a 4% agarose gel and imaged for SYBR green intensity. Gel represents reaction samples following hornerin (Hrnr) and cyclophilin B (Cy. B) primer set amplification, respectively. The predicted size for the hornerin amplicon is 149 base pairs. #bp=number of base pairs in the noted standard bands. FIG. 7D: Representative images of CD34-positive vessels (green) and hornerin (red) in Scr (left) or Hrnr (right) siRNA-injected tumors. Endothelial cells of note are highlighted with arrows. Graphs display the mean expression of hornerin in the CD34+ endothelial cells (left graph) and tumor (right graph). Scale bar=50 μm. Graphs represent mean±SEM. *P<0.05, **P<0.005 by unpaired two-tailed t-test.

FIG. 9A: Representative whole mount Z-stacked images of CD34$^+$ tumor vessels (green) from Scr siRNA (left) and Hrnr siRNA (right) 50 μm tumor sections. FIG. 9B: Graph represents the number of CD34-positive vessels per 0.4 $mm^2$ field. Sections=5 μm, N=16/group (four tumors in each treatment group, four images per tumor). Vessel parameters including vessel volume fraction (FIG. 9C), fractal dimension (FIG. 9D), and radius distribution (FIG. 9E) in pixel units were determined from RAVE analysis of 14 Hrnr siRNA and Scr siRNA whole-mount Z-stacks (four tumors in each treatment group, 3-4 images/tumor). FIG. 9F: Representative images of actin, alpha-2 (ACTA2; red) coverage on CD34$^+$ tumor vessels (green) in tumor sections from Scr siRNA-(left) and Hrnr siRNA-(right) treated mice. Graph represents the ratiometric quantification, as determined by dividing ACTA2-positive pixels by CD34-positive pixels, of 18 Hrnr siRNA sections (four tumors, 3-5 sections per tumor) and 20 Scr siRNA sections (four tumors, five sections per tumor). Scale bars: FIG. 9A=100 μm; FIG. 9F=50 μm. Graphs represent mean±SEM. *P<0.05, **P<0.005 by unpaired two-tailed t-test.

FIG. 10A: Representative flow cytometry dot plots of single cell suspensions generated from sub-cutaneous L3.6pl xenografts. Displayed is the gating scheme utilized to identify $CD31^+$/$CD45^-$ and $CD45^+$ cell populations. From left to right, the gated populations in each plot represent the tumor cell population, single cells in the tumor cell population, viable single cells, and the expression of CD31 and CD45 on viable single cells, respectively. Fluorescence minus one (FMO) plots for CD31 and CD45 are indicated. The gated populations in the stain panel are representative of the $CD31^+$/$CD45^-$ and $CD45^+$ populations that were identified and sorted during FACS. FIGS. 10B: and 10C: Graphs display the percentage of $CD31^+$/$CD45^-$ and $CD45^+$ cells, respectively, out of the total cell population that were analyzed and sorted during FACS. The number of tumor cell suspensions analyzed for each treatment=6 ($CD31^+$/$CD45^-$) and 5 ($CD45^+$). Graphs represent mean+/−SEM. Statistical comparisons by unpaired two-tailed t test.

FIG. 11A: Hrnr siRNA or Scr siRNA were injected into L3.6pl-derived tumors on day 5 post-innoculation. A second round of siRNA treatment was completed three days later, and the tumors were harvested the following day (day 9 post-innoculation), fixed in formalin, embedded in paraffin, and sectioned (5 μm) for immunofluorescence detection of CD34. Representative images of CD34 staining (green) in Scr siRNA (left) and Hrnr siRNA (right) treated tumors. Images displaying CD34$^+$ vasculature in Scr siRNA and Hrnr siRNA tumors were analyzed using RAVE software and the mean radii distribution in pixel units (FIG. 11B), vessel volume fraction (FIG. 11C), and fractal dimension (FIG. 11D) were calculated for each treatment group. Two tumors were analyzed/treatment group; N (images analyzed)=103 (Scr siRNA), 27 (Hrnr siRNA). Scale bar=10 μm. Graphs represent mean+/−SEM. *P≤0.05, P≤0.01, *P≤0.001, ****P≤0.0001 by unpaired two-tailed t test.

FIG. 12A: Representative axial time course images of gadolinium-DTPA (Gd-DTPA) uptake taken pre-siRNA treatment (top row) and 6 days post-treatment (bottom row). The kidney ("K") is labeled for reference. Scr siRNA and Hrnr siRNA tumors demarcated by a white dashed line. FIG. 12B: The concentration of Gd-DTPA (mM) in the tumors was plotted over time. N=7 tumors/treatment group. Injection of Gd-DTPA is signified by arrowhead. FIG. 12C: $K_{trans}$ was calculated for both pre-treatment and post-treatment tumors. N=7 tumors/treatment group. Scale bar=2 mm. Graphs represent mean±SEM. *P<0.05 by unpaired two-tailed t-test.

FIG. 13A: Representative axial time course images of gadolinium-DTPA (Gd-DTPA) uptake in AV-951 treated mice (top row) or mice treated with combination AV-951 and siRNA (bottom row). The kidney ("K") is labeled for reference. Scr siRNA and Hrnr siRNA tumors demarcated by a white dashed line. FIG. 13B: The concentration of Gd-DTPA (mM) in tumors treated with AV-951+ Scr siRNA or AV-951+Hrnr siRNA was plotted over time. FIG. 13C: $K_{trans}$ was calculated for AV-951 only (columns 1 and 2) and AV-951+siRNA (columns 3 and 4). As before, the AV-951 only animals were imaged before treatment with siRNA (columns 1 and 2 pre-siRNA treatment; columns 3 and 4 AV-951 post siRNA treatment). N=5 tumors/treatment group, except AV-951 only (column 2; N=4). Scale bar=2 mm. Graphs represent mean+/−SEM. Statistical comparisons by unpaired two-tailed t test.

FIGS. 14A-14H: Hornerin knockdown in combination with VEGFR inhibition (AV-951) resulted in an enhanced reduction in tumor burden compared to monotherapy. FIG. 14A: Timeline showing points of treatment over the course of the 15-day experiment. On day 5, control and 1.0 mg/kg AV-951-treated tumors were randomly selected to receive either Scr or Hrnr siRNA, resulting in four treatment groups. FIG. 14B: Tumor volume (N=8 tumors/treatment group) on day 5 post implantation in control and AV-951-treated mice. FIG. 14C: Tumor volume was again calculated at day 14 post implantation. N=4 in each treatment group, except control (N=3). See Materials and Methods of the EXAMPLES section below for explanation of outlier exclusion. FIG. 14D: Representative whole-mounted Z-stacked images of CD34$^+$ vessels from each treatment group. FIG. 14E: The number of CD34$^+$ vessels per 0.4 $mm^2$ field was quantified in 20 representative 5 μm sections (four tumors in each treatment group, five images per tumor). Images from 12 whole-mounted Z-stacks (50 μm sections) from each group (three fields per tumor, four tumors in each group) were analyzed by RAVE for radius distribution (FIG. 14F)

and vessel volume fraction (FIG. 14G). FIG. 14H: Ratiometric quantification, determined by dividing ACTA2-positive pixels by CD34-positive pixels, of 12 images from each group (four tumors per group, three sections per tumor). Scale bar=100 µm. Graphs represent mean±SEM. *P<0.05, **P<0.005 by unpaired two-tailed t-test compared to control group.

FIG. 16A: Representative images from Day 15 tumor sections for DAPI (top), Ki67 (middle), and merged image (bottom; Ki67 (red), DAPI (blue)). FIG. 16B: Data presented for Ki67 expression are from the analysis of 10 images/tumor from two tumors/treatment group. FIG. 16C: Representative images from day 15 tumor sections for DAPI (top), cleaved caspase 3 (middle), and merged image (bottom; cleaved caspase 3 (red), DAPI (blue)). FIG. 16D: A minimum number of 10 images/tumor section from four tumor sections/treatment group were analyzed for cleaved caspase 3 expression. Total number of images analyzed/group, N=55 (Scr siRNA/ctrl.), 55 (Hrnr siRNA/ctrl.), 44 (Scr siRNA/AV-951), 51 (Hrnr siRNA/AV-951). Scale bar=50 µm. Graphs represent mean+/−SEM. *P≤0.05, **P≤0.01 by unpaired two tailed t test.

FIG. 17A: Mice were inoculated subcutaneously with $5.0 \times 10^5$ L3.6pl cells in Matrigel/HBSS and treated once daily by oral gavage with VEGFR inhibitor (rows 3 and 4) or vehicle control (rows 1 and 2) starting at day 1 post injection. Scr siRNA (rows 1 and 3) or Hrnr siRNA (rows 2 and 4) solutions were injected into the tumor at day 6 and day 9. Representative images of tumors from each of the four treatment groups at day 5 and day 12 display the blood oxygen saturation levels. A region of interest (ROI; white box) of equivalent dimensions (area) was defined and then applied in a blinded manner to each image. FIG. 17B: Blood oxygen saturation levels were determined for each treatment group by analyzing the ROIs from four tumors/group. Scale bar=200 µm. Graphs represent mean±SEM. *P≤0.05, **P≤0.01 by unpaired two-tailed t-test.

FIG. 18A: Heatmap of the difference in expression of TCM compared to VC media as measured by a Human Angiogenesis Antibody Array (Affymetrix, Santa Clara, CA, USA). "neg" refers to a negative control built into the assay by the manufacturer. FIG. 18B: Representative western blot of the lysates of HUVECs treated with the top 5 differentially expressed growth factors. HSP90 is presented as a loading control. The graph displays the relative densitometry of 2 separate experiments measured as fold HRNR expression over HSP90. Bar represent the mean value. FIG. 18C: HUVECs were plated at a density of $0.15 \times 10^6$ cells/well in 6 well cluster plates in complete media, starved of EGF for 14 hours, and subsequently treated with EGF at the indicated concentrations. Hornerin expression was determined by immunoblot after 24 hours treatment. Beta actin was utilized as a loading control. FIG. 18D: L3.6pl cells were plated in complete media in 6 well cluster plates at a density of $0.2 \times 10^6$ cells/well. On day 2, the cells were replenished with serum free media and serum starved overnight, upon which vehicle control or EGF was added at the indicated concentrations. The cells were subsequently lysed in RIPA buffer at 48 hours and lysate preparations were subjected to immunoblot detection of hornerin. Beta actin is presented as a control. FIG. 18E: Human keratinocytes were plated at a density of $0.1 \times 10^6$ cells/well in 6 well plates and treated on day 2 with either EGF or 2 mM $CaCl_2$. Lysate preparations were generated 48 hours post-treatment for immunoblot detection of hornerin. Beta actin is presented as a control. Molecular weight is indicated in kiloDaltons (kDa).

BRIEF DESCRIPTION OF THE SEQUENCE LISTING

SEQ ID NOs: 1-30 are the amino acid sequences of exemplary peptides that bind to hornerin gene products to inhibit one or more biological activities thereof.

SEQ ID NOs: 31 and 32 are nucleotide sequences of oligonucleotide primers that can be employed together to amplify inserts in M13 phage.

SEQ ID NO: 33 is a nucleotide sequence of an exemplary human hornerin gene product. It corresponds to Accession No. NM_001009931.2 of the GENBANK® biosequence database.

SEQ ID NO: 34 is an amino acid sequence of an exemplary human hornerin gene product. It corresponds to Accession No. NP_001009931.1 of the GENBANK® biosequence database.

Figures 1, 3B:
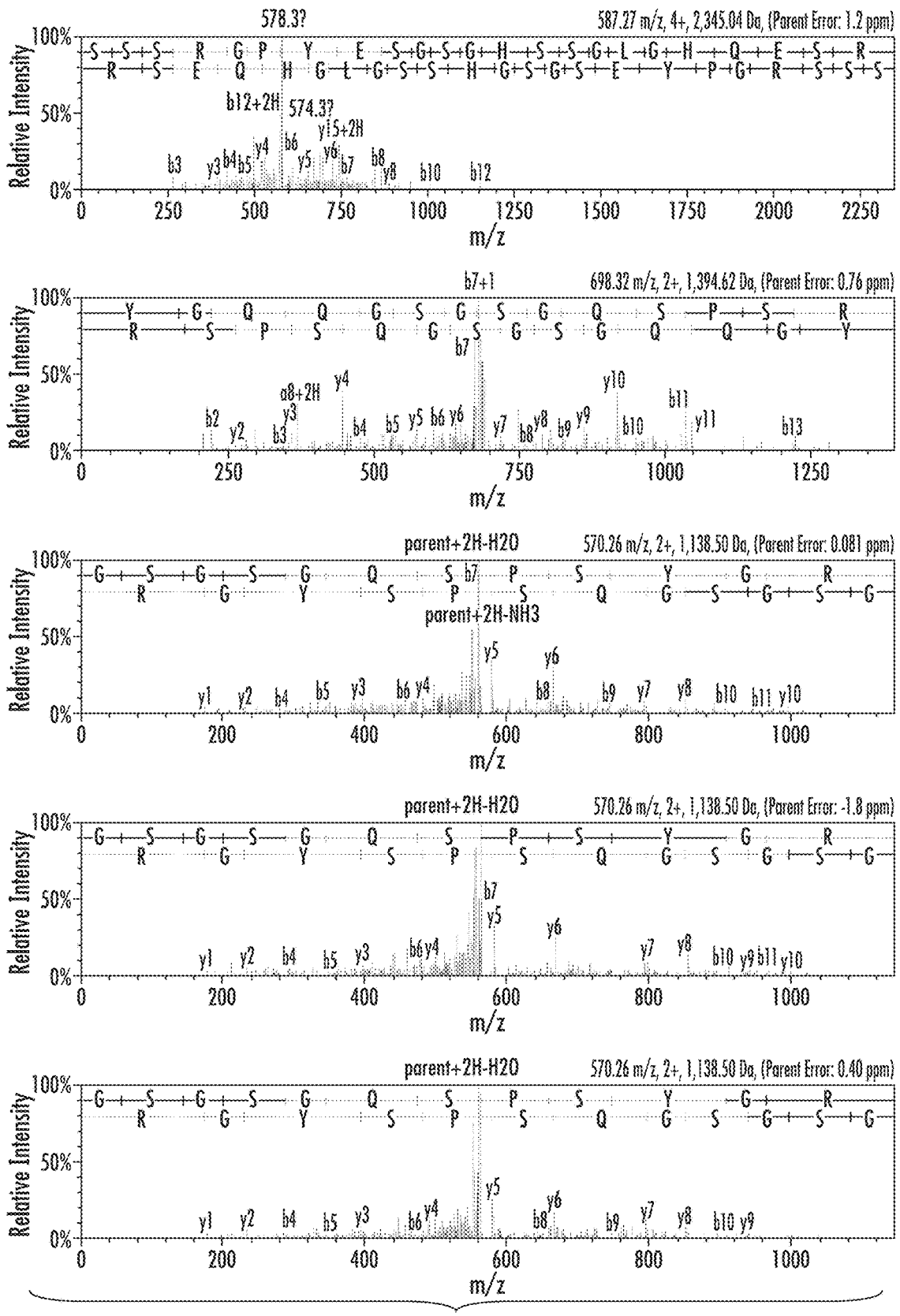
Figures 2, 3B:
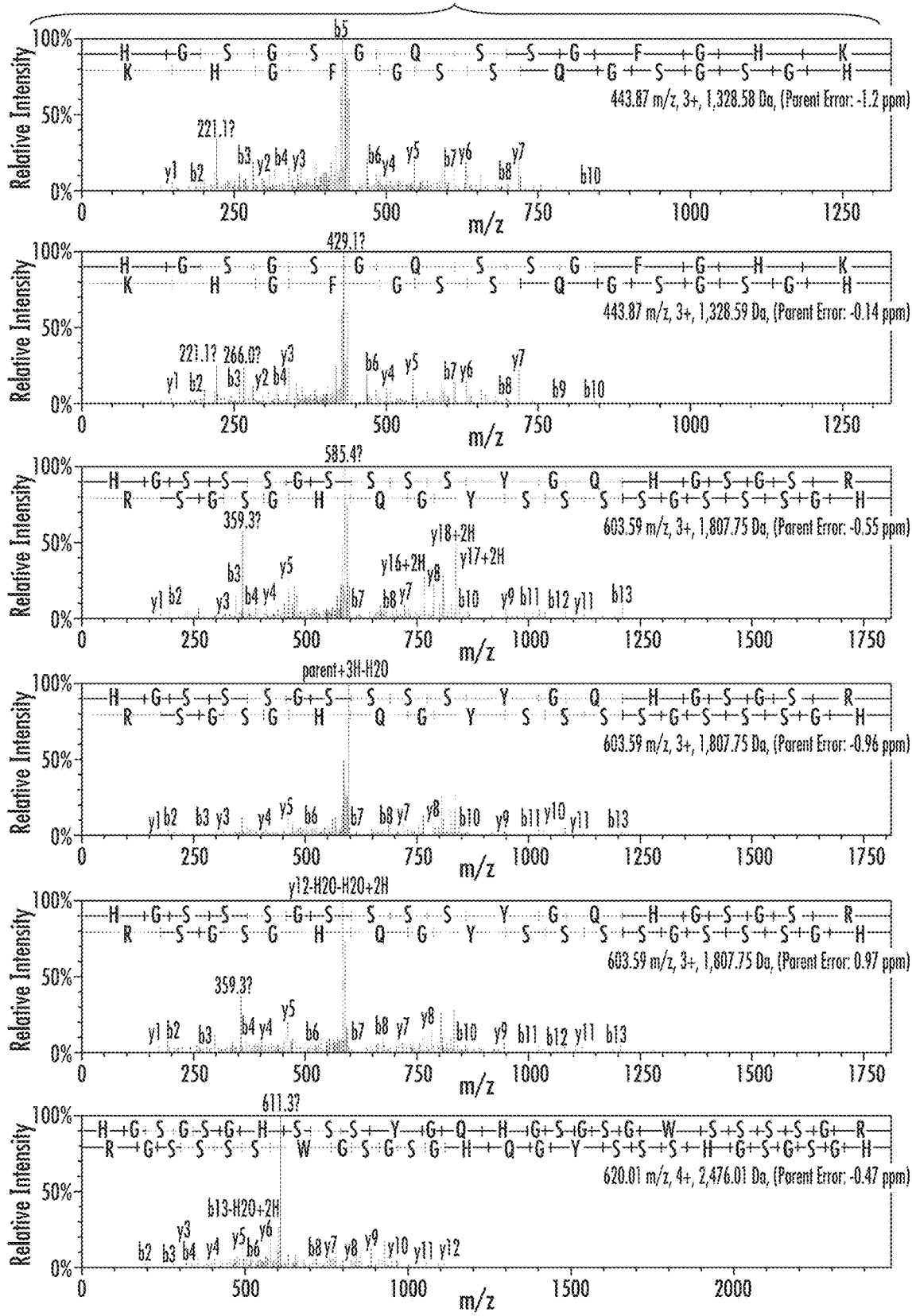

SEQ ID NOs: 35-46 are the amino acid sequences of certain peptides identified following MS/MS analysis as described in FIG. 3A and employed in generating the spectra for the identified peptides showin in FIG. 3B.

SEQ ID NOs: 47 is a nucleotide sequence of an exemplary mouse hornerin gene product. It corresponds to Accession No. NM_133698.2 of the GENBANK® biosequence database SEQ ID NO: 48 is an amino acid sequence of an exemplary mouse hornerin gene product. It corresponds to Accession No. NP_598459.2 of the GENBANK® biosequence database.

SEQ ID NOs: 49-52 are the nucleotide sequences of four exemplary mouse Hrnr siRNAs.

SEQ ID NOs: 53 and 54 are the nucleotide sequences of two exemplary oligonucleotides that can be used together to amplify a mouse cyclophilin B gene product.

SEQ ID NOs: 55 and 56 are the nucleotide sequences of two exemplary oligonucleotides that can be used together to amplify a mouse hornerin gene product.

DETAILED DESCRIPTION

The generation and maintenance of a tumor vascular network is essential for tumor growth and provides a conduit for tumor cell metastasis. In their seminal paper, Hanahan & Weinberg, 2000 listed sustained angiogenesis as one of the original hallmarks of cancer. Research in the intervening years has bolstered the significance of this process and necessitated its inclusion in their follow-up paper a decade later (Hanahan & Weinberg, 2011). As vessels provide the fuel for a growing tumor, anti-angiogenic therapies designed to impede the rapid, dysregulated propagation of vessels or enhance endothelial cell death have been proposed and at times implemented in clinic. These are commonly combined with anticancer cell therapies, resulting in an overall strategy that targets critical signaling pathways in different cell types that comprise the tumor microenvironment (Kindler et al., 2011; Lang et al., 2013).

The discovery of vascular endothelial growth factor (VEGF), originally called vascular permeability factor, in 1983 (Senger et al., 1983) dramatically increased the knowledge of angiogenesis in many fields, including tumor angiogenesis. Since it is extensively studied and highly overexpressed in cancer as well as other pathologies, the VEGF pathway was a natural initial target when developing anti-angiogenesis therapies. Anti-VEGF therapies include small molecule inhibitors, VEGF receptor blocking antibodies, and VEGF traps, which mimic the receptor-binding site and sequester VEGF from its receptor. In a review of anti-angiogenic therapies in pancreatic cancer, Whipple & Korc, 2006 listed 12 anti-angiogenic therapies that are in use for this type of cancer alone. When browsing the list, it is striking that 10 of those 12 therapies target the VEGF pathway. Anti-angiogenic (mostly anti-VEGF) therapies have achieved success pre-clinically and clinically, however, as is common with monotherapies, tumor resistance and recurrence is a major problem.

One hypothesis for the lack of success could be the presence of compensatory or redundant pathways. Compensatory pathways are well established in tumor therapy research; consequently clinical trials devoted to synergistic combinations of drugs have proliferated (Johnston et al., 2009; Kaufman et al., 2009; Baselga et al., 2012). Combinatorial approaches involving non-redundant signaling pathways show great promise, as they have the ability to overcome acquired resistance to chemotherapy (Al-Lazikani et al., 2012). A synergistic/additive approach, one involving both the VEGF pathway and another important pathway, could provide the positive results that anti-angiogenic therapies should theoretically produce.

Therefore, to identify non-VEGF-mediated tumor angiogenic factors, a phage display functional proteomics approach that combined an in vivo phage screen in tumor-bearing animals with an in vitro screen to exclude clones that bound to VEGF-treated cells was employed. Binding partner identification from this screen revealed the protein hornerin, which to this point had been studied predominantly in the skin epithelium (Makino et al., 2001; Takaishi et al., 2005; Wu et al., 2009; Henry et al., 2011). Hornerin was further validated in human umbilical vein endothelial cells (HUVECs) as a non-VEGF regulated protein. While confirming hornerin expression in tumor-associated endothelial cells in resected human pancreatic ductal adenocarcinoma (PDAC) samples, it was discovered that hornerin is also expressed in PDAC. Further exploration identified several other tumor types that express hornerin, including renal cell carcinoma (RCC) and prostate adenocarcinoma. A functional role of hornerin was affirmed, as in vivo-specific knockdown of hornerin in tumor associated endothelial cells resulted in decreased tumor burden along with alterations in vessel parameters as measured by vessel radius, vessel volume fraction, and fractal dimension. In addition, magnetic resonance imaging (MRI) of tumors with vessels with decreased hornerin expression revealed a decrease in vascular leakiness. Finally, hornerin knockdown combined with VEGF inhibition produced additive tumor volume and angiogenesis abatement, providing further evidence that compensatory pathways exist in tumor-associated endothelial cells.

The discovery of elevated hornerin expression in tumor vasculature, the functional consequences of hornerin targeted knockdown on tumor vascularity and growth, and the additive effect of hornerin depletion with VEGFR signaling inhibition directs the potential creation of a novel anti-angiogenesis strategy that targets multiple signaling pathways in tumor endothelial cells.

The presently disclosed subject matter will be now be described more fully hereinafter with reference to the accompanying Figures and EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed and claimed subject matter.

Following long-standing patent law convention, the terms "a", "an", and "the" refer to "one or more" when used in this application, including in the claims. For example, the phrase "an antibody" refers to one or more antibodies, including a plurality of the same antibody. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and/or other inactive agents can and likely would be present in such a pharmaceutical composition, and are encompassed within the nature of the phrase "consisting essentially of".

With respect to the terms "comprising", "consisting of", and "consisting essentially of", where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

As used herein, the terms "condition", "disease condition", "disease", "disease state", and "disorder" refer to physiological states in which diseased cells can be targeted with the hornerin inhibitors and/or the methods of using the same of the presently disclosed subject matter.

As used herein, the term "hornerin" (abbreviated HRNR or hrnr) refers to a human gene, locus, or gene product as set forth in Accession Nos. NM_001009931.2 (cDNA; SEQ ID NO: 33) and NP_001009931.1 (encoded protein; SEQ ID NO: 34) in the GENBANK® biosequence database, as well as orthologs thereof. In humans, the hornerin locus is present on chromosome 1 and corresponds to the reverse-complement of nucleotides 152,212,076-152,224,196 of Accession No. NC_000001.11 in the GENBANK® biosequence database. An exemplary, non-limiting ortholog of the human horerin gene is the murine hornerin gene that corresponds to Accession Nos. NM_133698.2 (cDNA; SEQ ID NO: 282) and NP_598459.2 (encoded protein; SEQ ID NO: 283) in the GENBANK® biosequence database. The murine hornerin gene is located on chromosome 3, and the genetic locus corresponds to nucleotides 93,319,541-93,333,572 of Accession No. NC_000069.6 in the GENBANK® biosequence database. Other names for the hornerin gene, locus, and gene products include FLG3, S100A16, and S100a18.

As used herein, the term "mammal" refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

As used herein, the phrase "hornerin-associated cancer" is a tumor or cancer, or a cell therefrom including but not limited to endothelial cells therefrom, in which a hornerin gene product is expressed (in some embodiments, overexpressed).

The term "polynucleotide" as used herein includes but is not limited to DNA, RNA, complementary DNA (cDNA), messenger RNA (mRNA), ribosomal RNA (rRNA), small hairpin RNA (shRNA), small nuclear RNA (snRNA), short nucleolar RNA (snoRNA), microRNA (miRNA), genomic DNA, synthetic DNA, synthetic RNA, and/or tRNA.

As used herein, the phrases "single chain variable fragment", "single-chain antibody variable fragments", and "scFv" antibodies refer to forms of antibodies comprising the variable regions of only the heavy and light chains, connected by a linker peptide.

The term "subject" as used herein refers to a member of any invertebrate or vertebrate species. Accordingly, the term "subject" is intended to encompass in some embodiments any member of the Kingdom Animalia including, but not limited to the phylum Chordata (e.g., members of Classes Osteichythyes (bony fish), Amphibia (amphibians), Reptilia (reptiles), Ayes (birds), and Mammalia (mammals), and all Orders and Families encompassed therein.

The compositions and methods of the presently disclosed subject matter are particularly useful for warm-blooded vertebrates. Thus, in some embodiments the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

As used herein, the phrase "target cell" refers to any cell that is associated with a disease, disease state, or disorder that can be targeted by the compositions and methods of the presently disclosed subject matter (including but not limited to tumor cells and tumor-associated endothelial cells). In some embodiments, a target cell is a tumor cell, a cancer cell, or a tumor-associated endothelial cell that expresses a hornerin gene product.

As used herein, the phrase "therapeutic agent" refers to an agent that is used to, for example, treat, inhibit, prevent, mitigate the effects of, reduce the severity of, reduce the likelihood of developing, slow the progression of, and/or cure, a disease or disorder.

The terms "treatment" and "treating" as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented.

As used herein, the term "tumor" refers to any neoplastic cell growth and/or proliferation, whether malignant or benign, and all pre-cancerous and cancerous cells and tissues. The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas, and meningiomas). As used herein, the terms "cancer and "tumor" are also intended to refer to multicellular tumors as well as individual neoplastic or pre-neoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

As used herein, the phrase "tumor-associated" refers to a disease, disorder, condition, status, antigen, epitope, or glycosylation state that is primarily or secondarily the result of the presence of a tumor or cancer or a cell's status as being a tumor cell or a cancer cell. Similarly, a "tumor-associated endothelial cell" refers to an endothelial cell or a plurality thereof (e.g., a blood vessel) that provides one or more nutrients to the tumor or to a cell thereof.

All genes, gene names, and gene products disclosed herein are intended to correspond to homologs and/or orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the gene products presented in Accession Nos: NM_001009931.2 and NP_001009931.1 of the GENBANK® biosequence database, the human nucleotide and amino acid sequences disclosed therin are intended to encompass homologous and orthologous genes and gene products from other animals including, but not limited to other mammals, fish, amphibians, reptiles, and birds.

II. Compositions Comprising Hornerin Inhibitors and/or Other Hornerin-Binding Molecules In some embodiments, the presently disclosed subject matter provides compositions comprising one or more hornerin modulators including but not limited to hernerin inhibitors. Exemplary hornerin modulators/inhibitors include but are not limited to anti-hornerin antibodies (including fragments and derivatives thereof that bind to hornerin), small molecules, and/or peptides, or any combination thereof, which bind to a hornerin gene product to inhibit a biological activity of the hornerin gene product. Exemplary hornerin-binding peptides are disclosed herein (see e.g., Table 1). Other exemplary hornerin-binding peptides are disclosed in PCT International Patent Application Publication No. WO 2016/205397 and associated U.S. National Stage patent application Ser. No. 15/737,047 (published as U.S. Patent Application Publication No. 2018/0360755), all of which are incorporated herein by reference in their entireties.

TABLE 1

Exemplary Hornerin-binding Peptides

| Clone | Sequence | SEQ ID NO: |
|---|---|---|
| PTEM 1 | EDRANRQ | 1 |
| PTEM 2 | SAPSSKN | 2 |
| PTEM 3 | TSLSMPS | 3 |
| PTEM 4 | LPTPPYA | 4 |
| PTEM 5 | MTSQHPK | 5 |
| PTEM 6 | NQLPLHA | 6 |
| PTEM 7 | TTVMGNL | 7 |
| PTEM 8 | AMLPYTF | 8 |
| PTEM 9 | SLLNRMP | 9 |
| PTEM 10 | GKPMPPM | 10 |
| PTEM 11 | VAHQLSR | 11 |
| PTEM 12 | HAIYPRH | 12 |
| PTEM 13 | IPTLPSS | 13 |
| PTEM 14 | EPLQLKM | 14 |
| PTEM 15 | SHGNWWR | 15 |
| PTEM 16 | LHRPYST | 16 |
| PTEM 17 | HAIYPRH | 17 |
| PTEM 18 | QILAFNS | 18 |
| PTEM 19 | SAPSSKN | 19 |
| PTEM 20 | TLHSLPP | 20 |
| PTEM 21 | WTITKHP | 21 |
| PTEM 22 | SPTQPKS | 22 |
| PTEM 23 | GKVQAQS | 23 |
| PTEM 24 | GRPHSAL | 24 |
| PTEM 25 | ATLTHPP | 25 |
| PTEM 26 | STPIQQP | 26 |
| PTEM 27 | SLYKWTI | 27 |
| PTEM 28 | ANTTPRH | 28 |
| PTEM 29 | HTAPNFA | 29 |
| PTEM 30 | ANSTPPI | 30 |

In some embodiments, the hornerin inhibitor is conjugated to or otherwise associated with an active agent, optionally wherein the active agent is selected from the group consisting of a detectable moiety and a therapeutic moiety. In some embodiments, the composition is a pharmaceutical composition that further comprises at least one pharmaceutically acceptable carrier, diluent, and/or excipient, optionally wherein the pharmaceutical composition is pharmaceutically acceptable for use in a human. In some embodiments, the therapeutic moiety is selected from the group consisting of a chemotherapeutic agent, a toxin, a radiotherapeutic agent, or a combination thereof. In some embodiments, the chemotherapeutic agent is selected from the group consisting of an anti-tumor drug, a cytokine, an anti-metabolite, an alkylating agent, a hormone, methotrexate, doxorubicin, daunorubicin, cytosine arabinoside, etoposide, 5-fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, etoposide, mithramycin, doxorubicin, daunomycin, vinblastine, neocarzinostatin, macromycin, α-amanitin, and combinations thereof. In some embodiments, the toxin is selected from the group consisting of Russell's Viper Venom, activated Factor IX, activated Factor X, thrombin, phospholipase C, cobra venom factor, ricin, ricin A chain, *Pseudomonas* exotoxin, diphtheria toxin, bovine pancreatic ribonuclease, pokeweed antiviral protein, abrin, abrin A chain, gelonin, saporin, modeccin, viscumin, volkensin, and combinations thereof. In some embodiments, the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$Bi, $^{32}$P, $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Lu, $^{191}$Os, $^{193M}$Pt, and $^{197}$Hg.

In some embodiments, a composition of the presently disclosed subject matter comprises the presently disclosed antibodies, fragments, and/or derivatives thereof and one or more pharmaceutically acceptable carriers and/or excipients. In some embodiments, the carrier(s) and/or excipient(s) is pharmaceutically acceptable for use in humans. Suitable formulations include aqueous and non-aqueous sterile injection solutions which can contain anti-oxidants, buffers, bacteriostats, bactericidal antibiotics, and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS) in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used.

The compositions of the presently disclosed subject matter can also comprise an active agent, wherein the active agent comprises a therapeutic moiety, a diagnostic moiety, and/or a biologically active moiety. As used herein, the phrase "active agent" thus refers to a component of the presently disclosed compositions that provides a therapeutic benefit to a subject, permits visualization of cells or tissues in which the compositions of the presently disclosed subject matter accumulate, detection of epitopes to which the presently disclosed antibodies, fragments, and derivatives bind, and/or enhances any of these activities. In some embodiments, an active agent of the presently disclosed subject matter is selected from the group consisting of a radioactive molecule (including, but not limited to radionuclides and radioisotopes), a sensitizer molecule, an imaging agent or other detectable agent, a toxin, a cytotoxin, an anti-angiogenic agent, an anti-tumor agent, a chemotherapeutic agent, an immunomodulator, a cytokine, a reporter group, and combinations thereof. It is understood that these categories are not intended to be mutually exclusive, as some radioactive molecules, for example, are also chemotherapeutic agents, some immunomodulators are cytokines, etc.

In some embodiments, an active agent comprises a chemotherapeutic. Various chemotherapeutics are known to one of ordinary skill in the art, and include, but are not limited to alkylating agents such as nitrogen mustards (e.g., Chlorambucil, Cyclophosphamide, Isofamide, Mechlorethamine, Melphalan, Uracil mustard), aziridines (e.g., Thiotepa), methanesulfonate esters (e.g., Busulfan), nitroso ureas (e.g., Carmustine, Lomustine, Streptozocin), platinum complexes (e.g., Cisplatin, Carboplatin), and bioreductive alkylators (e.g., Mitomycin C, Procarbazine); DNA strand breaking agents (e.g., Bleomycin); DNA topoisomerase I inhibitors (e.g., camptothecin and derivatives thereof including, but not limited to 10-hydroxycamptothecin), DNA topoisomerase II inhibitors (e.g., Amsacrine, Dactinomycin, Daunorubicin, Doxorubicin, Idarubicin, Mitoxantrone, Etoposide, Teniposide, Podophyllotoxin); DNA minor groove binders (e.g., Plicamycin); anti-metabolites such as folate antagonists (e.g., Methotrexate and trimetrexate), pyrimidine antagonists (e.g., Fluorouracil, Fluorodeoxyuridine, CB3717, Azacytidine, Cytarabine, Floxuridine), purine antagonists (e.g., Mercaptopurine, 6-Thioguanine, Fludarabine, Pentostatin), sugar modified analogs (e.g., Cyctrabine, Fludarabine), and ribonucleotide reductase inhibitors (e.g., Hydroxyurea); tubulin interactive agents (e.g., Vincristine, Vinblastine, Paclitaxel); adrenal corticosteroids (e.g., Prednisone, Dexamethasone, Methylprednisolone, Prednisolone); hormonal blocking agents such as estrogens and related compounds (e.g., Ethinyl Estradiol, Diethylstilbesterol, Chlorotrianisene, Idenestrol), progestins (e.g., Hydroxyprogesterone caproate, Medroxyprogesterone, Megestrol), androgens (e.g., Testosterone, Testosterone propionate; Fluoxymesterone, Methyltestosterone), leutinizing hormone releasing hormone agents and/or gonadotropin-releasing hormone antagonists (e.g., Leuprolide acetate; Goserelin acetate), anti-estrogenic agents (e.g., Tamoxifen), anti-androgen agents (e.g., Flutamide), and anti-adrenal agents (e.g., Mitotane, Aminoglutethimide). Other chemotherapeutics include, but are not limited to Taxol, retinoic acid and derivatives thereof (e.g., 13-cis-retinoic acid, all-trans-retinoic acid, and 9-cis-retinoic acid), sulfathiazole, mitomycin C, mycophenolic acid, sulfadiethoxane, and gemcitabine (4-amino-1-(2-deoxy-2,2-difluoro-β-D-erythro-pentofuranosyl)pyrimidin-2(1H)-on-2',2'-difluoro-2'-deoxycytidine).

In some embodiments, an active agent comprises an anti-angiogenic agent. Various anti-angiogenic agents are known to one of ordinary skill in the art, and include, but are not limited to inhibitors and/or antagonists of vascular endothelial growth factor (VEGF) family and its receptors (e.g., Bevacizumab and other anti-vascular endothelial growth factor (VEGF) antibodies) and neuropilin-1 antagonists.

In some embodiments, the compositions of the presently disclosed subject matter can be used with additional adjuvants and/or immunomodulators. As used herein, the phrases "immune modulating agent" and "immunomodulating agent" refer to molecules cable of modulating immune responses. Exemplary immunomodulators include, but are not limited to cytokines (including, but not limited to, the cytokines IFN-α, IFN-γ, IL-2, IL-4, IL-6, TNF, and other cytokines affecting immune cells), CpG oligodeoxynucleotides (CpG ODN), which function as a dendritic cell activator (Rothenfusser et al., 2002), and the immunomodulators set forth in Table 2.

TABLE 2

Exemplary Immunomodulators*

| Target | Modulators |
|---|---|
| indoleamine 2,3-dioxygenase (IDO) | 1MT; MTH-Trp |
| Arginase (ARG) | ABH; BEC |
| inducible nitric oxide synthase (iNOS) | L-NMMA |
| ARG/iNOS | NCX-4016 |
| COX-2 | Celecoxib; Rofecoxib |
| EP2/EP4 | CP-533536 |
| TGFβRI | SB-505124; SD-505124; LY580276 |
| JAK/STAT | JSI-124; CPA-7 |
| VEGFR1/FLT1 | SU5416; AG-013736 |
| CCR4 | IC-487892 |
| CXCR4 | AMD3100 |
| CCR2 | INCB3344 |

*see Muller & Scherle, 2006 and references therein. MTH-TRP: methyl-thiohydantoin-tryptophan; ABH: 2(S)-amino-6-boronohexanoic acid; BEC: S- (2-boronoethyl)-L-cysteine; L-NMMA: L-NG-monomethyl arginine; NCX- 4016: nitroaspirin; see Emanueli et al., 2004; CP-533536: see Cameron et al., 2009; SB-505124: see DeCosta Byfield et al., 2004; SD-505124: see Muller & Scherle, 2006; LY580276: see Sawyer et al., 2004; JSI-124: see Blaskovich et al., 2003; CPA-7: see Littlefield et al., 2008; SU5416: see Fong et al., 1999; AG-013736 (Axitinib): see Rugo et al., 2005; IC-487892: ICOS Corp., Bothell, WA, USA; AMD3100: see Donzella et al., 1998.

For therapeutic applications, a therapeutically effective amount of a composition of the presently disclosed subject matter is administered to a subject. A "therapeutically effective amount" is an amount of a composition sufficient to produce a measurable biological tumor response (such as, but not limited to an immunostimulatory, an anti-angiogenic response, a cytotoxic response, tumor regression, and/or tumor growth inhibition). Actual dosage levels of active ingredients in a composition of the presently disclosed subject matter can be varied so as to administer an amount of the active agent(s) that is effective to achieve the desired therapeutic response for a particular subject. The selected dosage level will depend upon a variety of factors including the activity of the composition, formulation, the route of administration, combination with other drugs or treatments, tumor size and longevity, and the physical condition and prior medical history of the subject being treated. In some embodiments of the presently disclosed subject matter, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the presently disclosed subject matter is administered to a subject. A "detectable amount", as used herein to refer to a composition, refers to a dose of such a composition that the presence of the composition can be determined in vivo or in vitro. A detectable amount will vary according to a variety of factors, including but not limited to chemical features of the composition being labeled, the detectable label, the labeling methods, the method for imaging and parameters related thereto, metabolism of the labeled drug in the subject, the stability of the label (including, but not limited to the half-life of a radionuclide label), the time elapsed following administration of the composition prior to imaging, the route of administration, the physical condition and prior medical history of the subject, and the size and longevity of the tumor or suspected tumor. Thus, a detectable amount can vary and can be tailored to a particular application. After study of the present disclosure, it is within the skill of one in the art to determine such a detectable amount.

As used herein, the terms "detectable moiety", "detectable label", and "detectable agent" refer to any molecule that can be detected by any moiety that can be added to a peptide and/or an antibody, or a fragment or derivative thereof such as but not limited to a hornerin-binding peptide or polypeptide, that allows for the detection of the antibody, fragment, or derivative in vitro and/or in vivo. Representative detectable moieties include, but are not limited to, chromophores, fluorescent moieties, enzymes, antigens, groups with specific reactivity, chemiluminescent moieties, and electrochemically detectable moieties, etc. In some embodiments, the antibodies are biotinylated.

In some embodiments, a detectable moiety comprises a fluorophore. Any fluorophore can be employed with the compositions of the presently disclosed subject matter, provided that the conjugation of fluorophore results in a composition that is detectable either in vivo (e.g., after administration to a subject) and/or in vitro, and further does not negatively impact the ability of the antibody, or the fragment or derivative thereof, to bind to its epitope. Representative fluorophores include, but are not limited to 7-dimethylaminocoumarin-3-carboxylic acid, dansyl chloride, nitrobenzodiazolamine (NBD), dabsyl chloride, cinnamic acid, fluorescein carboxylic acid, Nile Blue, tetramethylcarboxyrhodamine, tetraethylsulfohodamine, 5-carboxy-X-rhodamine (5-ROX), and 6-carboxy-X-rhodamine (6-ROX). It is understood that these representative fluorophores are exemplary only, and additional fluorophores can also be employed. For example, there the ALEXA FLUOR® dye series includes at least 19 different dyes that are characterized by different emission spectra. These dyes include ALEXA FLUOR® 350, 405, 430, 488, 500, 514, 532, 546, 555, 568, 594, 610, 633, 635, 647, 660, 680, 700, and 750 (available from Invitrogen Corp., Carlsbad, California, USA), and the choice of which dye to employ can be made by the skilled artisan after consideration of the instant specification based on criteria including, but not limited to the chemical compositions of the specific ALEXA FLUOR®, whether multiple detectable moieties are to be employed and the emission spectra of each, the detection technique to be employed, etc.

In some embodiments, a detectable moiety comprises a cyanine dye. Non-limiting examples of cyanine dyes that can be conjugated to the antibodies, fragments, and/or derivatives of the presently disclosed subject matter include the succinimide esters Cy5, Cy5.5, and Cy7, supplied by Amersham Biosciences (Piscataway, NJ, USA).

In some embodiments, a detectable moiety comprises a near infrared (NIR) dye. Non-limiting examples of near infrared dyes that can be conjugated to the antibodies, fragments, and/or derivatives of the presently disclosed subject matter include NIR641, NIR664, NIT7000, and NIT782.

In some embodiments, the biotinylated antibodies are detected using a secondary antibody that comprises an avidin or streptavidin group and is also conjugated to a fluorescent label including, but not limited to Cy3, Cy5, Cy7, and any of the ALEXA FLUOR®® series of fluorescent labels available from INVITROGEN™ (Carlsbad, California, USA). In some embodiments, the antibody, fragment, or derivative thereof is directly labeled with a fluorescent label and cells that bind to the antibody are separated by fluorescence-activated cell sorting. Additional detection strategies are known to the skilled artisan.

For diagnostic applications (including but not limited to detection applications and imaging applications), the antibodies of the presently disclosed subject matter can be labeled with a detectable moiety. The detectable moiety can be any one that is capable of producing, either directly or indirectly, a detectable signal. For example, a detectable moiety can be a radioisotope, such as but not limited to $^3$H, $^{14}$C, $^{32}$P, $^{35}$S, $^{125}$I, or $^{131}$I; a fluorescent or chemiluminescent compound such as but not limited to fluorescein isothiocyanate, rhodamine, or luciferin; or an enzyme, such as but not limited to alkaline phosphatase, β-galactosidase, or horseradish peroxidase.

The presently disclosed subject matter further provides methods for diagnosing a tumor, wherein a tumor sample or biopsy is evaluated in vitro. In some embodiments, a targeting ligand of the presently disclosed subject matter comprises a detectable label such as a fluorescent label, an epitope tag, or a radioactive label, each described briefly herein below.

Fluorescence. Any detectable fluorescent dye can be used, including but not limited to FITC (fluorescein isothiocyanate), FLUOR X™, ALEXA FLUOR®, OREGON GREEN®, TMR (tetramethylrhodamine), ROX (X-rhodamine), TEXAS RED®, BODIPY® 630/650, Cy5 (available from Amersham Pharmacia Biotech of Piscataway, NJ, USA, or from Molecular Probes Inc. of Eugene, OR, USA), and mKATE/mKATE2 (see e.g., U.S. Pat. No. 8,481,307; Wang et al., 2011.

A fluorescent label can be detected directly using emission and absorbance spectra that are appropriate for the particular label used. Common research equipment has been developed for in vitro detection of fluorescence, including instruments available from GSI Lumonics (Watertown, MA, USA) and Genetic MicroSystems Inc. (Woburn, MA, USA). Most of the commercial systems use some form of scanning technology with photomultiplier tube detection. Criteria for consideration when analyzing fluorescent samples are summarized by Alexay et al., 1996.

Detection of an Epitope Tag. If an epitope label has been used, a protein or compound that binds the epitope can be used to detect the epitope. A representative epitope label is biotin, which can be detected by binding of an avidin-conjugated fluorophore, for example avidin-FITC. Alternatively, the label can be detected by binding of an avidin-horseradish peroxidase (HRP) streptavidin conjugate, followed by colorimetric detection of an HRP enzymatic product. The production of a colorimetric or luminescent product/conjugate is measurable using a spectrophotometer or luminometer, respectively.

Autoradiographic Detection. In the case of a radioactive label (e.g., $^{131}$I or $^{99m}$Tc) detection can be accomplished by conventional autoradiography or by using a phosphorimager as is known to one of skill in the art. An exemplary, non-limiting autoradiographic method employs photostimulable luminescence imaging plates (Fuji Medical Systems of Stamford, CT, USA). Briefly, photostimulable luminescence is the quantity of light emitted from irradiated phosphorous plates following stimulation with a laser during scanning. The luminescent response of the plates is linearly proportional to the activity (Amemiya et al., 1988; Hallahan et al., 2001a; Hallahan et al., 2001b).

Any method known in the art for conjugating a peptide or an antibody to a detectable moiety can be employed (see e.g., Hunter et al., 1962; David et al., 1974; Pain et al., 19819; Nygren, 1982).

Drug Carriers.

The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan et al., 2001b; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997); U.S. Pat. Nos. 4,551,482; 5,714,166; 5,510,103; 5,490,840; and 5,855,900), and a polysome (U.S. Pat. No. 5,922,545).

Conjugation of Targeting Ligands.

Antibodies, fragments, or derivatives can also be coupled to drugs or drug carriers using methods known in the art, including but not limited to carbodiimide conjugation, esterification, sodium periodate oxidation followed by reductive alkylation, and glutaraldehyde crosslinking (see e.g., Goldman et al., 1997; Cheng, 1996; Neri et al., 1997; Nabel, 1997; Park et al., 1997; Pasqualini et al., 1997; Bauminger & Wilchek, 1980; U.S. Pat. No. 6,071,890; and European Patent No. 0 439 095).

Administration.

Suitable methods for administration of a composition of the presently disclosed subject matter include, but are not limited to intravascular, subcutaneous, intramuscular, and intratumoral administration. In some embodiments, intravascular administration is employed. As used herein, the phrases "intravascular administration" and "intravascular provision" refer to administration of a composition directly into the vascular network of a subject. Techniques that can be employed for intravascular administration of compositions are known to those of skill in the art, and include, but are not limited to intravenous administration and intraarterial administration. It is understood that any site and method for intravascular administration can be chosen, depending at least in part on the species of the subject to which the composition is to be administered. For delivery of compositions to pulmonary pathways, compositions can be administered as an aerosol or coarse spray.

III. Methods for Using Hornerin Inhibitors and/or Other Hornerin-Binding Molecules In some embodiments, the presently disclosed subject matter provides methods for treating tumors. In some embodiments, the presently disclosed methods comprise contacting a tumor cell and/or a tumor-associated endothelial cell with an effective amount of a hornerin inhibitor to reduce a biological activity of a hornerin gene product in the tumor cell and/or the tumor-associated endothelial cell, thereby treating the tumor.

In some embodiments, the presently disclosed subject matter provides methods for increasing the survival of a subject with a tumor. In some embodiments, the presently disclosed methods comprise administering to the subject an amount of a hornerin inhibitor effective to reduce a biological activity of a hornerin gene product in a tumor cell and/or a tumor-associated endothelial cell, thereby increasing the survival of the subject relative to a subject to whom the hornerin inhibitor has not been administered.

In some embodiments, the presently disclosed subject matter provides methods for suppressing tumor growth in a subject. In some embodiments, the presently disclosed methods comprise administering to a subject bearing a tumor an effective amount of a composition comprising a hornerin inhibitor, optionally wherein the comprising further comprises a second anti-tumor therapeutic agent.

In some embodiments, the presently disclosed subject matter provides methods for reducing tumor vascularity in a subject. In some embodiments, the presently disclosed methods comprise administering to a subject bearing a tumor an effective amount of a composition comprising a hornerin inhibitor, optionally wherein the comprising further comprises a second anti-tumor therapeutic agent.

In some embodiments of the presently disclosed methods, the effective amount of the hornerin inhibitor is effective to decrease tumor leakiness, increase tumor oxygenation, increase apoptosis of the tumor cell and/or the tumor-associated endothelial cell, reduce growth of the tumor, or any combination thereof in order to treat the tumor.

In some embodiments of the presently disclosed methods, the hornerin inhibitor comprises an siRNA that is designed to hybridize to a hornerin gene product present within the tumor cell and/or the tumor-associated endothelial cell to thereby inhibit a biological activity of the hornerin gene product in the tumor cell and/or the tumor-associated endothelial cell.

In some embodiments of the presently disclosed methods, the tumor cell and/or the tumor-associated endothelial cell is present within a subject, optionally a human subject.

In some embodiments of the presently disclosed methods, the contacting results from administering an effective amount of an anti-hornerin siRNA into the tumor.

In some embodiments, the presently disclosed methods further comprise contacting the tumor and/or administering to the subject one or more additional anti-tumor treatments. In some embodiments, the one or more additional anti-tumor treatments are selected from the group consisting of radiotherapy, chemotherapy, immunotherapy, anti-inflammatory therapy, and combinations thereof. In some embodiments, the one or more additional anti-tumor treatments comprises an anti-VEGF therapy, optionally an anti-VEGFR2 therapy. In some embodiments, the anti-VEGFR2 therapy comprises use of an anti-VEGFR2 antibody or VEGFR2-binding fragment thereof and/or a small molecule anti-VEGFR2 inhibitor. In some embodiments, the anti-VEGFR2 antibody or VEGFR2-binding fragment thereof is selected from the group consisting of ramucirumab or a VEGFR2-binding fragment thereof. In some embodiments, the small molecule anti-VEGFR2 inhibitor is selected from the group consisting of tivozanib (1-[2-chloro-4-(6,7-dimethoxyquinolin-4-yl)oxyphenyl]-3-(5-methyl-1,2-oxazol-3-yl)urea), axitinib (N-Methyl-2-[[3-[(E)-2-pyridin-2-ylethenyl]-1H-indazol-6-yl]sulfanyl]benzamide), lenvatinib (4-[3-Chloro-4-(cyclopropylcarbamoylamino)phenoxy]-7-methoxy-quinoline-6-carboxamide), pazopanib (5-({4-[(2,3-Dimethyl-2H-indazol-6-yl)methylamino]pyrimidin-2-yl}amino)-2-methylbenzenesulfonamide), regorafenib (4-[4-({[4-Chloro-3-(trifluoromethyl)phenyl]carbamoyl}amino)-3-fluorophenoxy]-N-methylpyridine-2-carboxamide hydrate), sorafenib (4-[4-[[4-chloro-3-(trifluoromethyl)phenyl]carbamoylamino]phenoxy]-N-methyl-pyridine-2-carboxamide), sunitinib (N-(2-Diethylaminoethyl)-5-[(Z)-(5-fluoro-2-oxo-1H-indol-3-ylidene)methyl]-2,4-dimethyl-1H-pyrrole-3-carboxamide), vandetanib (N-(4-bromo-2-fluorophenyl)-6-methoxy-7-[(1-methylpiperidin-4-yl)methoxy]quinazolin-4-amine), pharmaceutically acceptable salts thereof, and combinations thereof. In some embodiments, the anti-VEGF therapy comprises use of an anti-VEGF antibody or a VEGF-binding fragment thereof. In some embodiments, the anti-VEGF antibody or VEGF-binding fragment thereof is selected from the group consisting of bevacizumab and ranibizumab.

In some embodiments of the presently disclosed methods, the tumor is a tumor of the pancreas, breast, ovary, colon, or rectum, and/or a metastatic cell derived therefrom characterized by expression of a hornerin gene product in a cell of the tumor and/or an endothelial cell associated therewith.

In some embodiments, the presently disclosed subject matter provides methods for treating diseases, disorders, and/or conditions associated with undesirable hornerin expression. In some embodiments, the methods comprise contacting a cell, tissue, or organ that is characterized by undesirable hornerin expression with an effective amount of a hornerin inhibitor to reduce a biological activity of a hornerin gene product in the cell, tissue, or organ to thereby treat the disease, disorder, or condition. In some embodiments, the disease, disorder, or condition is a cardiovascular disease, disorder, or condition, optionally heart disease.

In some embodiments, the presently disclosed subject matter provides methods for modulating hornerin biological activities in vivo, in vitro, or ex vivo. In some embodiments, methods comprise contacting a hornerin gene product with a modulator, wherein the hornerin biological activity is modulated. In some embodiments, the modulator is a hornerin inhibitor, and the hornerin biological activity is reduced or inhibited. In some embodiments, the modulator is an anti-hornerin antibody or a small molecule or peptide that binds to hornerin to modulate its activity.

In some embodiments, the presently disclosed subject matter also provides methods for imaging cells, tissues, and/or organs that express hornerin. In some embodiments, the presently disclosed methods comprise contacting the cell, tissue, and/or organ with a composition as disclosed herein, wherein the active agent is a detectable agent, optionally wherein the detectable agent comprises an imaging agent selected from the group consisting of a paramagnetic ion, a radioactive ion, and a fluorogenic ion. In some embodiments, the radioactive imaging agent is selected from the group consisting of gamma-emitters, positron-emitters and x-ray-emitters. In some embodiments, the radioactive imaging agent is selected from the group consisting of $^{43}$K, $^{52}$Fe, $^{57}$Co, $^{67}$Cu, $^{67}$Ga, $^{68}$Ga, $^{77}$Br, $^{81}$Rb/$^{81M}$Kr, $^{87M}$Sr, $^{99M}$Tc, $^{111}$In, $^{113}$In, $^{123}$I, $^{125}$I, $^{127}$Cs, $^{129}$Cs, $^{131}$I, $^{132}$I, $^{197}$Hg, $^{203}$Pb, and $^{206}$Bi.

The presently disclosed subject matter also provides in some embodiments methods for imaging cells, tissues, and/or organs that expresses hornerin. In some embodiments, the methods comprise contacting the cell, tissue, or organ with a composition as disclosed herein, wherein the active agent is a detectable agent, optionally wherein the detectable agent comprises an imaging to agent selected from the group consisting of a paramagnetic ion, a radioactive ion, and a fluorogenic ion.

The presently disclosed subject matter also provides in some embodiments methods for delivering active agents to cells, tissues, and/or organs that expresses hornerin. In some embodiments, the methods comprise contacting the cell, tissue, and/or organ with the composition as disclosed herein, wherein the active agent is selected from the group consisting of a detectable agent and a therapeutic agent. In some embodiments, the detectable agent comprising an imaging agent selected from the group consisting of a paramagnetic ion, a radioactive ion, and a fluorogenic ion. In some embodiments, the therapeutic moiety is selected from the group consisting of a chemotherapeutic agent, a toxin, a radiotherapeutic agent, or a combination thereof.

IV. Other Embodiments of the Presently Disclosed Subject Matter

The presently disclosed subject matter also provides any and all devices, systems, apparatuses, uses, and/or methods shown and/or described expressly or by implication in the information provided herewith, including but not limited to features that may be apparent and/or understood by those of skill in the art.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the Examples

Animals.

All experiments were performed on male 9-10 week-old athymic nude (nu/nu) mice purchased from Charles River Laboratories (Wilmington, MA, USA). All procedures were approved by the University of Virginia Institutional Animal Care and Use Committee and in compliance with federal regulations.

Study Design.

A tumor sample size of four was determined by power analysis based on prior tumor xenograft studies. For our 80% power analysis, the difference between means was 200 mm$^3$, standard deviation was 100 mm$^3$, and P-value<0.05 (P<0.05). Tumors were measured at least twice weekly until their volume was >1000 mm$^3$, at which point animals were euthanized. Tumor size data were collected from each tumor, with the exception of one tumor in the combination treatment experiment that was identified with 90% confidence via Grubb's Outlier Test. The following number of mice in each treatment cohort was evaluated for tumor outgrowth: (Scr siRNA/ctrl., N=15; Hrnr siRNA/ctrl., N=14; Scr siRNA/AV-951, N=8; Hrnr siRNA/AV-951, N=8).

Phage Screen and Sequencing.

To conduct the phage screen, 10 μL of PhD-7 phage display library (New England Biolabs, Ipswich, MA, USA) was combined with 190 μL of Dulbecco's phosphate buffered saline (DPBS) and injected intravenously into mice harboring orthotopic xenograft PDAC tumors. Phage circulated for 8-10 minutes before the animals were euthanized and cardiac perfused with 30 mL of DPBS. Tumors were minced into 1-2 mm segments and Dounce homogenized in a solution consisting of DPBS+1% TritonX, ethylene diamine tetraacetic acid, and protease inhibitors (Thermo Scientific, Waltham, MA, USA). The phage was amplified according to manufacturer's instructions and two additional rounds of screening were completed as described above.

After three rounds of screening, phage were isolated from plaques and placed in water, upon which 10 μL of bacterial lysis/phage water solution was added as template for PCR amplification. Primer sequences: Forward: 5'-CCTT-TAGTGGTACCTTTCTAT-3' (SEQ ID NO: 31); Reverse: 5'-GCCCTCATAGTTAGCGTAACG-3' (SEQ ID NO: 32). The amplicon was sequenced using a 3730 DNA Analyzer (Applied Biosystems, Foster City, CA, USA).

Cell Culture.

L3.6pl tumor cells were obtained from Dr Craig Logsdon (University of Texas, MD Anderson Cancer Center, Houston, TX, USA), grown in minimal essential medium (MEM) with 10% fetal bovine serum and penicillin/streptomycin, and passaged every 72 h. All experiments involving L3.6pl cells were completed from passage 10-20. HUVEC were purchased from Lonza (Basel, Switzerland), grown in endothelial growth media supplemented with an endothelial cell SingleQuot kit (Lonza), and characterized as >90% double-positive for CD31/CD105 at passage four. HUVEC were passaged every 72 hours and used between passages two through eight. Human primary epidermal keratinocytes (American Type Culture Collection (ATCC), Manassas, VA, USA) and COCA mouse epidermal keratinocytes (Sigma Aldrich, St. Louis, MO, USA) were cultured in dermal cell basal media supplemented with a keratinocyte growth kit (ATCC). All cell lines were tested for mycoplasma contamination and maintained in a humidified atmosphere containing 5% $CO_2$ at 37° C.

Preparation of Tumor-Conditioned Media.

Tumor-conditioned media (TCM) were prepared from L3.6pl-conditioned media that had been collected after 72 hours of production and passed through a cell culture 0.22 μm syringe filter (Argos Technologies, Elgin, IL, USA). Media were concentrated to 10× using Ultra-1010 kilodalton molecular weight cutoff centrifugation filter units (Millipore, Darmstadt, Germany) and stored at −20° C.

Phage-Based ELISA.

HUVEC were plated in MaxiSorp 96-well plates (NUNC, Rochester, NY, USA) and cultured for 24 hours, at which time the cells were treated with media containing VEGF (VEGFCM) at B-max concentration (Igarashi et al., 2003) or TCM for an additional 24 h. ELISA was initiated by adding 1010 isolated phage to each well for a 1 hour incubation. After three washes with DPBS+0.1% Tween-20 (DPBST), the cells were incubated with horse radish peroxidase (HRP)-tagged anti-M13 antibody (GE Healthcare, Little Chalfont, UK, 27-9421-01; (1:3000)) for 30 min. The plates were washed three additional times (DBPST) then developed with 200 μL 3,3',5,5'-Tetramethylbenzidine (Sigma) for 10 minutes. The $A_{650}$ was measured on a microplate reader (Molecular Devices, Sunnyvale, CA, USA).

Two-Way ANOVA Analysis.

Absorbance values were corrected by comparison to unmodified control KE phage. To validate and confirm which clones reliably bound TCM and/or VEGFCM over VC, two-way ANOVA analysis (via MATLAB software) was completed on data from two separate experiments (N=6). Independent variables tested were conditioned media type and the two sets of experimental data for each day. Also, an interaction term was computed. For clones to be classified as a TCM or both TCM and VEGFCM binder, a significant difference (P<0.01) had to be achieved in the conditioned media vs. VC comparison, but not between experimental data sets or the interaction factor.

FITC Labeling of Phage Clones.

Following an established protocol described briefly here (Makino et al., 2001), phage were first suspended at a concentration of $10^9$ plaque forming units (pfu)/μL in DPBS. FITC was solubilized in dimethyl sulfoxide (25 μg/2 μL) and added to 200 μL of the phage solution. Following a 1 hour incubation at RT with rocking, the labeled phage were purified by three rounds of polyethylene glycol precipitation and resuspended in DPBS. FITC-labeled phage (200 μL) was injected via tail vein and allowed to circulate for 4 hours. The animal was cardiac perfused prior to removal of the tumored pancreas for cryopreservation.

Immunoblot.

HUVECs were cultured in 10 cm dishes for 24 hours prior to a change to media containing VEGF (at B-max concentration), TCM, or VC. After 24 hours treatment, the cells were washed with DPBST two times and lysed with radio-immunoprecipitation assay (RIPA) buffer (Thermo Scientific). Lysate protein concentrations were measured by the bicinchoninic acid assay (Pierce, Waltham, MA, USA) and equivalent amounts of protein were loaded into precast 4-15% tris-glycine eXtended (TGX) polyacrylamide gels (Bio-Rad, Hercules, CA, USA). The proteins were resolved by electrophoresis and transferred to nitrocellulose membranes using the iBlot system (Invitrogen, Carlsbad, CA, USA). The membranes were then washed in Tris-buffered saline+1% Tween-20 (TBST), blocked for 30 minutes in TBST+2% milk solution, and incubated overnight at 4° C. with primary antibodies anti-hornerin (Abcam, Cambridge, UK, ab78909; (1:1000)) and anti-HSP90 (Cell Signaling Technology, Danvers, MA, USA, 4877; (1:1000)). The following day the membranes were washed and subsequently incubated with the secondary antibodies anti-goat HRP (R&D Systems, Minneapolis, MN, USA, HAF109; 1:5000) and anti-rabbit HRP (GE Healthcare, NA934V; 1:5000) for 45 minutes at RT. After washing, the membranes were incubated in luminol/peroxide substrate reagents (Millipore), exposed to HyBlot autoradiography film (Denville Scientific, South Plainfield, NJ, USA), and developed. The films were scanned using a tabletop office scanner and converted to JPEG files for densitometry. Relative densitometry was computed using the "Gel Tool" in Image J (National Institutes of Health (NIH), Bethesda, MD, USA). For immunoblot detection of protein expression following EGF treatment, HUVECs were plated at a density of 0.15× $10^6$ cells/well in six-well cluster plates in complete media. The adherent cells were subsequently washed twice with serum-free media and replenished with EGF-free complete media for 14 hours, upon which the cells treated with EGF-free complete media supplemented with increasing concentrations of recombinant human EGF (PeproTech, Rocky Hill, NJ, USA). Lysate preparations were generated after 24 hours treatment. L3.6pl cells were plated in complete media in six-well cluster plates at a density of 0.2×$10^6$ cells/well. On day 2, the cells were replenished with serum-free media and serum starved overnight, upon which EGF was added at a concentration of 1, 10, or 100 ng/mL. Lysate preparations were generated after 48 hours treatment. Human keratinocytes were plated at a density of 0.1×$10^6$ cells/well in six-well plates, treated on day 2 with media containing either EGF or 2 mM $CaCl_2$, and lysed after 48 hours treatment. Lysate preparations were subjected to immunoblot using the primary antibodies anti-hornerin (Abcam; (1:1000)) and anti-beta actin (Cell Signaling, 3700, clone 8H10D10; (1:4000)), and corresponding secondary antibodies anti-goat HRP (R&D Systems; 1:10,000) and anti-mouse HRP (R&D Systems, HAF018; 1:10,000).

Angiogenesis Array.

Major constituents of TCM were determined using a Human Angiogenesis Antibody Array (Affymetrix, Santa Clara, CA, USA) per manufacturer's instructions. TCM and VC media were incubated on separate test strips and then assayed for elevated growth factors in TCM relative to VC. The film was developed, scanned, and subjected to densitometry analysis using Image J. The absolute difference between TCM and VC was computed. To obtain lysates for western blots, HUVEC cells were seeded in 10 cm circular dishes and allowed to grow for 48 hours. Next, growth factors were added in a change of media at published B-max concentrations (IL-654, IL-855, IL-1256, TNF57, bFGF58) and the cells were incubated for an additional 24 hours. The cells were then washed with DPBST two times and lysates were generated for immunoblot detection.

De-Identified Human PDAC Specimens.

De-identified resected human PDAC specimens were obtained through the UVA Biorepository and Tissue Research Facility (BTRF) in accordance with the policies established by the University of Virginia Institutional Review Board for Health Sciences Research. Ten formalin-fixed, paraffin-embedded tumor samples were cut into 5 μm sections and analyzed for hornerin expression by immuno-histochemistry. To accomplish this, the sections were deparaffinized with xylene and ethanol, treated with low pH antigen unmasking solution (Vector Labs, Burlingame, CA, USA) in a microwave for 20 minutes, and washed twice with DPBS. Next, endogenous peroxidase activity was quenched using 0.5% $H_2O_2$ in methanol for 30 minutes at room temperature. The slides were then washed, blocked for 30 min in DPBS+5% BSA (blocking buffer), and incubated with anti-hornerin antibody (Sigma, HPA031469; 1:100) in blocking buffer at 4° C. overnight. After three washes with DPBS, the slides were incubated with anti-rabbit HRP-labeled secondary antibody (GE Healthcare; 1:2500) in blocking buffer for 30 minutes at RT. The signal was developed using 3,3'-diaminobenzidine (DAB) tablets (Thermo Fisher Scientific) and subsequently counterstained with hematoxylin (Thermo Fisher Scientific). The sections were then dehydrated in 100% ethanol (three washes), 100% xylene (two washes), and mounted with CytoSeal 60 (Thermo Scientific).

A certified pathologist scored the stained slides by stain intensity and percentage of positive cells. Endothelial cells were identified by a combination of cell morphology, nucleus shape, and presence of erythrocytes. Histological images were taken with an Olympus BX-41 microscope and QImaging Retiga-2000R camera.

Tumor Studies.

For tumor implantation, L3.6pl cells were grown under normal culture conditions for 72 hours prior to being trypsinized and enumerated. The cells were suspended in aliquots of 500,000 cells/50 μL Hanks Balanced Salt Solution (HBSS; Corning, Manassas, VA, USA) and 50 μL of Matrigel (BD Biosciences, San Jose, CA, USA) was added to each aliquot of cells prior to implantation. The cell-Matrigel slurry was injected subcutaneously into nu/nu mice on the flanks or orthotopically into the pancreas (Seaman et al., 2011). The injection site for subcutaneous tumors was monitored daily for growth and tumor volume was calculated form caliper measurements using the formula (width$^2$× length)/2.

The VEGFR inhibitor AV-951 (Selleck Chemicals, Houston, TX, USA) was suspended in 0.5% methocel+0.5% Tween-20 in HBSS to increase viscosity and 50 μL of 1.0 mg/kg AV-951 or VC solution was administered once daily by oral gavage (22-gauge gavage needle (Kent Scientific, Torrington, CT, USA) connected to a 1 mL syringe). Silencer Select mouse hornerin siRNA (Hrnr siRNA; 5'-GCAUGGAUCUUGUUGCGGUTT-3'; SEQ ID NO: 49; Invitrogen) was aligned against human hornerin transcripts using the basic local alignment tool (BLAST) algorithm and no match was returned. To prepare Hrnr siRNA and Silencer Select Negative Control #1 Scr siRNA (Invitrogen; catalog number 4390844) for injection, 10 µg of hornerin or control siRNA were combined with in vivo-jetPEI transfection reagent (Polyplus, France) in solution with 5% glucose per Polyplus instructions (total volume 50 µL). After a 30 minutes incubation, the siRNA solutions were injected slowly into the center of the tumor. A second independent hornerin knockdown experiment was conducted using a pooled set of three unique mouse Hrnr siRNA duplexes (5'-GGAAUUAAGUUAGGAAGAAUAAUTT-3' (SEQ ID NO: 50); 5'-AGAGUGCAUAGACAAGUAGAAACCT-3' (SEQ ID NO: 51); 5'-CCCUACUUCAGAACAAUAUGG-GUCT-3' (SEQ ID NO: 52)) and Scr siRNA (Origene, Rockville, MD, USA). The reagent preparation and injection protocol were similar to that described above.

Following completion of the treatment schedule, the mice were killed, cardiac perfused, and the tumors were excised and fixed in formalin overnight. The tumors were paraffin embedded and cut into 5 (thin) or 50 µm (thick) sections. Tumor vessel parameters were evaluated in the following number of tumors for each treatment cohort: (Scr siRNA/ctrl., N=10; Hrnr siRNA/ctrl., N=10; Scr siRNA/AV-951, N=4; Hrnr siRNA/AV-951, N=4).

Immunofluorescent Staining.

Tumor sections were deparaffinized, rehydrated, heated in antigen retrieval solution (Vector), blocked for 30 minutes in blocking buffer, and incubated with anti-CD34 antibody (Abcam, ab8158, clone MEC14.7; 1:100) in blocking buffer overnight at 4° C. The sections were then incubated with goat anti-rat FITC secondary antibody (Abcam, ab6840; 1:100) in blocking buffer prior to mounting with Prolong Gold Antifade reagent (Invitrogen). Anti-actin, α-smooth muscle Cy3 antibody (Sigma, C6198, clone 1A4; 1:200) was added to the primary antibody solution if assaying for alpha-smooth muscle actin. To compare hornerin expression in vessels and tumor tissue treated with Hrnr siRNA and Scr siRNA, thin paraffin sections were deparaffinized and stained with anti-CD34 and anti-hornerin antibodies described. Images were collected using a Nikon TE 2000-E2 microscope (Nikon Instruments) equipped with a Melles Griot Argon Laser System (Melles Griot, Carlsbad, CA, USA) and a Nikon D-Eclipse C1 confocal attachment and analyzed by Measurement Tool in Image J. To measure the relative hornerin expression in tumor vessels, three vessel segments per image were isolated and their mean intensity and area were measured and recorded. A weighted mean intensity was calculated to correct for differences in selected area. To measure the relative hornerin expression in tumor tissue, the mean intensity from three square sections (75×75 pixel) of tumor tissue per image was measured and recorded.

Vessel parameters were measured using RAVE software (Seaman et al., 2011). For detection of proliferation and apoptosis, the sections were incubated with the primary antibodies anti-Ki67 (Abcam, ab15580; 1:200) or anti-cleaved caspase 3 (Cell Signaling, 9661; 1:200), respectively, overnight at 4° C. followed by incubation with anti-rabbit AF594 (Abcam, 150080; 1:200).

Human keratinocytes or COCA cells were plated on fibronectin-coated coverslips and treated with 2 mM CaCl2 to induce differentiation. After 48 hours the cells were fixed in 4% paraformaldehyde, permeabilized in methanol, blocked in 5% BSA/PBS, and incubated with anti-hornerin antibody (Sigma; 1:150) and antibeta actin FITC (Sigma, F3022, clone AC-15; 1:250). Following incubation with anti-rabbit AF594 (1:400) the coverslips were mounted in Prolong Gold+DAPI and analyzed by microscopy. The acquired images were prepared using Image J.

Quantitative PCR.

Day 10 tumors were injected with either Scr siRNA or Hrnr siRNA and excised 20 hours later. The tumors were immediately washed in PBS (+Mg/+Ca), minced with scalpels, treated with Collagenase Type II (Worthington Biochemical Corporation, Lakewood, NJ, USA; (2.0 mg/mL) serum-free DMEM, 100 minutes at 37° C.), and filtered through a 40 µm cell strainer. The cell suspension (filtrate) was incubated with the following antibody/dye panel for FACS; anti-CD45 AF488 (1:100; Biolegend, San Diego, CA, USA, 103121, clone 30-F11), anti-CD31 AF647 (1:100; Biolegend, 102415, clone 390), LIVE/DEAD violet stain (1:200; Thermo Fisher). Flow cytometry analysis was completed on the Cyan ADP LX (Beckman Coulter). Compensation and data analysis was completed using FlowJo software (Ashland, OR, USA). FACS was completed in the UVA flow cytometry core on the Influx cell sorter (BD Biosciences, Franklin Lakes, NJ, USA).

RNA was isolated from FACS-sorted $CD31^+CD45^-$ cells according to the manufacturer's protocol (Qiagen mini-prep kit), and concentration and purity were determined using a NanoDrop Spectrophotometer (Thermo Fisher). Complimentary DNA (cDNA) was generated (Qiagen QuantiTect Reverse Transcription Kit) and subjected to pre-amplification (SsoAdvanced PreAmp Supermix, Bio-Rad). For this reaction, 50 nM of each primer, mouse cyclophilin B (Forward 5'-TGCCGGAGTCGACAATGAT-3'; SEQ ID NO: 53; Reverse 5'-TGGAGAGCACCAAGACAGACA-3'; SEQ ID NO: 54) and mouse hornerin (Forward 5'-CCTG-GAAAGCATTGTCACTGT-3' SEQ ID NO: 55; Reverse 5'-CGGTGTCTGGATCATCTGG-3'; SEQ ID NO: 56; see Kumar et al., 2015) were combined with the PreAmp Supermix and cDNA template, and subjected to the following thermal cycling protocol: 3 minutes at 95° C. (polymerase activation and DNA denaturation), followed by 20 cycles of 15 seconds at 95° C. (denaturation) and 4 minutes at 58° C. (annealing/extension). The pre-amplified cDNA was subjected to qPCR (Qiagen SYBR Green PCR kit; 60° C. annealing temperature, 60 cycles). Melt curve analysis was performed on the hornerin and cyclophilin primer sets prior to data collection and normalized gene expression was determined by the delta delta $C_t$ method.

DCE-MRI and $K_{trans}$ Measurement.

To assess the in vivo function of tumor vascularity, DCE-MRI was performed on a 7.0 T Clinscan small animal imaging system (Bruker, Ettlingen, Germany) using a 30 mm inner-diameter birdcage radiofrequency coil. Mice (N=7) were imaged prior to treating tumors with Hrnr and Scr siRNA and again 6 days after treatment. Mice treated with the VEGFR inhibitor AV-951 (N=5) were image pre-siRNA treatment and 6 days posttreatment. Mice were anesthetized with 1.25% isoflurane anesthesia, which was maintained during imaging. Respiration and ECG were monitored during imaging using an MRI-compatible system (SA Instruments, Stony Brook, NY, USA). An indwelling tail vein catheter was established for administration of the gadolinium contrast agent Gd-DTPA, which is required in DCE imaging. Mice were placed supine in the imaging system, and body temperature was maintained at 36° C.±1° C. using circulating, temperature controlled water. Tumors were localized using a spin-echo imaging sequence, and an imaging plane that transected both tumors was chosen for DCE imaging.

A dual-Gd-bolus DCE-MRI acquisition strategy (Christian et al., 2004) was employed, which uses a low dose of contrast agent to accurately acquire the undistorted Gd concentration vs. time curve in the blood pool and a higher dose of contrast agent to acquire the Gd concentration vs. time curve in the tumor with high signal-to-noise ratio, since Gd-DTPA is known to have signal saturation effects at high doses in the blood pool (Christian et al., 2004). Short-axis ECG-gated images of the left ventricle were acquired using a saturation recovery gradient echo pulse sequence with the following imaging parameters: number of images=500, 1 image per heartbeat, echo time/repetition time/saturation delay time=0.8/1.6/10 ms, excitation flip angle=25°, image resolution=0.47×0.47×1 mm, field of view=30 mm, Gd-DTPA dose=0.025 mmol/kg, imaging time ~1 minute ECG and respiratory-gated images of the tumors were similarly acquired using a saturation recovery gradient echo pulse sequence with the following imaging parameters: number of images=350, echo time/repetition time/saturation delay time=1.1/2.0/200 ms, excitation flip angle=25°, averages=2, image resolution=0.195×0.195×1.5 mm, field of view=25 mm, Gd-DTPA dose=0.15 mmol/kg, imaging time ~5 minutes. Gd-DTPA concentration vs. time curves were generated by drawing regions of interest around the left ventricular cavity and each tumor. Each blood pool Gd-DTPA concentration vs. time curve was fit with a gamma-variate function during Gd wash-in and extrapolated with an exponential decay function during Gd wash-out to have the same temporal duration as its corresponding tumor Gd concentration vs. time curves. Tracer kinetic Kety model analysis (Tofts et al., 1999) was applied to the left ventricular and tumor Gd concentration vs. time curves, which yielded an estimate of the volume transfer constant $K_{trans}$, a widely-accepted MRI measurement of vascularity (Wedam et al., 2006; de Lussanet et al., 2007; Gaustad et al., 2008).

Photoacoustic Microscopy.

Using an established PAM system (Wang & Hu, 2012; Ning et al., 2015a; Ning et al., 2015b), the tumor vasculature was characterized in vivo. Two laser wavelengths, 532 and 559 nm, were used to simultaneously quantify microvascular diameter, oxygen saturation, and blood flow at the same spatial scale (Ning et al., 2015a). The applied optical energies were 100 and 75 nJ, which are below the maximum permissible exposure energy. Throughout the experiment, mice were maintained under anesthesia with 1.5% vaporized isoflurane and the body temperature was kept at 37° C. All experimental procedures were carried out in conformity with the laboratory animal protocol approved by the Animal Care and Use Committee at the University of Virginia.

In Vitro siRNA Experiments.

Figure 6A:
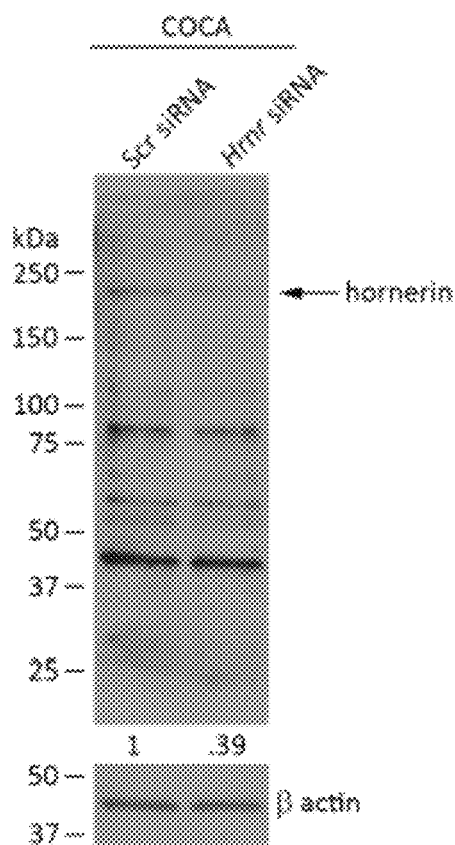
FIGS. 6A and 6B. Mouse Hrnr siRNA did not significantly reduce human hornerin expression.
Figure 6B:
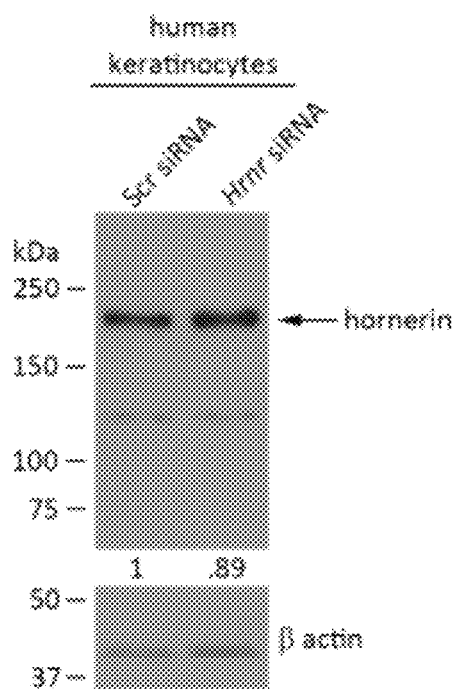

For in vitro siRNA-mediated hornerin knockdown, COCA cells and human keratinocytes were plated at a density of 0.1×10⁶ cells/well in a six-well cluster plate. The cells were treated the following day with Scr siRNA or Hrnr siRNA (Invitrogen; siRNA sequences identical to those utilized in tumor studies) following an established protocol (see Rachow et al., 2013). Briefly, 100 µL of 10 µM siRNA and 12.5 µL of Lipofectamine 2000 (LF2000; Invitrogen) were added to separate 625 µL OptiMEM (Thermo Fisher Scientific) aliquots. After 5 minutes at RT, the solutions were mixed and incubated for an additional 30 minutes, upon which 5 ml of keratinocyte media were added. The cells were incubated overnight in 3 ml of the siRNA/LF2000/media mixture, replenished the following morning with media containing 2 mM $CaCl_2$) to induce differentiation, and lysed in RIPA buffer 8 hours post-media change. Lysate preparations were subjected to immunoblot using the primary antibodies anti-human hornerin (Abcam; 1:1000), anti-mouse hornerin (Santa Cruz Biotechnology, Dallas, TX, USA, sc164605; 1:200), or anti-beta actin (Cell Signaling; 1:4000), and respective secondary antibodies anti-goat HRP (R&D Systems; 1:10,000), and anti-mouse HRP (R&D Systems; 1:10,000). Uncropped hornerin immunoblots are represented in FIGS. 6A and 6B.

Mass Spectrometry.

The gel piece was transferred to a siliconized tube and washed and destained in 200 µL 50% methanol overnight. The gel pieces were dehydrated in acetonitrile, rehydrated in 30 µL of 10 mM dithiolthreitol in 0.1M ammonium bicarbonate, and reduced at room temperature for 0.5 hours. The DTT solution was removed and the sample alkylated in 30 µL 50 mM iodoacetamide in 0.1M ammonium bicarbonate at room temperature for 0.5 hours. The reagent was removed and the gel pieces dehydrated in 100 µL acetonitrile. The acetonitrile was removed and the gel pieces rehydrated in 100 µL 0.1M ammonium bicarbonate. The pieces were dehydrated in 100 µL acetonitrile, the acetonitrile removed and the pieces completely dried by vacuum centrifugation. The gel pieces were rehydrated in 20 ng/µL trypsin in 50 mM ammonium bicarbonate on ice for 10 minutes. Any excess enzyme solution was removed and 20 µL 50 mM ammonium bicarbonate added. The sample was digested overnight at 37° C. and the peptides formed extracted from the polyacrylamide in two 30 µL aliquots of 50% acetonitrile/5% formic acid. These extracts were combined and evaporated to 15 µL for MS analysis.

The LC-MS system consisted of a Thermo Electron Velos Orbitrap ETD mass spectrometer system with a Protana nanospray ion source interfaced to a self-packed 8 cm×75 µm id Phenomenex Jupiter 10 µm C18 reversed-phase capillary column. About 7.5 µL of the extract was injected and the peptides eluted from the column by an acetonitrile/0.1M acetic acid gradient at a flow rate of 0.5 µL/min over 0.3 hours. The nanospray ion source was operated at 2.5 kV. The digest was analyzed using the double play capability of the instrument acquiring full scan mass spectra (Orbitrap, 60 K resolution) to determine peptide molecular weights followed by product ion spectra (ion trap) to determine amino-acid sequence in sequential scans. Data collection was maximized by using default dynamic exclusion settings.

The data were analyzed by database searching using the Sequest search algorithm within Proteome Discoverer (v1.2) against IPI Human (v3.78, 86,702 entries). The peptides and proteins identified for the sample are displayed using Scaffold (v3.0.6) with the following settings (parent=10 ppm, fragment=1 Da, trypsin, 60% peptide threshold, 90% protein threshold, Xcorr>1, 8, 2.2, 2.5, 3.5 for +1, +2, +3, +4, >C=57 fixed, M=167 variable). The proteins of particular interest are examined manually at the spectral level to determine if true positives.

Statistics.

Unless otherwise noted, all data are represented as mean±SEM and all P-values were calculated using a two-tailed, unpaired student's t-test. Two-way ANOVA statistical methods are described above.

Example 1

VEGF-Independent Vascular Binding Peptides

Figure 1A:
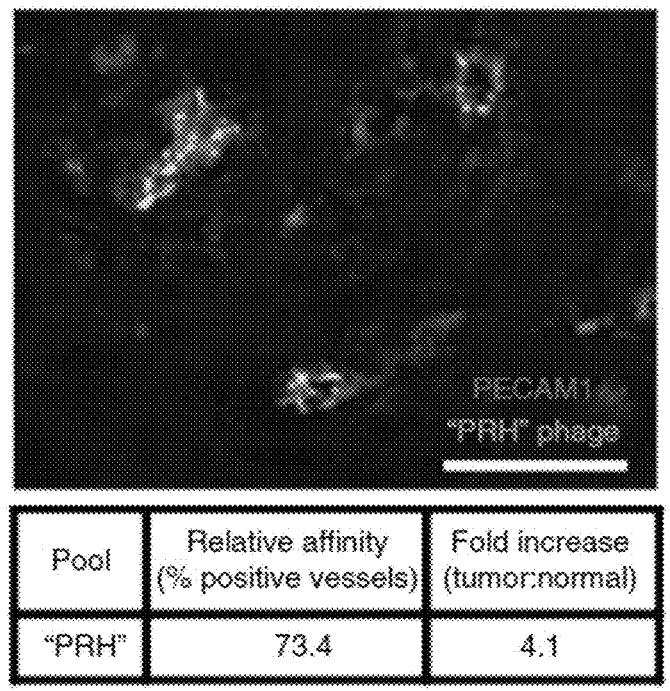
FIGS. 1A-1G: Identification of tumor endothelial cell-specific phage clones and hornerin as a non-VEGF but TCM-induced protein.

To elucidate peptides that bind specifically to tumor endothelium, an in vivo phage display screen was performed in mice bearing orthotopically implanted human PDAC cells. After three rounds of selection, 30 phage clones that were termed pancreatic tumor endothelial markers (PTEM) were sequenced, and the amino acid sequences are disclosed in Table 1. Before continuing with the in vitro screen, the specificity of a few of the selected clones for blood vessels was assessed in vivo through injection of fluorescently labeled phage (Kelly et al., 2006) into animals bearing orthotopic tumors. Specificity of the phage for tumor vessels was assessed by immunofluorescence (FIG. 1A). Three clones with similar homology, PRH, were employed in the analysis. The "PRH" pool (PTEM 12/17, 16) bound 73.4% (4.1-fold over normal pancreas vessels) of platelet endothelial cell adhesion molecule1-positive tumor vessels (FIG. 1A). The immunofluorescent images indicate that the fluorescein isothiocyanate (FITC)-phage remained bound to the luminal surface of the blood vessels even after vigorous perfusion.

Figure 1B:
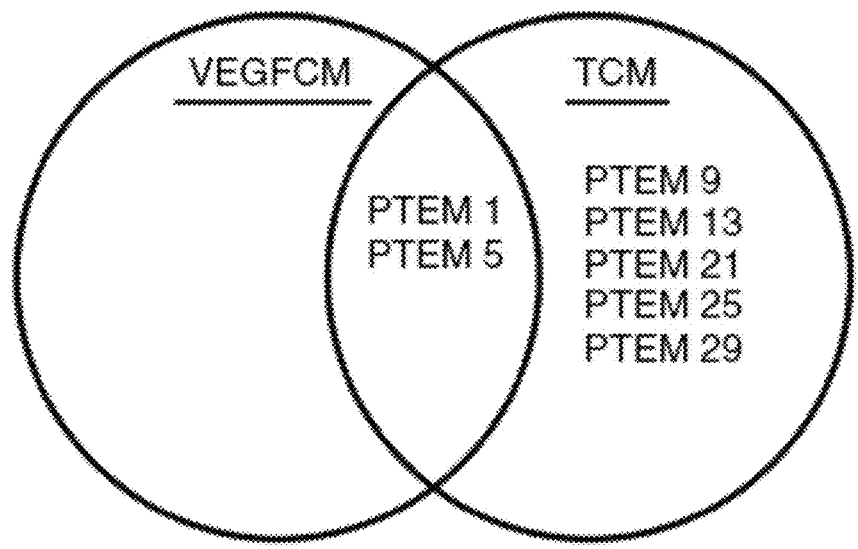
Figure 1C:
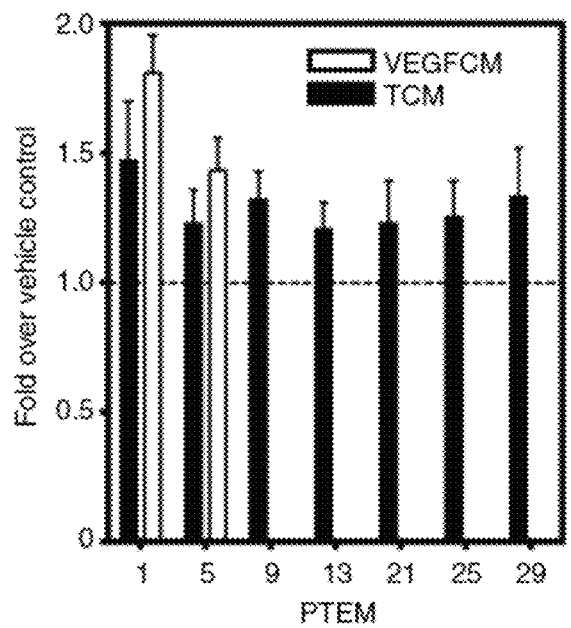
Figure 2A:
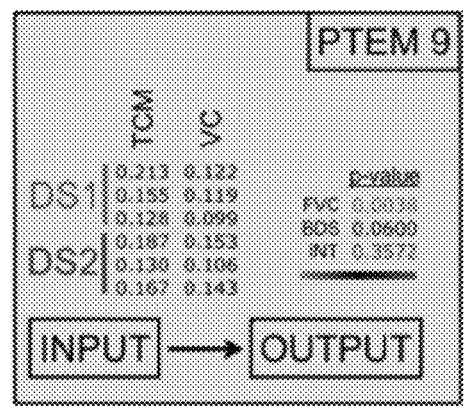
FIGS. 2A-2C. ELISA and two-way ANOVA analysis identified clones that displayed specific binding to TCM treated HUVEC.
Figure 2B:
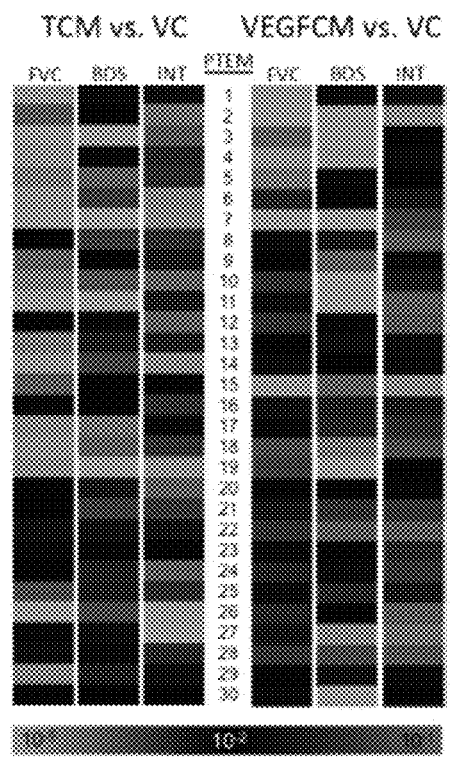
Figure 2C:
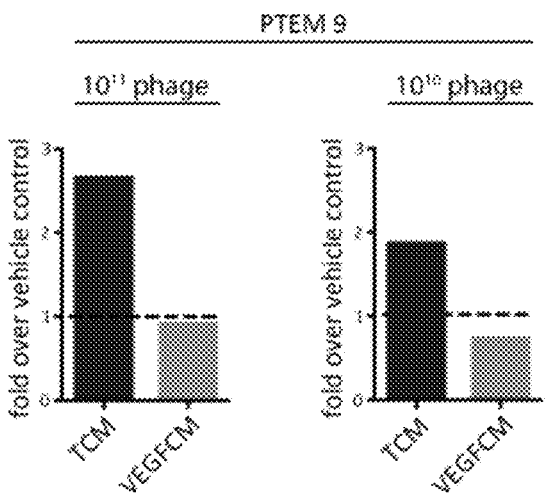

As VEGF is highly abundant in the pancreatic tumor milieu, clones were further segregated based on their ability to bind to VEGF-treated HUVECs vs. tumor conditioned media (TCM)-treated HUVECs. HUVECs were utilized as the ability of the peptides to bind to both human and mouse antigens was of interest. Enzyme-linked immunoabsorbent assay (ELISA) results were analyzed by two-way analysis of variance (ANOVA) to find clones that consistently bound to HUVECs treated with TCM, but not vehicle control (VC) or VEGF-supplemented control media (VEGFCM; FIGS. 2A and 2B). After analysis, the clones were grouped and organized in a Venn diagram (FIG. 1B). Although the PRH family demonstrated specificity and selectivity for tumor blood vessels in vivo, it failed to meet these criteria in subsequent in vitro screens, suggesting that it did not cross-react with a human target or the target was not present on human cells. Of the clones that bound selectively to TCM-treated HUVECs, PTEM 9 demonstrated the highest average specificity (FIG. 1C). These data were further validated in a subsequent ELISA using both M13KE phage (no displayed peptide; control) and PTEM 9 phage (FIG. 2C).

Example 2

Hornerin Identified as the Binding Partner of PTEM 9

Figure 1F:
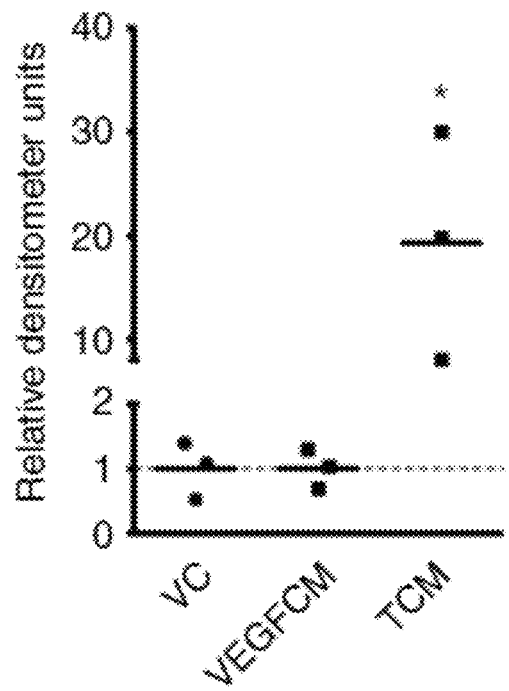
Figure 1D:
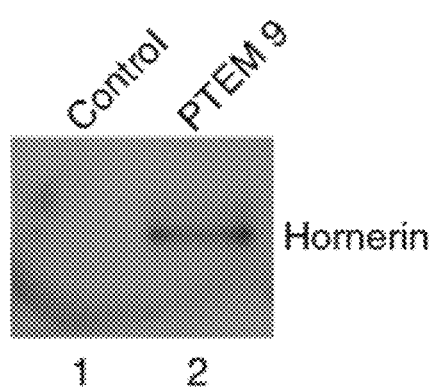

Phage display-based functional proteomics was employed to determine the binding partner of PTEM 9 (Reynolds et al., 2011). Tandem mass spectroscopy sequencing of lysates resulting from the functional proteomics process revealed hornerin as the candidate protein; six unique tryptic digest fragments were identified resulting in a percent coverage of 3.5%, coverage similar to what has been previously published utilizing this method (FIGS. 3A and 3B; Kelly et al., 2008; Reynolds et al., 2011). To confirm that hornerin was the identified protein, anti-hornerin immunoblotting on the PTEM 9 phage and control M13KE phage lysates was performed. A unique band in the PTEM 9 lane that was not present in the control sample corresponded to the predicted molecular weight of hornerin (FIG. 1D).

Example 3

Non-VEGF Soluble Factors Increase Hornerin Expression

Figure 1E:
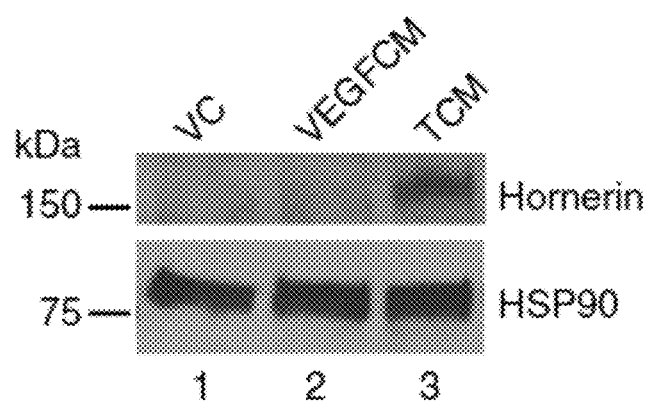
Figure 1G:
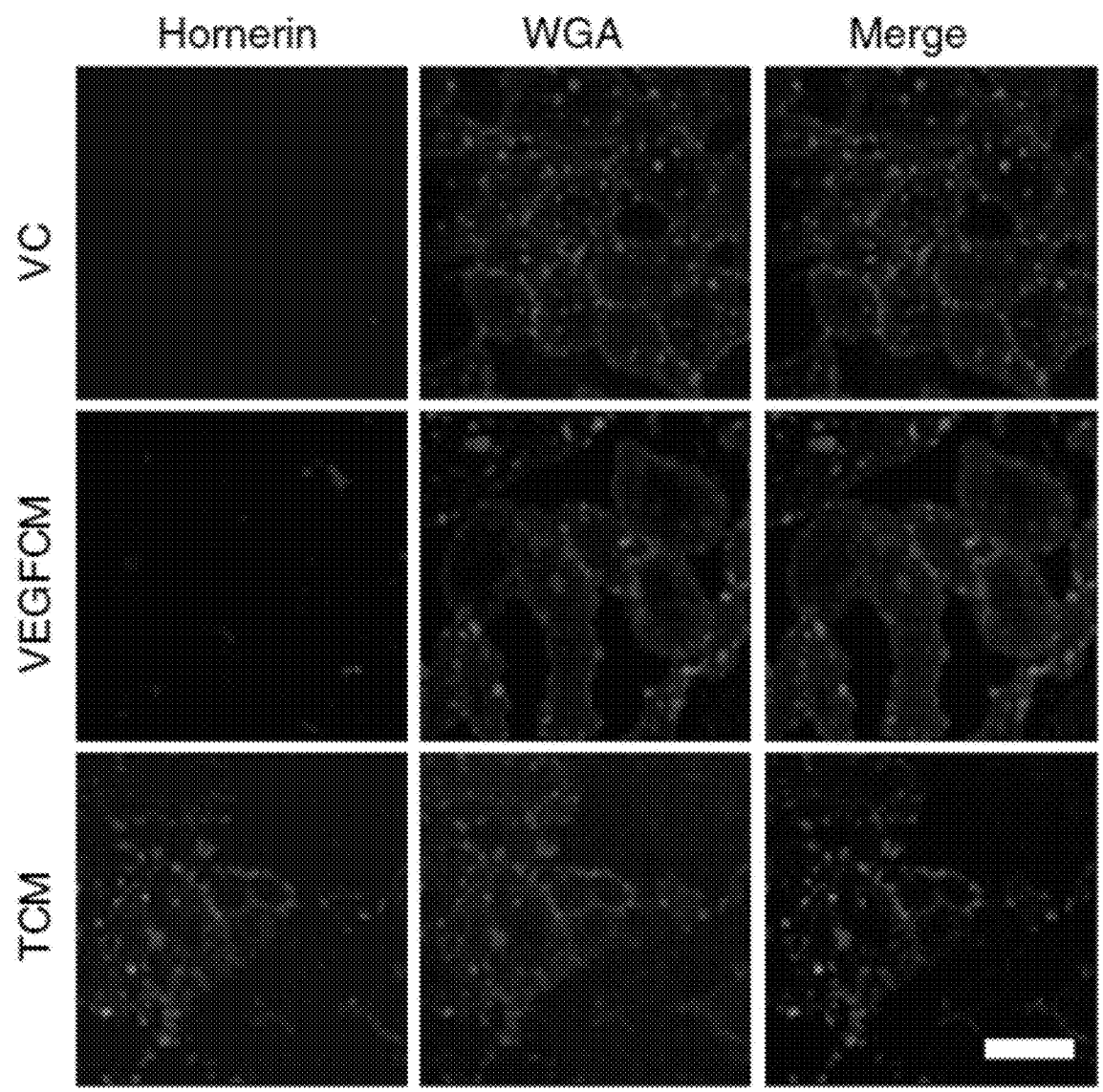

Based on the strategy utilized to segregate the peptides presented in FIG. 1B and FIGS. 2A-2C, it was hypothesized that expression of hornerin in HUVECs would increase upon treatment with TCM but not in response to VEGF. To test this, cell lysates from HUVECs treated with TCM, VEGFCM, and VC media were analyzed by immunoblot for the expression of hornerin. In TCM-treated HUVECs, hornerin expression was 19.3-fold higher when compared with VC, while treatment of HUVECs with VEGFCM resulted in no significant change of hornerin expression over VC (FIGS. 1E and 1F) Immunofluorescent detection of hornerin in nonpermeabilized HUVECs suggests hornerin co-localization with the plasma membrane following treatment with TCM (FIG. 1G). These data strongly indicated that hornerin was upregulated in response to factor(s) in the TCM and that hornerin accumulated at the plasma membrane.

Example 4

Hornerin is Expressed in Human PDAC Vessels

Figure 4C:
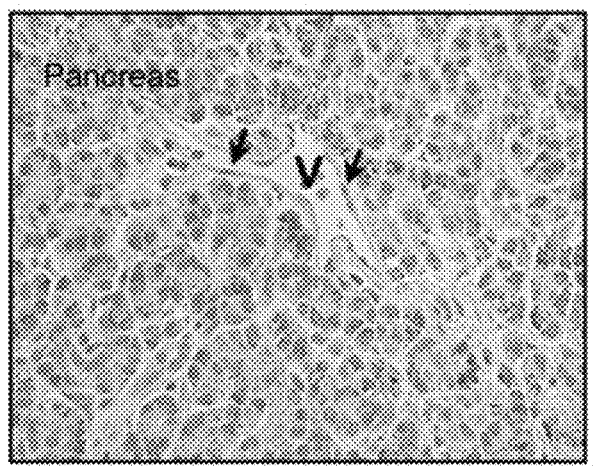
Figure 4C:
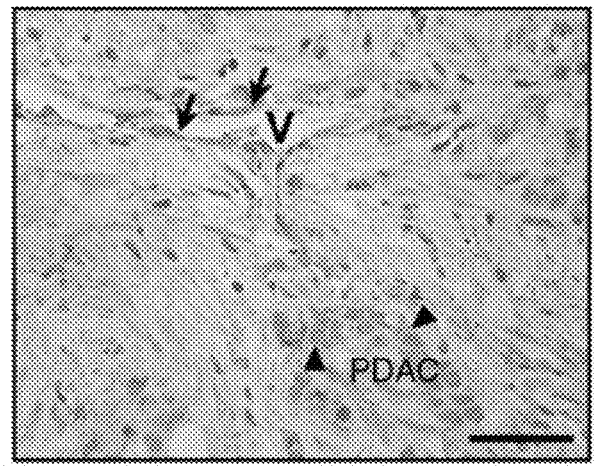
Figure 4C:
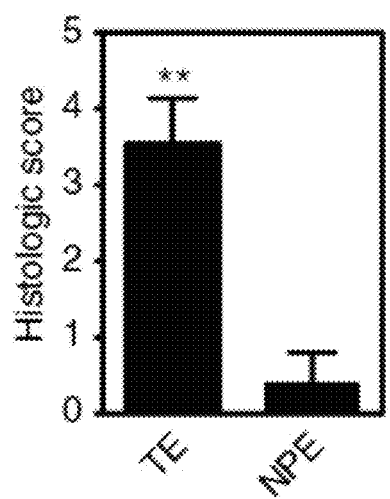
Figure 5A:
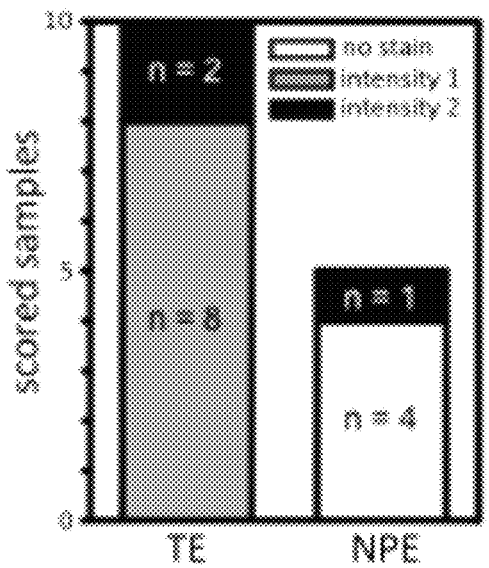
FIGS. 5A and 5B. Comparative hornerin expression in human pancreas specimens. The tumor endothelium (TE) and normal pancreas endothelium (NPE) in 10 human PDAC specimens were scored for hornerin expression based on immunohostochemical staining intensity (FIG. 5A) and the percentage of positively stained cells (FIG. 5B). N refers to the number of specimens that fit the specific criteria for each method of analysis.
Figure 5B:
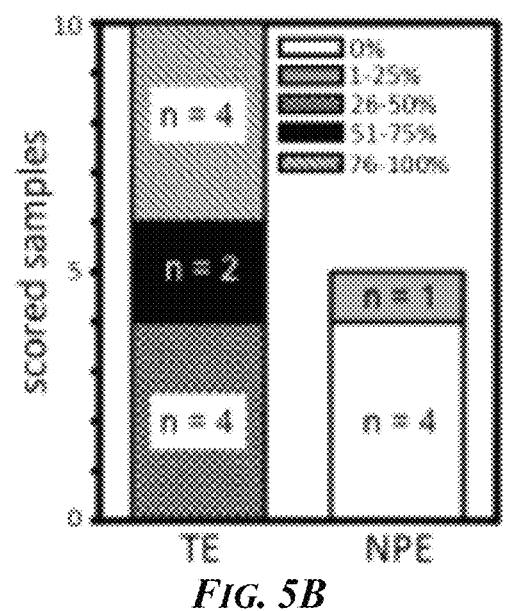

If hornerin was expressed in human tumor specimens was test4d. Hornerin expression in specimens from 10 PDAC patients (Table 3) was revealed by immunohistochemistry and scored by a certified pathologist at the University of Virginia. Normal pancreas endothelial cells (NPE) (arrows) were negative for hornerin expression (FIG. 4A), however tumor endothelial cells (TE; arrows) near PDAC (arrowheads) stained positively (FIG. 4B). Importantly, 5 of the 10 resected PDAC samples had areas of non-affected pancreas where NPE staining could be quantified. Analysis of the samples in each scoring component (intensity and percent positively stained cells; FIGS. 5A and 5B) revealed a large disparity between NPE and TE, with TE having a 7.1-fold higher score than NPE (FIG. 4C).

Figure 4D:
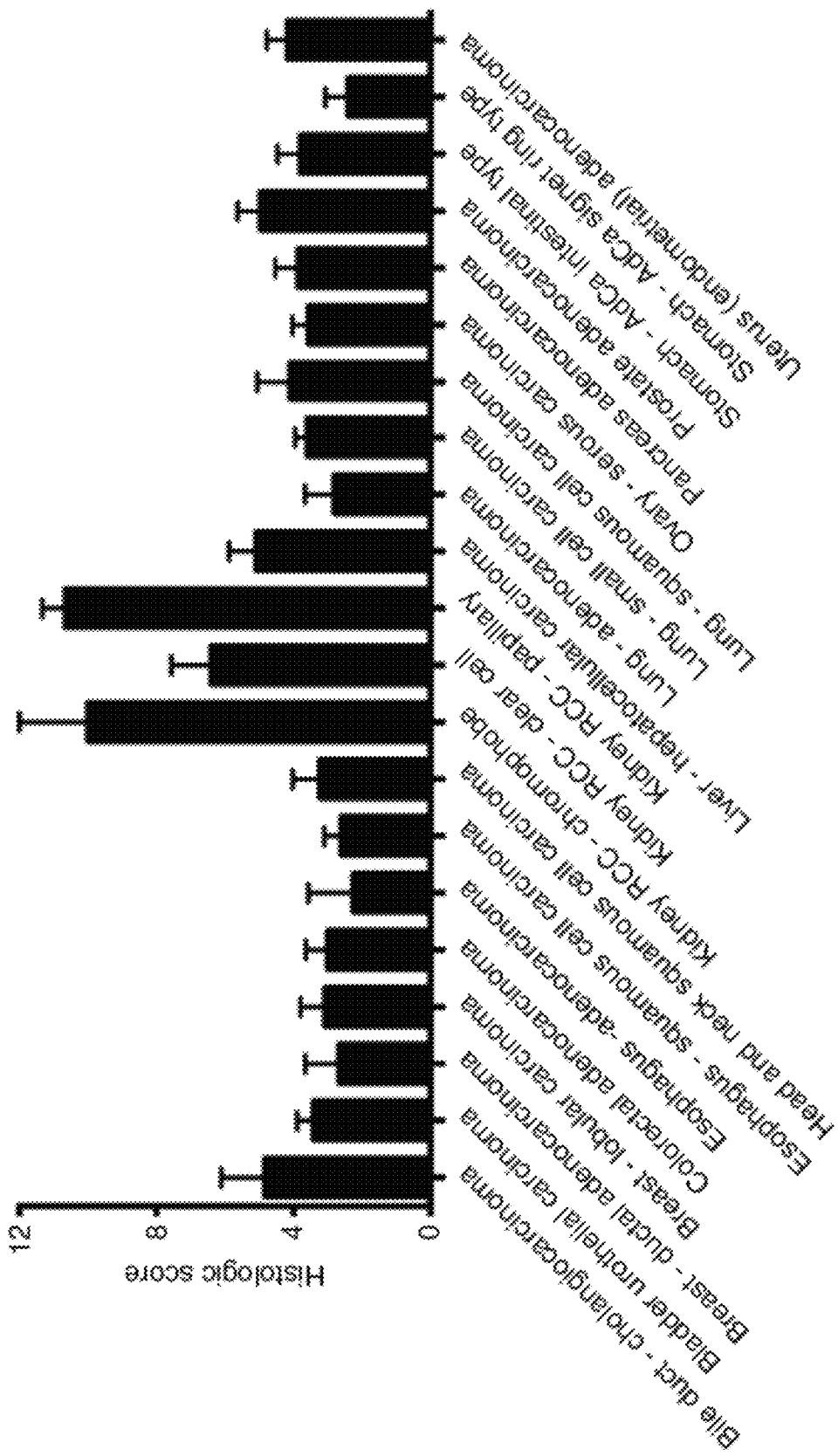

It was observed that PDAC cells and normal pancreas cells also stained positive for hornerin, indicating that hornerin might not be an ideal immunohistochemical biomarker for PDAC. However, the increased vessel expression suggested a tumor-specific phenotype and prompted the studies presented herein. To expand the analysis of hornerin expression in human tumor specimens, a pathologist scored several types of solid tumors in addition to PDAC. Notably, RCC (chromophobe, clear cell, and papillary) displayed the highest relative expression of hornerin in the panel that was evaluated (FIG. 4D).

TABLE 3

De-identified PDAC Patient and Rumor Characteristics Used in Assessment Of Hornerin Expression in Tumor-associated Epithelium

|  |  | Frequency (Number) |
|---|---|---|
| Age (Years) | 50-60 | 50% (5) |
|  | 60-70 | 30% (3) |
|  | 70-80 | 10% (1) |
|  | >80 | 10% (1) |
| Gender | Male | 40% (4) |
|  | Female | 60% (6) |
| Race | White | 100% (10) |
| Tumor Grade | 1 - Well Differentiated | 10% (1) |
|  | 2 - Moderately Differentiated | 20% (2) |
|  | 3 - Poorly Differentiated | 70% (7) |

Example 5

Hornerin Knockdown Led to Decreased Tumor Burden

Figure 7A:
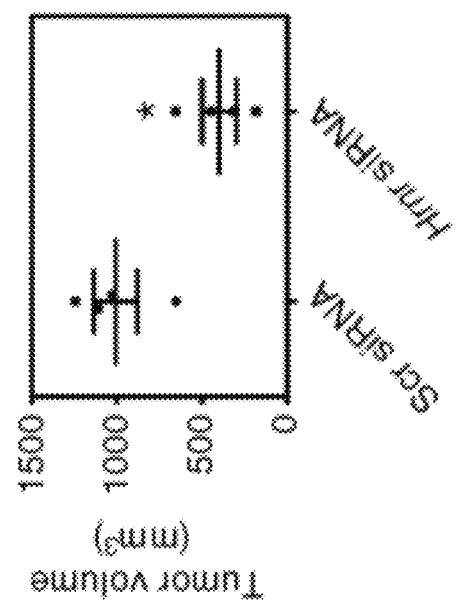
FIGS. 7A-7D: siRNA-mediated hornerin knockdown results in decreased tumor burden.

As hornerin is present in tumor vessels but not normal vessels, it was hypothesized that hornerin might play an important role in tumor vessel function and consequently regulate tumor progression. To address this, endothelial hornerin expression was decreased using intratumoral injections of mouse-specific hornerin siRNA (Hrnr siRNA) in a subcutaneous xenograft PDAC model (L3.6pl; PDAC of human origin). This model system was chosen carefully such that epithelial tumor tissue would be unaffected by Hrnr siRNA knockdown. To confirm that the Hrnr siRNA does not target human HRNR, in vitro siRNA knockdown experiments in mouse epidermal keratinocytes (COCA) and human keratinocytes were conducted. These cell lines were selected based on previous studies showing elevated hornerin expression in the epidermis (Makino et al., 2001; Takaishi et al., 2005; Henry et al., 2011). The results indicated a 60% reduction in hornerin expression in COCA cells treated with Hrnr siRNA (SEQ ID NO: 49) relative to control scrambled siRNA (Scr siRNA)-treated cells (FIG. 6A). Loss of hornerin was not observed to a significant degree (~10%) in the human keratinocytes under similar conditions, thus providing support that the Hrnr siRNA utilized in the presently disclosed studies was mouse-specific (FIG. 6B). Remarkably, intratumoral injections of Hrnr siRNA resulted in tumors that were 2.5-fold smaller compared to tumors that were injected with Scr siRNA (FIG. 7A).

Figure 7B:
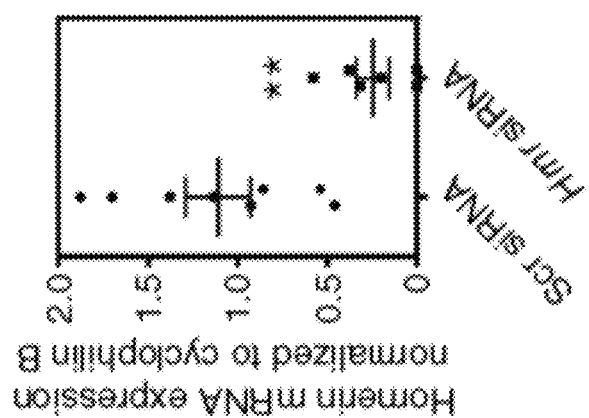
Figure 7C:
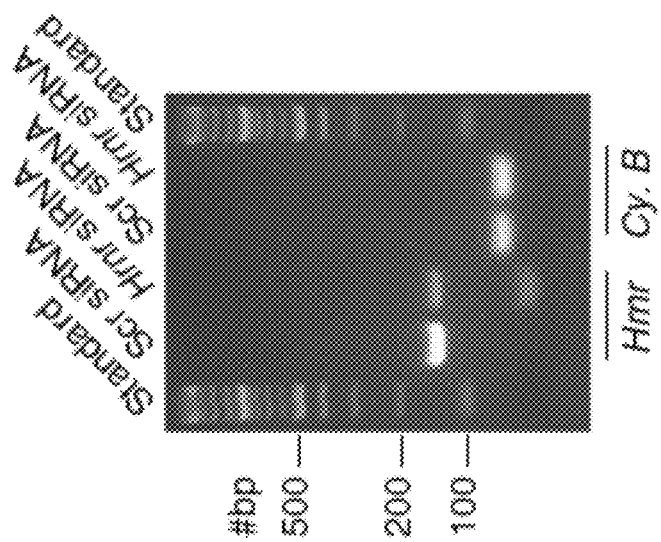

To confirm hornerin knockdown in the tumor endothelium, quantitative PCR (qPCR) was performed on fluorescence-activated cell sorting (FACS) sorted tumor $CD31^+$ $CD45^-$ cells and a marked 78% reduction in hornerin transcript in the Hrnr siRNA-treated cohort was observed (FIG. 7B). Analysis of qPCR end-point samples revealed an intense band at the predicted amplicon size (149 base pairs), indicating that the primers employed were specific for the intended target (FIG. 7C).

Figure 7D:
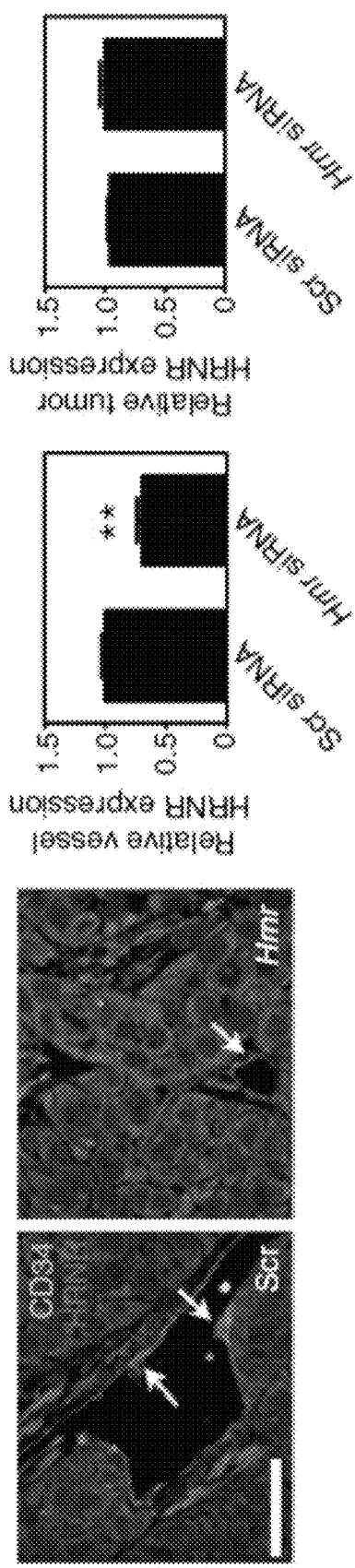
Figure 8:
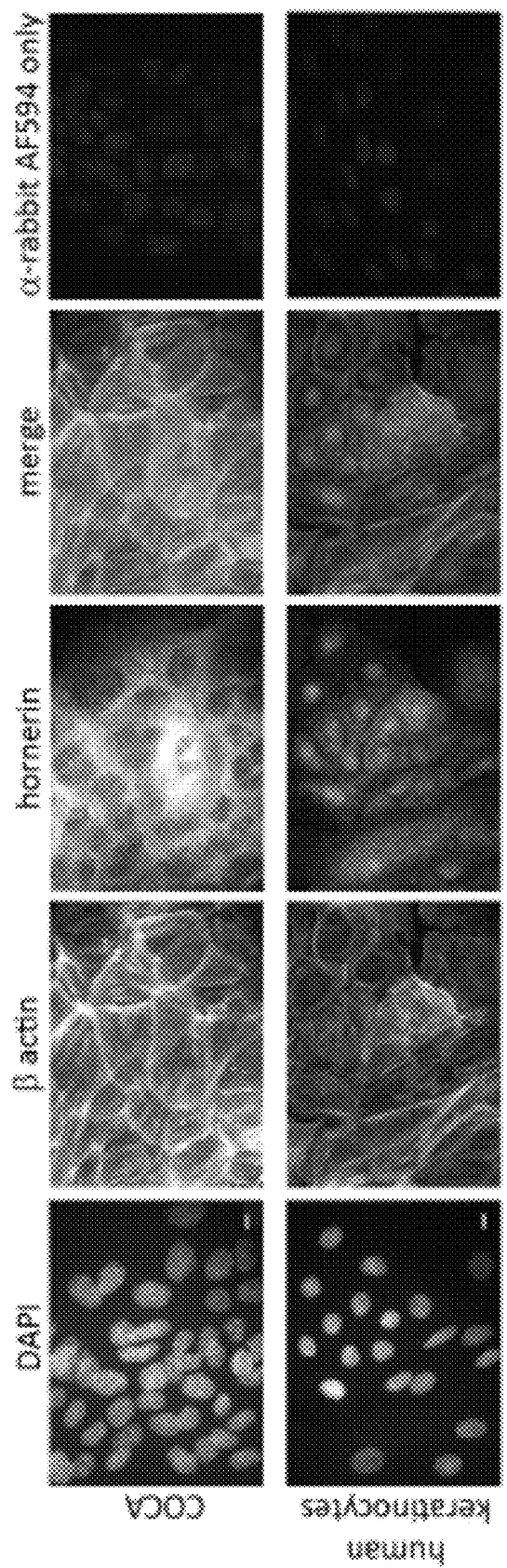
FIG. 8. The anti-hornerin antibody utilized for indirect fluorescent microscopy of tumor sections cross-reacts with murine hornerin. COCA or human keratinocytes were seeded onto fibronectin coated coverslips and treated with 2 mM $CaCl_2$) for two days, followed by incubation with anti-hornerin and anti-beta actin FITC primary antibodies. The samples were subsequently incubated with the secondary antibody anti-rabbit AF594 prior to mounting with Prolong Gold+DAPI. Representative images depict hornerin expression (red, merged image) in both COCA (top row) and human keratinocytes (bottom row). Scale bar=10 μm.

To provide further support for endothelial cell-hornerin knockdown and targeted siRNA specificity for murine and not human hornerin, tumor sections were analyzed for hornerin protein expression by immunofluorescent microscopy. Tumor vessels treated with Scr siRNA maintained high expression of hornerin, while hornerin expression in Hrnr siRNA-treated vessels was greatly reduced (FIG. 7D). Quantitation of sections revealed no difference between the expression of hornerin in epithelial cells from tumors treated with either Scr siRNA or Hrnr siRNA. In contrast, there was a 30% decrease in hornerin expression in the endothelial cells between the two treatments (FIG. 7D). Antibody cross-reactivity to mouse hornerin was confirmed through indirect immunofluorescent microscopy in COCA cells and human keratinocytes (FIG. 8).

Example 6

Hornerin Knockdown Altered Key Tumor Vessel Parameters

Figure 9A:
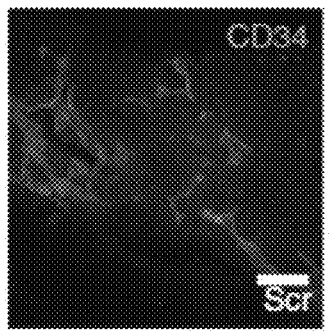
FIGS. 9A-9F: siRNA-mediated hornerin knockdown results in altered tumor vessel parameters.
Figure 9A:
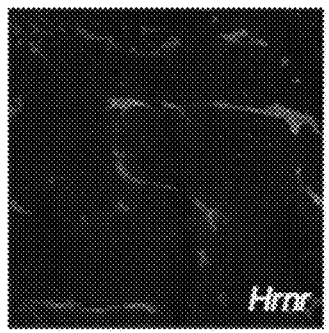
Figure 9B:
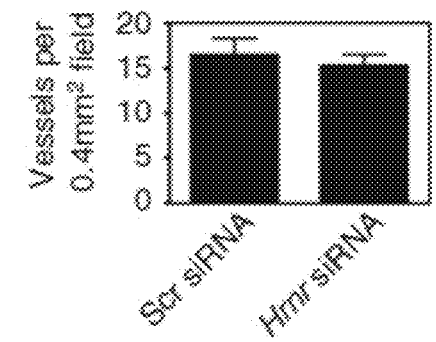
Figure 9C:
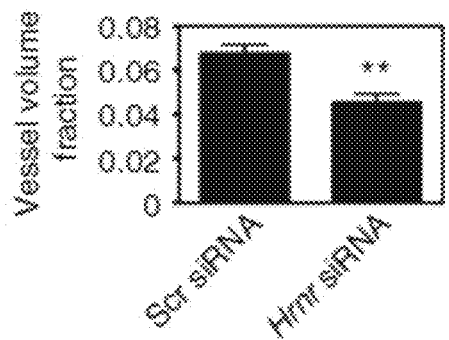
Figure 9D:
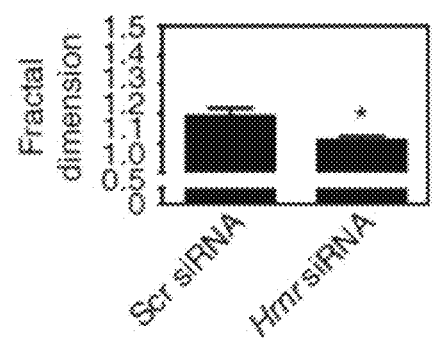
Figure 9E:
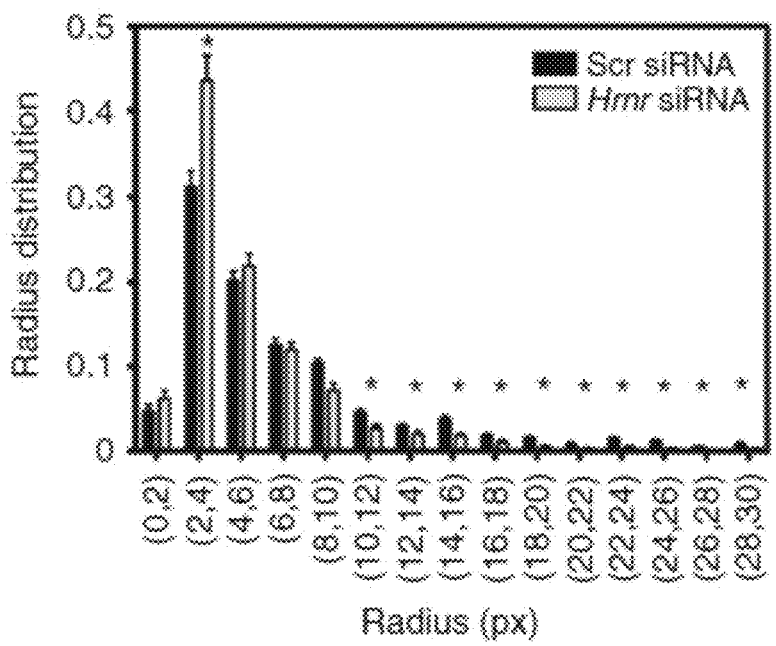

The matrix laboratory (MATLAB)-based vessel analysis software program rapid analysis of vessel elements (RAVE; Seaman et al., 2011) was employed to measure vessel volume fraction (VVF), fractal dimension (a measure of tortuosity), and vessel radius, parameters commonly evaluated in tumor vasculature (Carmeliet & Jain, 2011) Immunofluorescent analysis of tumor sections revealed that vessels in Hrnr siRNA-injected tumors had drastic differences in appearance, notably smaller radius and length and reduced tortuosity (FIG. 9A). Interestingly, the number of vessels per field (FIG. 9B) and the proportion of endothelial cells ($CD31^+/CD45^-$), as determined by FACS (FIGS. 10A and 10B), were not different. Hrnr siRNA injection reduced VVF and fractal dimension as well (FIGS. 9C and 9D). Additionally, there was an overall reduction in vessel radius from larger to smaller vessels (FIG. 9E).

To confirm that the results were not due to off target effects of Hrnr siRNA, a second set of tumor-bearing mice was treated with Scr siRNA or a pool of three additional mouse Hrnr siRNA and analyzed similar vessel parameters by immunofluorescent microscopy. A trend toward smaller vessel radii and a reduction in vessel volume and fractal dimension in the Hrnr siRNA group relative to control was again observed (FIGS. 11A-11D).

Figure 9F:
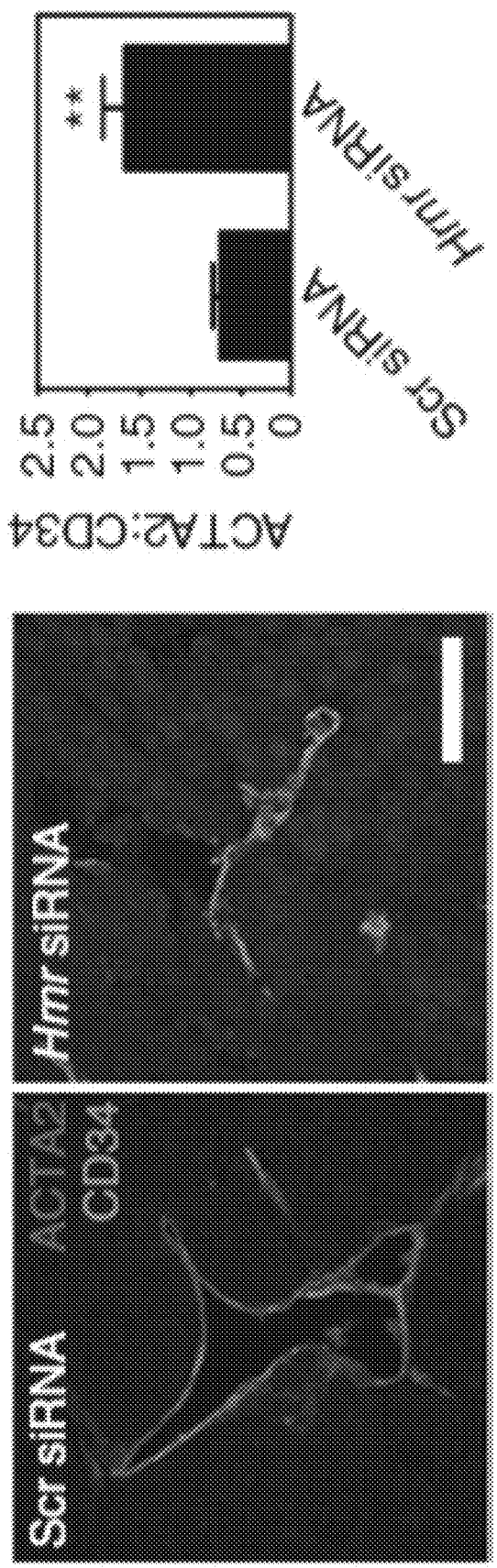

A mature vessel is typically highly invested with alpha-smooth muscle actin (ACTA2)-positive pericytes (Yonenaga et al., 2005; Carmeliet & Jain, 2011). Conversely, tumor vessels typically lack pericyte investment and evidence suggests that pericyte-endothelial interactions could play a role in vessel morphology and functionality in tumors (Carmeliet & Jain, 2011). Upon injection of endothelial-targeted Hrnr siRNA, a 2.3-fold increase in ACTA2 coverage of vessels when compared with Scr siRNA (FIG. 9F) was observed, a result similar to previous reports (Hamzah et al., 2008). The cumulative data suggested that hornerin was not required to maintain the number of tumor vessels, however important vessel parameters such as VVF, tortuosity, pericyte recruitment, and radius were altered by the downregulation of hornerin expression.

Example 7

Altered Tumor Vessel Function with Hrnr siRNA Treatment

Tumor vessels serve as an important supply line to a growing tumor. Consequently, disruption of this supply line should reduce tumor volume—the major hypothesis behind anti-angiogenesis therapies. Ex vivo vessel parameters such as vessel number, VVF, and vessel radius provide excellent insight into the structural and anatomic changes that occur as a result of therapeutic intervention, However, in vivo functional studies of tumor vascularity and perfusion are needed to determine if the delivery of oxygen and nutrients is actually reduced.

Figure 12A:
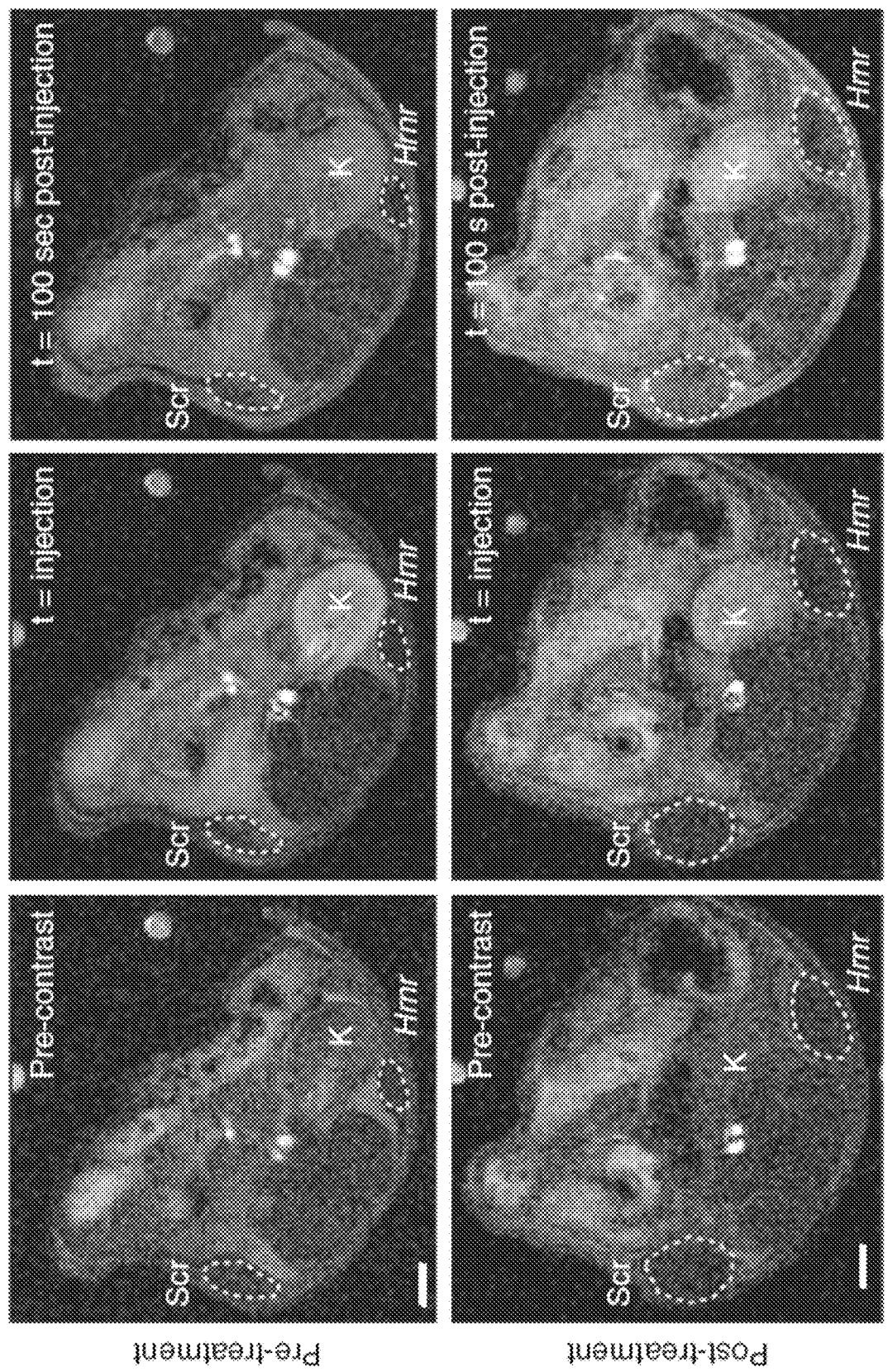
FIGS. 12A-12C: Dynamic contrast-enhanced magnetic resonance imaging revealed decreased vascularity and perfusion in Hrnr siRNA-treated mice compared to control mice.
Figures 12B, 12C:
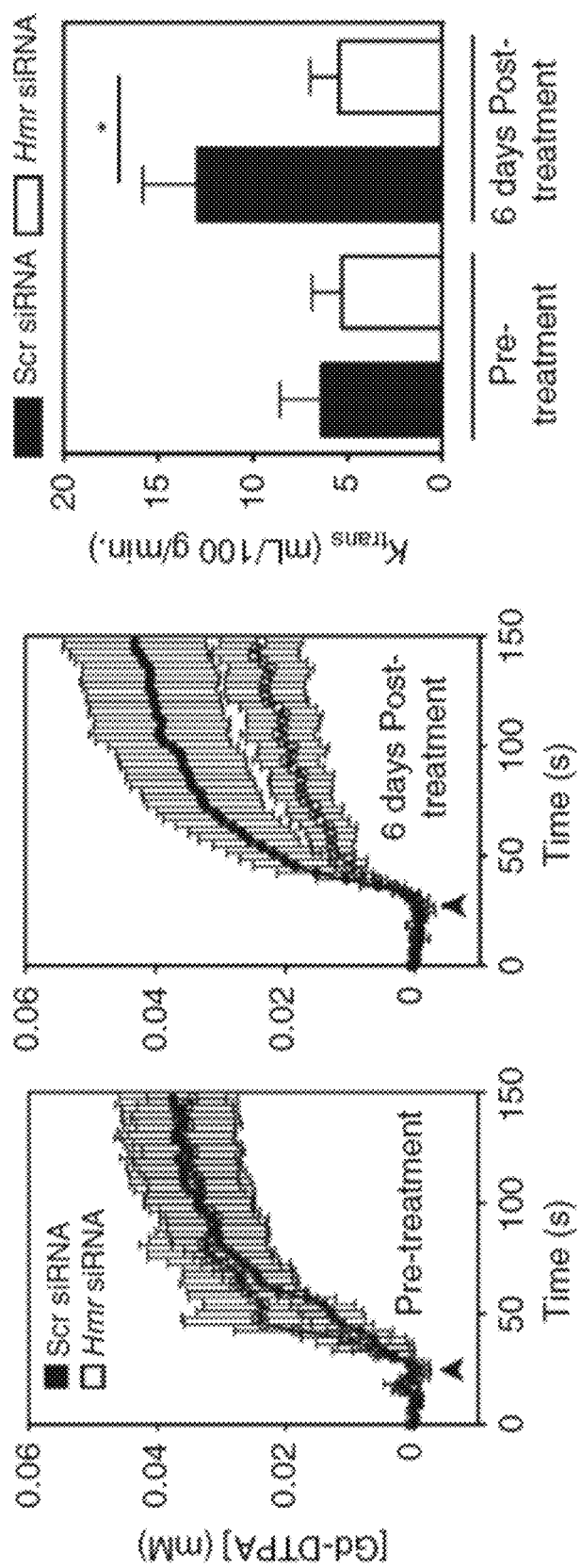

Therefore, tumors were treated with Scr or Hrnr siRNA and functional changes were measured through dynamic contrast-enhanced (DCE) MRI (Barnes et al., 2012). Mice were imaged before treatment to establish baseline levels of vascularity. No difference was observed in the pre-treatment images (FIG. 12A; top row) as determined by gadolinium-diethylenetriamine penta-acetic acid (contrast agent, Gd-DTPA) time intensity curves (FIG. 12B; left) or volume transfer coefficient ($K_{trans}$; FIG. 12C; left). After pre-treatment imaging, tumors were randomly assigned to Scr or Hrnr siRNA treatment groups. Although tumors did not receive treatment prior to pre-treatment scans, they are labeled as Scr or Hrnr to indicate their subsequent treatment designation in FIG. 12A (lower row), FIG. 12B (right), and FIG. 12C (right). Importantly, after just 6 days of treatment (siRNA injection every other day), large differences in Gd-DTPA accumulation and $K_{trans}$ values were observed in Scr and Hrnr siRNA-injected tumors. After 100 seconds, Gd-DTPA signal intensity was elevated in the Scr siRNA-treated tumors compared to the Hrnr siRNA treated tumors (FIG. 12A; third column). The Gd-DTPA time intensity curves separated 15-20 seconds after injection and tumor concentration of Gd-DTPA remained two-fold reduced in Hrnr siRNA-injected tumors through the entire time course (FIG. 12B; right). Likewise, after 6 days of siRNA injections, a 2.4-fold reduction in $K_{trans}$ was observed in hornerin knockdown tumors compared to control (FIG. 12C; right).

Figure 13A:
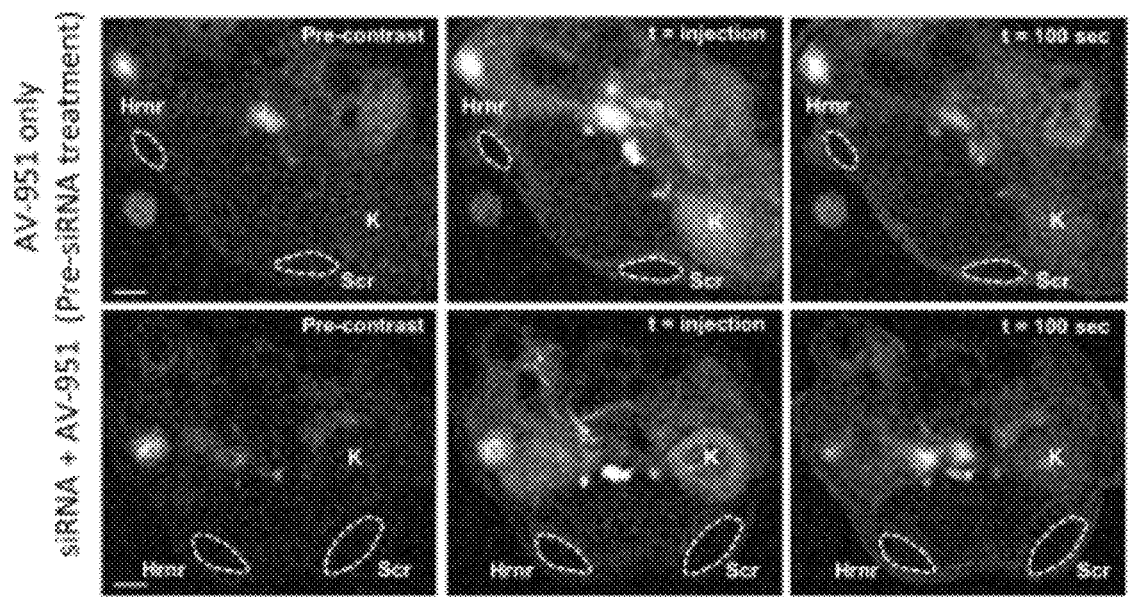
FIGS. 13A-13C. Dynamic contrast-enhanced magnetic resonance imaging of L3.6pl tumors treated with AV-951 or AV-951+siRNA.
Figure 13B:
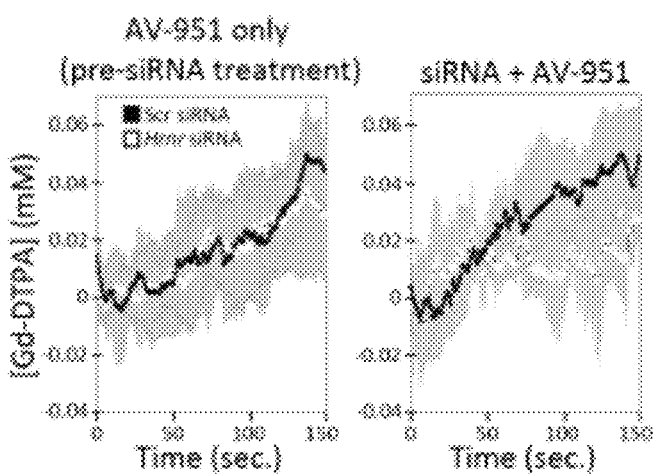
Figure 13C:
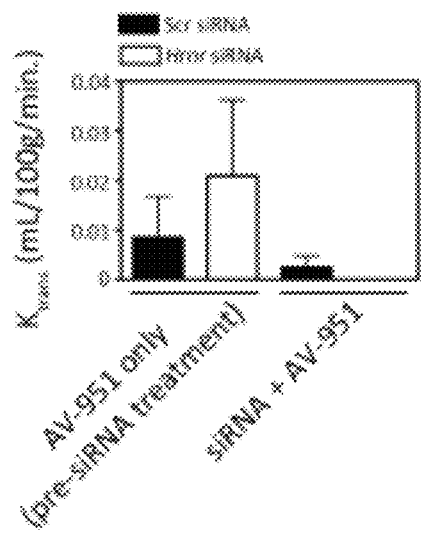

As a control, a VEGFR2 inhibitor (AV-951, tivozanib; AVEO Pharmaceuticals, Inc., Cambridge, MA, USA) currently in Phase II clinical trials (Nakamura et al., 2006; Nosov et al., 2012) was employed. This therapeutic strategy has been shown in numerous models to alter the tumor vasculature and reduce perfusion (Kiessling et al., 2004; Nielsen et al., 2012). As expected, there was a decrease in the $K_{trans}$ values in the AV-951 only treated animals when compared with control; a result congruent with previously published data (compare FIG. 12C (pre-treatment) to FIG. 13C (pre-treatment)). Although $K_{trans}$ values between AV-951 and the combination hornerin siRNA and inhibitor group were not significantly different, there was a trend toward a further decrease in $K_{trans}$ value for the combination therapy of AV-951 and Hrnr siRNA (FIG. 13C). These data confirmed that knockdown by Hrnr siRNA treatment resulted in reduction of both structural and functional parameters of tumor vasculature as well as reduced tumor outgrowth.

Example 8

Hornerin Knockdown and VEGFR Inhibitor Combined Treatment

As it was possible to decrease tumor size, vessel parameters, and vessel function with targeted hornerin knockdown, whether the combination of this approach with VEGFR inhibition would produce an enhanced therapeutic response was examined. The treatment schedule used is outlined in FIG. 14A. As previously shown (Nakamura et al., 2006), AV-951-treated mice exhibited tumor volumes that were decreased 2.3-fold compared to control-treated animals (FIG. 14B). Notably, treatment with Hrnr siRNA and AV-951 (combo) resulted in a 4.3-fold decrease in volume compared to the control group, indicating that inhibition of VEGF combined with hornerin knockdown resulted in an additive reduction in tumor growth (FIG. 14C). Notably, it was observed that the most dramatic effect of hornerin knockdown occurred at the later stages of tumor outgrowth (days 11-14; FIG. 15).

Figure 10A:
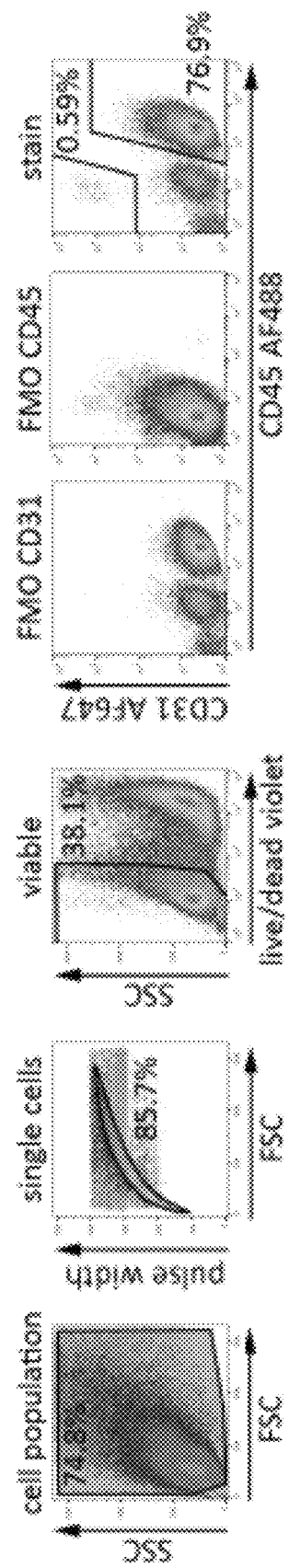
FIGS. 10A-10C. Identification of tumor cell populations by fluorescence activated cell sorting (FACS).
Figure 10B:
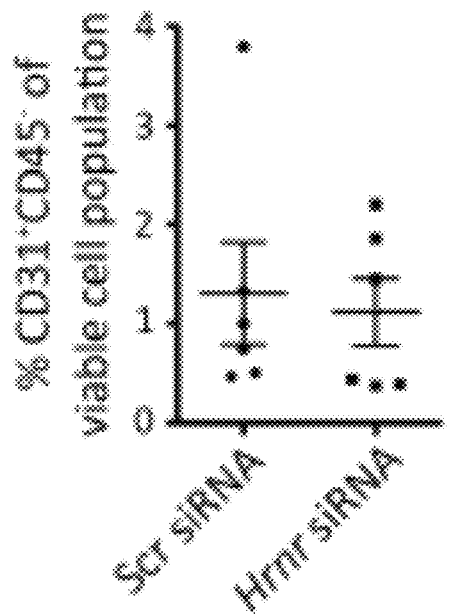
Figure 10C:
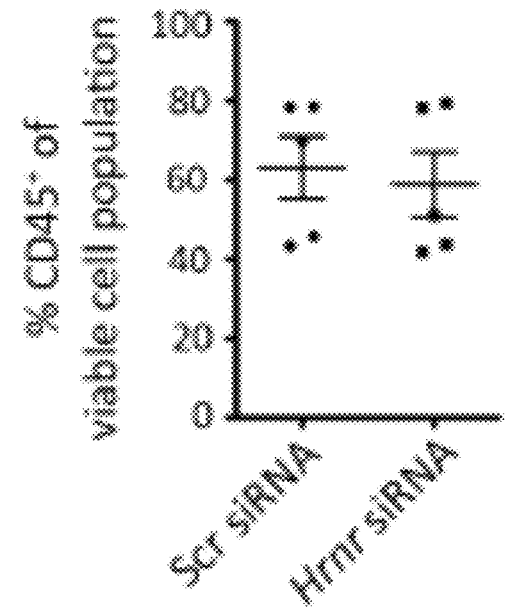
Figure 11A:
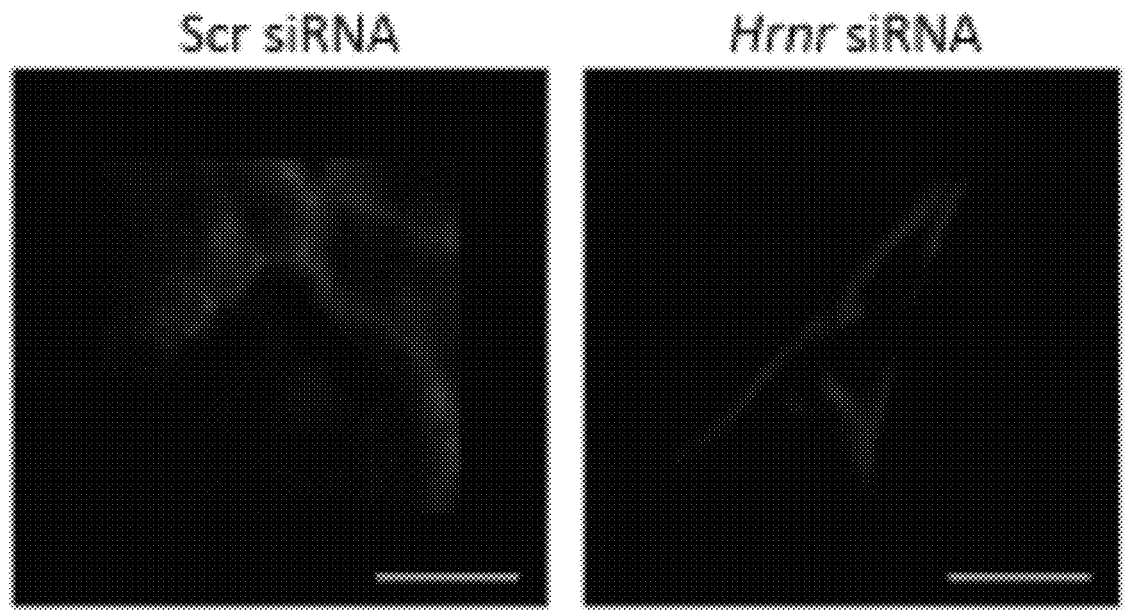
FIGS. 11A-11D. The tumor vasculature of L3.6pl tumor bearing mice treated with a second unique set of pooled Hrnr siRNA (Origene; SEQ ID NOs: 50-52) display a trend-toward smaller radii, reduced volume fraction, and reduced fractal dimension compared to mice treated with Scr siRNA (Origene).
Figure 11B:
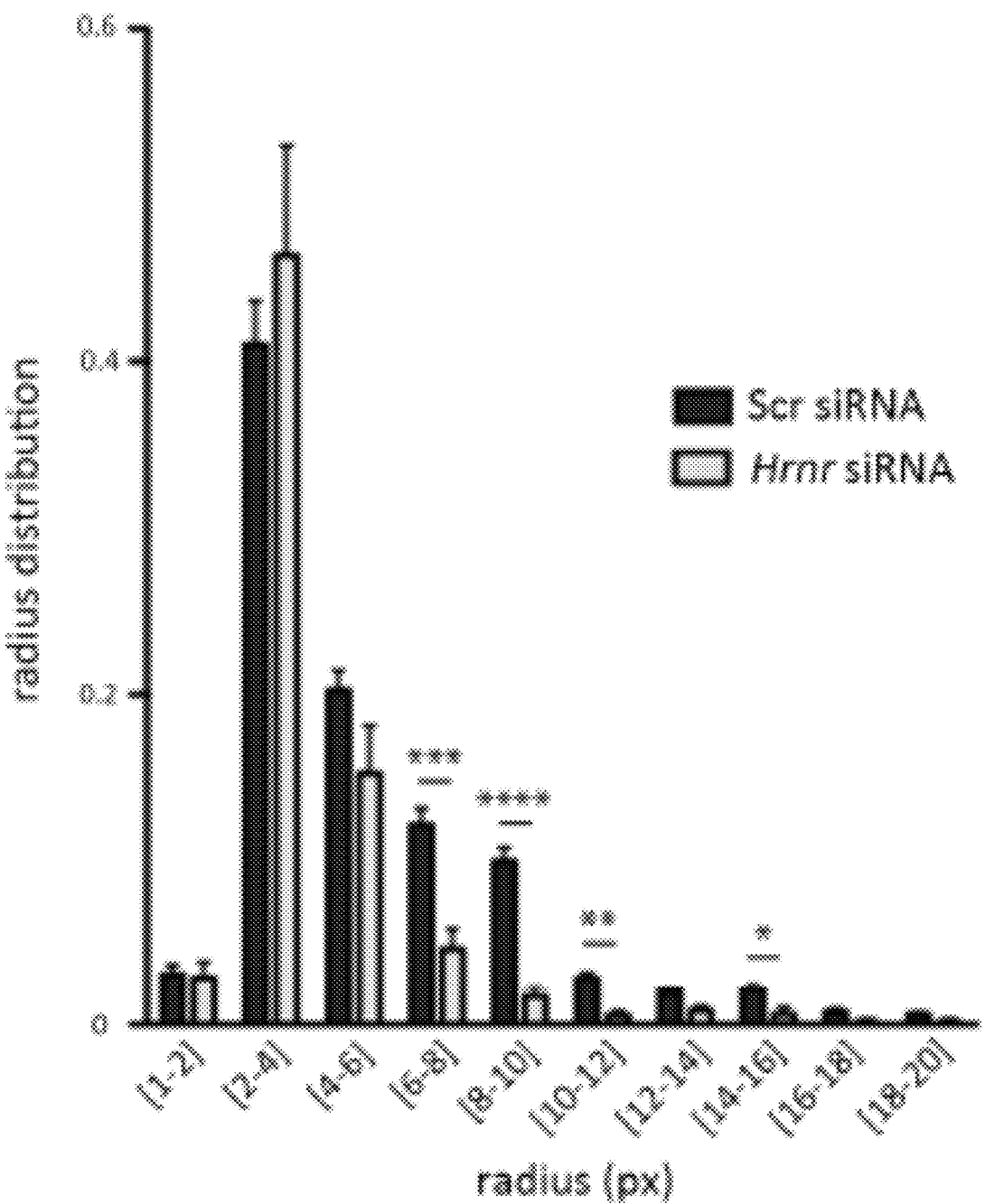
Figure 11C:
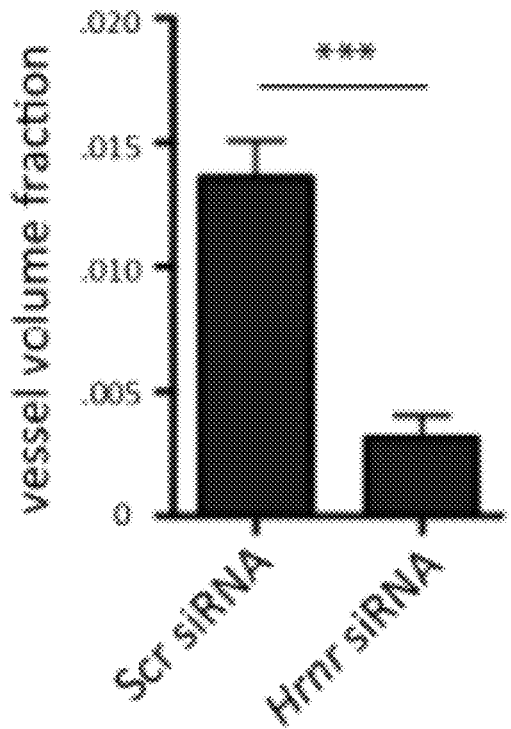
Figure 11D:
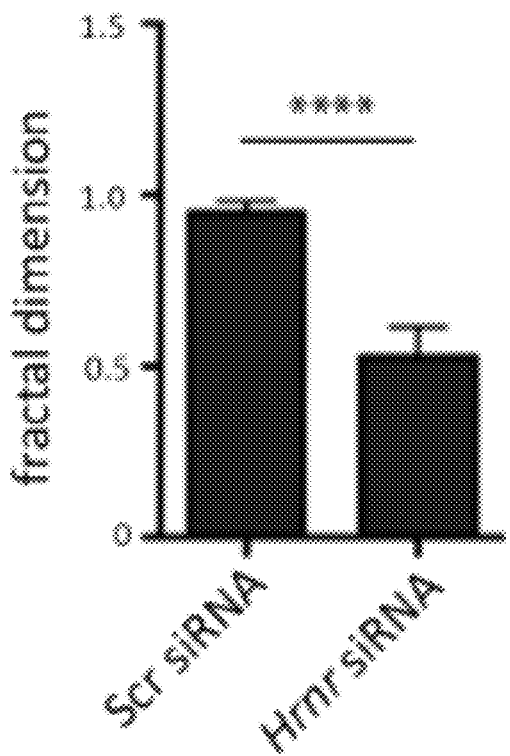
Figure 16A:
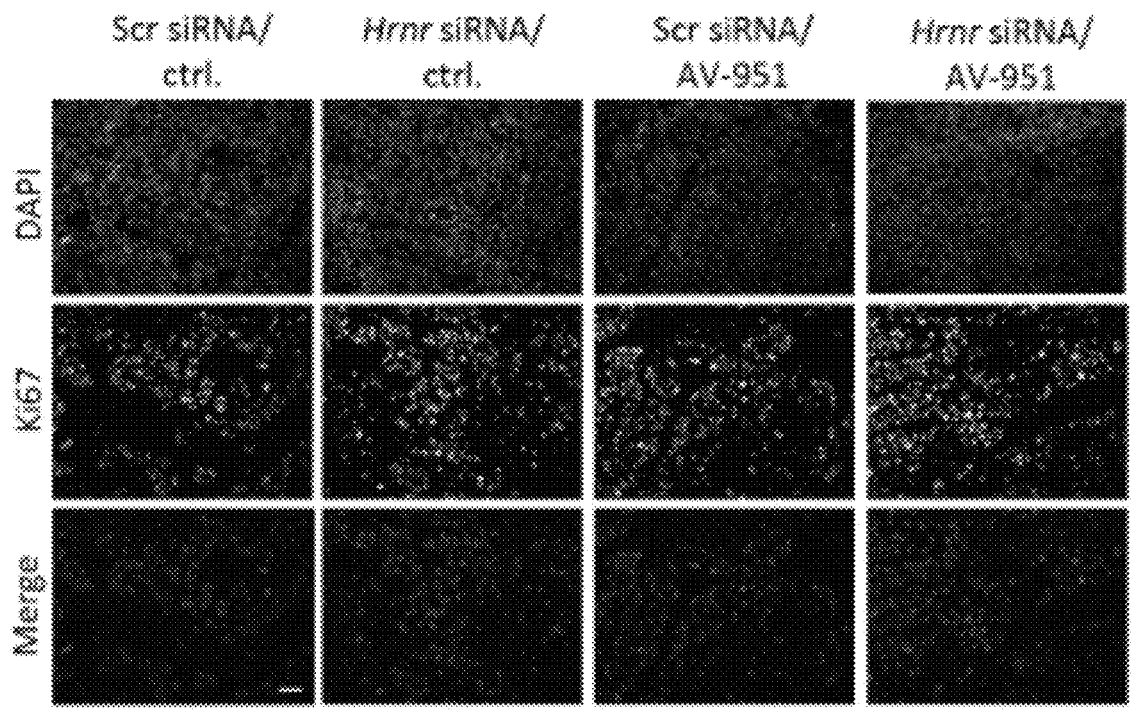
FIGS. 16A-16D. Tumors from Hrnr siRNA or VEGFR inhibitor treated mice display similar expression of Ki67 and elevated cleaved caspase 3. Formalin-fixed day 15 tumor sections from each of the four treatment groups were deparaffinized, rehydrated, and incubated with an anti-Ki67 or anti-cleaved caspase 3 primary antibody. Following a secondary antibody incubation with anti-rabbit AF594, the sections were mounted in Prolong Gold+DAPI and images were acquired at 20× magnification.
Figure 16B:
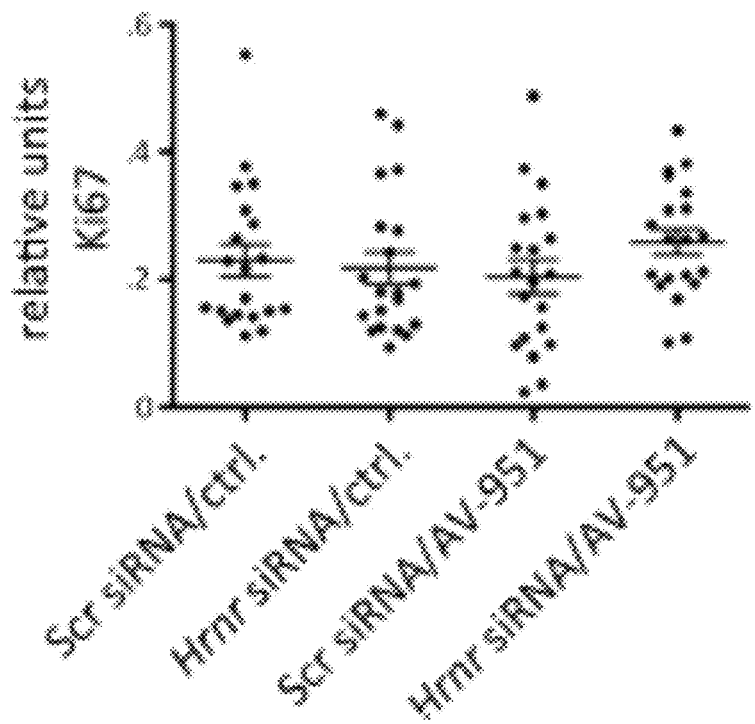
Figure 16C:
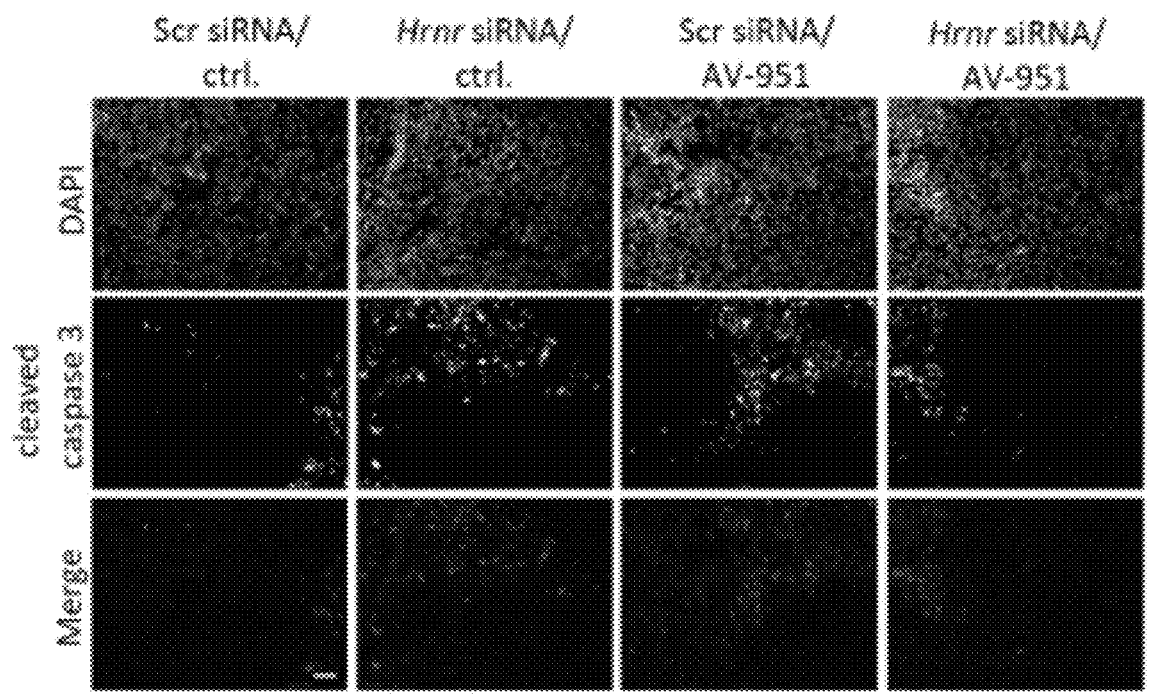
Figure 16D:
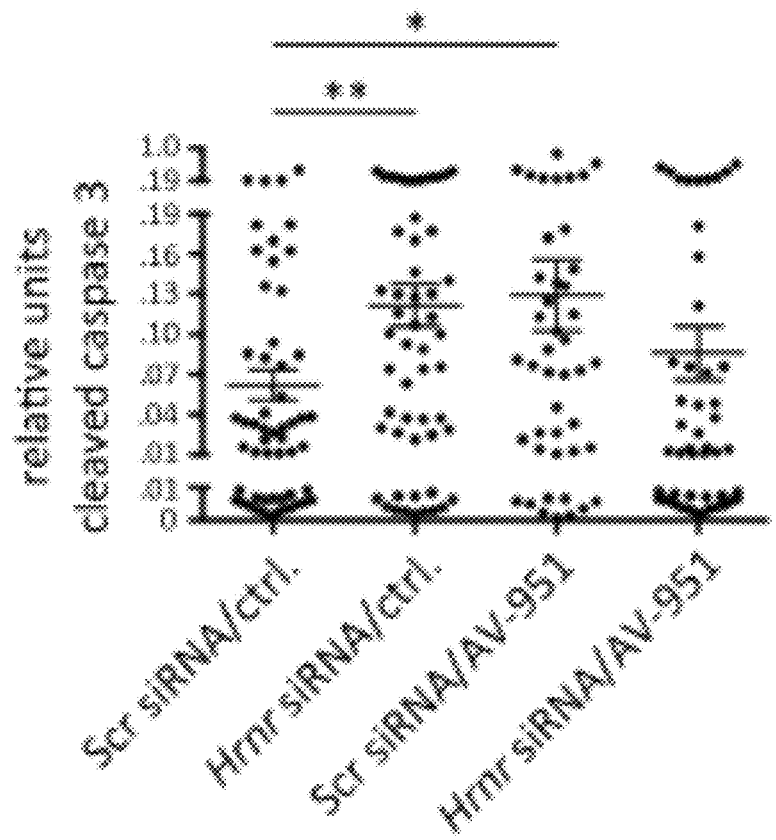

To determine if the reduced tumor burden observed in the monotherapy and combo groups was attributable to a lower degree of cell proliferation and/or enhanced cell death, expression of Ki67, a proliferation marker, and cleaved caspase 3, a marker of cellular apoptosis, were analyzed in tumor sections by immunofluorescent microscopy. The results indicated that neither hornerin knockdown nor VEGFR inhibition altered overall tumor proliferation in either of the three treatment groups compared to control (FIGS. 16A and 16B). Interestingly, a two-fold increase relative to control in cleaved caspase 3 levels in tumors that had been treated with Hrnr siRNA or AV-951 alone was observed, suggesting that enhanced apoptosis in the tumor might be responsible for the decreased tumor burden observed in these two groups (FIGS. 16C and 16D). No significant difference from control was observed in tumors with combination treatment. Further analysis of the tumor cellularity indicated that the proportion of leukocytes ($CD45^+$/$CD31^-$ cells) was not altered with hornerin knockdown, suggesting that immune cell infiltration into the tumor was not hornerin-dependent (FIGS. 10A and 10C). Additionally, there were no observable differences in metastases between the groups.

Figure 14D:
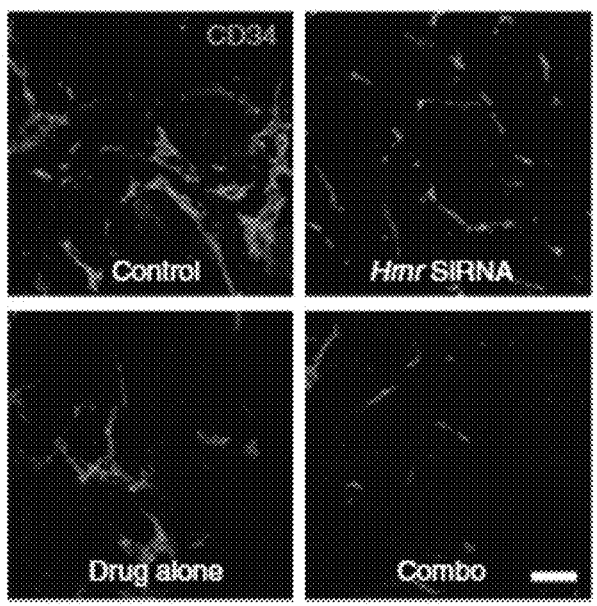
Figure 14E:
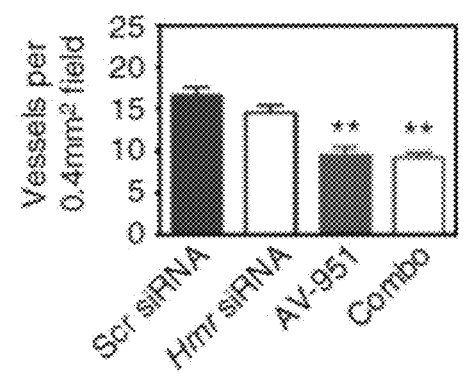
Figure 14F:
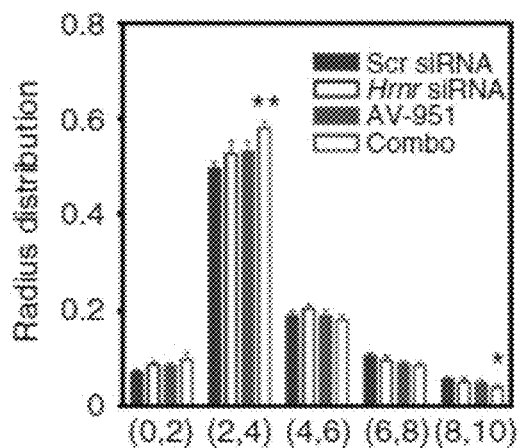
Figure 14G:
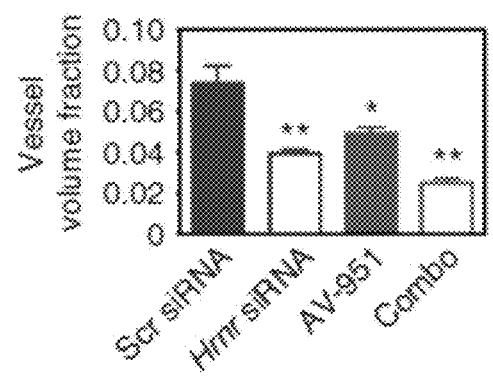
Figure 14H:
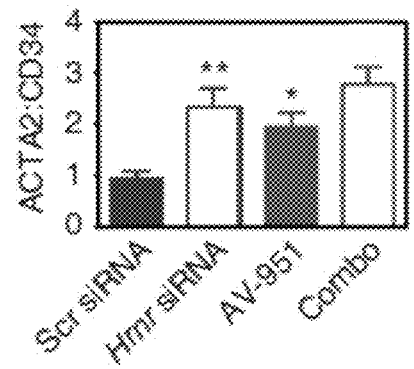
Figure 15:
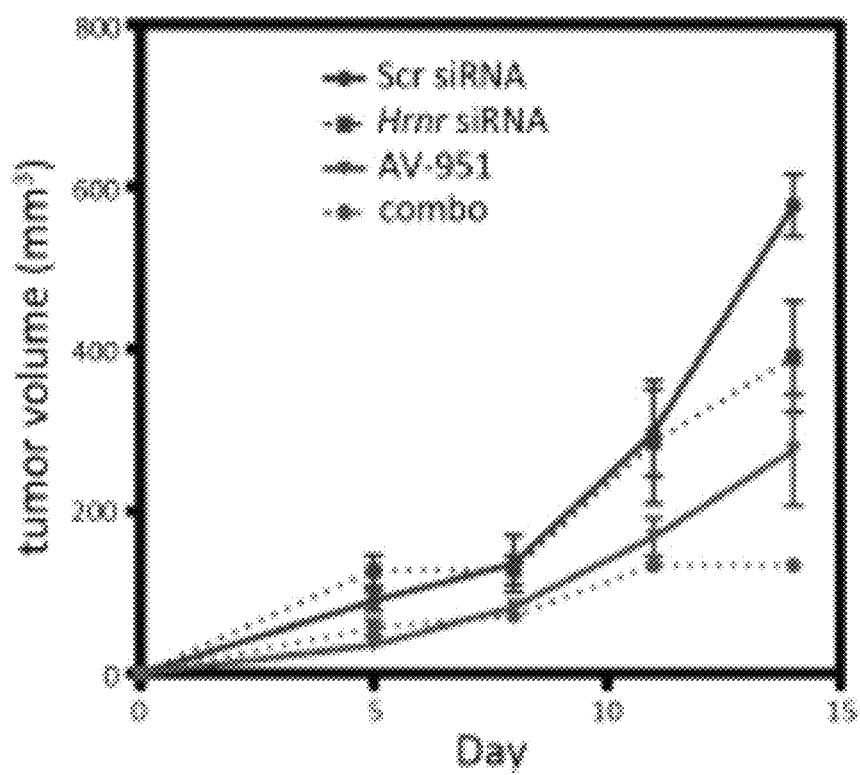
FIG. 15. L3.6pl tumor outgrowth. Complete outgrowth curves for the four treatment groups. N=3 (Scr siRNA), N=4 (Hrnr siRNA, AV-951, combo). Graphs represent mean+/− SEM.

The vessels from each treatment group were morphologically distinct (FIG. 14D). Control tumors had typical tumor vasculature: numerous, large, irregular vessels. As expected, Hrnr siRNA treatment resulted in vessels with smaller radii and tortuosity, but no change in the number of vessels per field (FIGS. 14E-14G). As previously published at this concentration (Nakamura et al., 2006), vessels from AV-951 alone treated tumor-bearing animals were morphologically similar to control vessels; however, fewer vessels were observed. The combination therapy of Hrnr siRNA and AV-951 resulted in fewer vessels in addition to morphologic differences in the vessels. Quantitation with RAVE revealed the presence of an overall shift to smaller radii and VVF in the combo group compared to control, and a trend toward increased pericyte coverage (FIG. 14H).

Figure 17A:
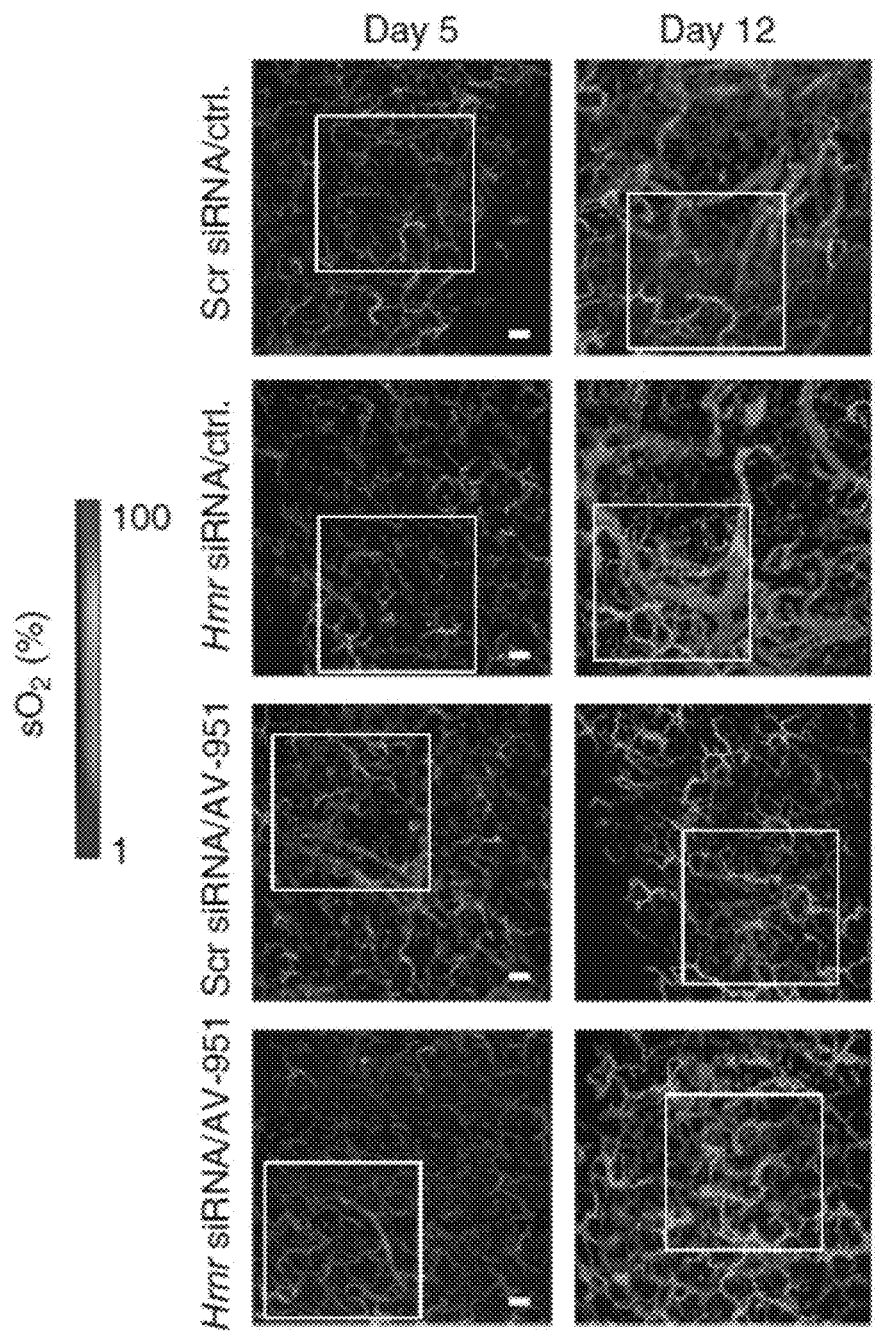
FIGS. 17A and 17B: Hrnr siRNA and VEGFR inhibitor-treated mice display elevated hemoglobin oxygen saturation relative to control Scr siRNA mice.
Figure 17B:
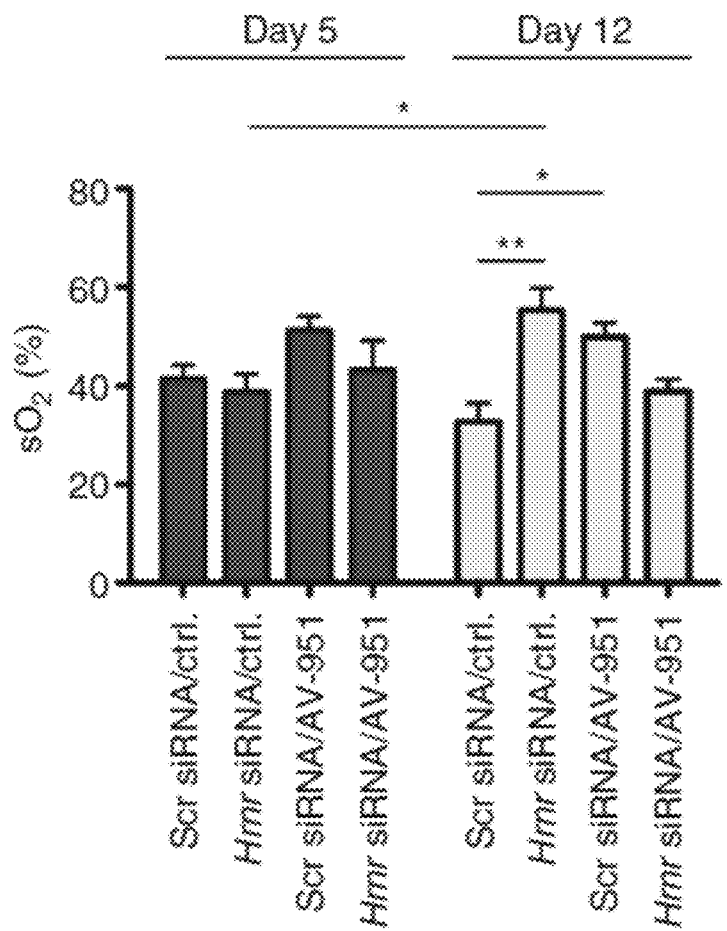

Hornerin regulation of tumor vasculature was also evaluated through photoacoustic microscopy (PAM), which permitted non-invasive analysis of critical vessel parameters such as blood flow rate, hemoglobin, and oxygen saturation in the same tumor over the course of treatment. The data revealed that prior to hornerin knockdown and 4 days post initiation of AV-951 treatment, there was no difference in either tumor blood hemoglobin or oxygen saturation as determined by PAM (FIGS. 17A and 17B; day 5). However, while hemoglobin levels remained unchanged in tumors following hornerin knockdown and continued VEGFR inhibition, we did observe that oxygen saturation was elevated in the Hrnr siRNA (1.7-fold) and AV-951 (1.5-fold) cohorts compared to control (FIGS. 17A and 17B; day 12). This difference was notably ablated in the combination treatment group. These data indicated that in the presently disclosed model, hornerin knockdown and VEGFR inhibition alone functioned to increase tumor blood oxygen levels, and provided additional evidence that critical parameters of tumor vasculature were modulated by hornerin.

Discussion of the Examples

Despite preclinical and clinical successes, anti-angiogenic therapies, many of which focus on VEGF inhibition, have been hampered by acquired resistance mechanisms. It was hypothesized that redundant signaling pathways exist in the tumor vasculature that circumvent monotherapies, and that the identification of VEGF-independent regulatory proteins might provide targets for dual anti-angiogenic treatment modalities. To identify these potential targets, phage display screening and functional proteomics methods were employed, primarily because of their enormous potential to find unbiased targets with no a priori knowledge. Functionalizing the phage for use as a proteomics tool has so far identified novel proteins in PDAC such as pyruvate kinase M2 and plectin—both of which are normally cytoplasmic but are secreted and cell surface associated in cancer, similar to our findings with hornerin (Reynolds et al., 2011). Of the identified proteins, plectin is the most studied and developed biomarker for PDAC and its importance in tumor biology was recently illuminated (Shin et al., 2013). Since the original discovery as a PDAC biomarker, plectin has been published as being expressed in other diseases such as bladder (Sutoh Yoneyama et al., 2014), head and neck squamous cell carcinoma (Katada et al., 2012), and esophageal cancer (Pawar et al., 2011), indicating that the presently disclosed phage-based functional proteomics methods are robust and can lead to the identification of proteins of importance. After three rounds of in vivo phage screening, validation in vitro, and phage-based functional proteomics, hornerin was identified as a non-VEGF upregulated protein differentially expressed in tumor vessels. From this screen, other potentially interesting peptides were also identified with their binding partners.

The identification of elevated hornerin expression in this setting is novel and contributes significantly to the relatively small volume of literature on hornerin regulation and function. Hornerin is a member of the S100 family of proteins, a group of calcium binding proteins involved in the maintenance of calcium homeostasis, as well other fundamental cellular processes and signaling cascades (Marenholz et al., 2004; Kizawa et al., 2011; Kypriotou et al., 2012). Several family members have been implicated in a variety of cancers (Hauschild et al., 1999; Gupta et al., 2003), and significant attention has been directed to their role in receptor for advanced glycation end products activation (Donato, 2001; Leclerc et al., 2009; Xie et al., 2013). The initial hornerin studies focused on expression in the cornified epidermal layer and regulation in chronically psoriatic skin (Makino et al., 2001; Makino et al., 2003; Takaishi et al., 2005). Subsequent, but limited, investigation has addressed the intersection of hornerin with cancer, as highlighted in a recent report (Fleming et al., 2012) that showed increased hornerin expression in the development of murine mammary glands and in breast tumor cells associated with high tumorigenicity. Hornerin had not been evaluated in endothelial cells prior to this study, and the identification of hornerin specifically on the endothelium adjacent to pancreatic tumor outgrowth directed an investigation of its function under conditions found in a growing tumor.

The in vivo reduction of endothelial hornerin expression by intratumoral siRNA injection resulted in tumors with vessels that were morphologically distinct: characterized by smaller radii and reduced tortuosity. Further, tumor vessel function was measured using DCE-MRI, a non-invasive tool to track tumor vessel development (Nakamura et al., 2006; O'Connor et al., 2007; Turkbey et al., 2010) and investigate vascularity and perfusion. The results showed decreased Gd-DTPA uptake and decreased $K_{trans}$ value in tumors treated with Hrnr siRNA, suggesting that hornerin knockdown resulted in both structural and functional vascular changes that led to decreased tumor growth. Further, tumors with decreased hornerin expression had higher oxygen saturation levels. Elevated tumor blood oxygen is a characteristic of patients who display improved prognosis and survival following anti-angiogenic and other treatment modalities, however this does not appear to be a universal phenomenon (Biswal et al., 2011; Ueda et al., 2012; McCormack et al., 2014). Other reports indicated that newly diagnosed glioblastoma patients who are responsive to the VEGFR kinase inhibitor cediranib display improved perfusion and oxygen delivery to the tumor, and also highlight the application of advanced imaging techniques to better understand the interplay of tumor oxygen status with tumor growth and response to therapy (Batchelor et al., 2013; Emblem et al., 2013). The data presented herein showing that hornerin alters tumor perfusion and blood oxygen saturation suggested that it could be involved mechanistically at several regulatory nodes that govern tumor oxygen status.

Finally, the combination therapy results disclosed herein coincided with an emerging body of evidence that suggests that compensatory pathways could additionally be responsible for non-durable clinical results when targeting VEGF (Bergers & Hanahan, 2008). Anti-vascular therapies, which are almost always synonymous with VEGF inhibitors, have achieved success pre-clinically and clinically and have opened new avenues for anti-tumor therapy (Kindler et al., 2011; Lang et al., 2013). However, the durable patient response and efficacy have been marginal, measuring increased patient survival in months. Of the tumors that respond, most recur and are no longer responsive to anti-VEGF therapy (Shojaei, 2012). One hypothesis could be the presence of compensatory or redundant pathways, which are well established in tumor therapy research. Consequently, clinical trials devoted to synergistic combinations of drugs have proliferated (Al-Lazikani et al., 2012; Baselga et al., 2012), although most are aimed at pathways present in the cancer cells. Compensatory pathways involving the VEGF and fibroblast growth factor (FGF) pathways have been described in tumor vessel studies (Casanovas et al., 2005). An approach involving both the VEGF pathway and another important pathway could provide increased positive therapeutic outcomes. The existence of VEGF-independent compensatory pathways is an emerging concept that has been investigated by, among others, the Hanahan group. Recent evidence suggests that activation of the FGF2 pathway could constitute a potential resistance mechanism to anti-VEGF therapy (Casanovas et al., 2005). When FGF2 signaling was blocked by FGF2 trap, resistance to the anti-VEGFR2 antibody DC101 was eliminated (Casanovas et al., 2005). In further studies by the same group, brivanib, a dual VEGF/FGF inhibitor, suppressed anti-VEGF (DC101 and sorafenib)-acquired resistance (Allen et al., 2011).

To expand on this concept, whether decreasing hornerin protein levels in combination with VEGFR2 inhibition would produce synergistic or additive reductions in tumor volume was investigated. Each monotherapy—hornerin knockdown and VEGFR inhibition—produced a two-fold reduction in tumor volume. When the therapies were combined, the resulting decrease in tumor volume was four-fold. Interestingly, tumor-cleaved caspase three levels were elevated with either treatment alone but not in mice subjected to combination therapy, suggesting that perhaps hornerin knockdown and VEGFR inhibition synergized through a yet unidentified mechanism to induce stasis of tumor growth during the early stages of progression. The identification of hornerin and its additive effects in combination with VEGF inhibition represents a promising avenue for development of targeted therapeutics against hornerin.

Figure 18A:
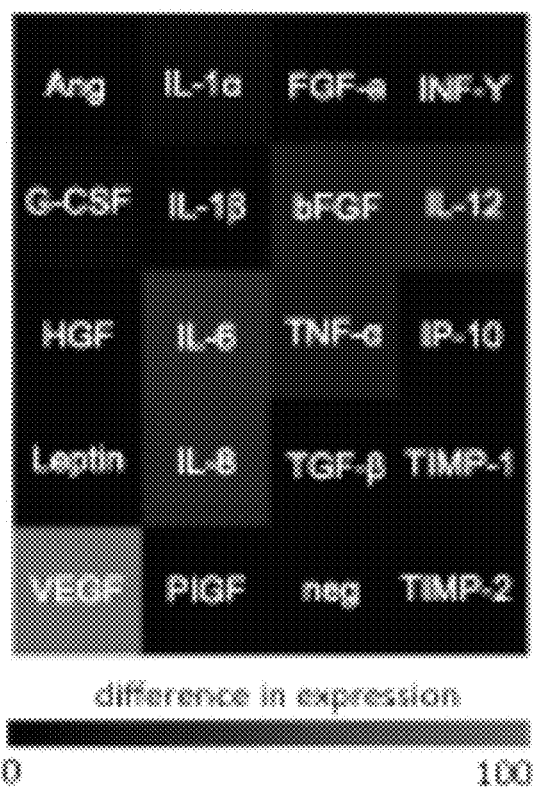
FIGS. 18A-18E. The regulation of hornerin expression by factors present in the tumor secretome.
Figure 18B:
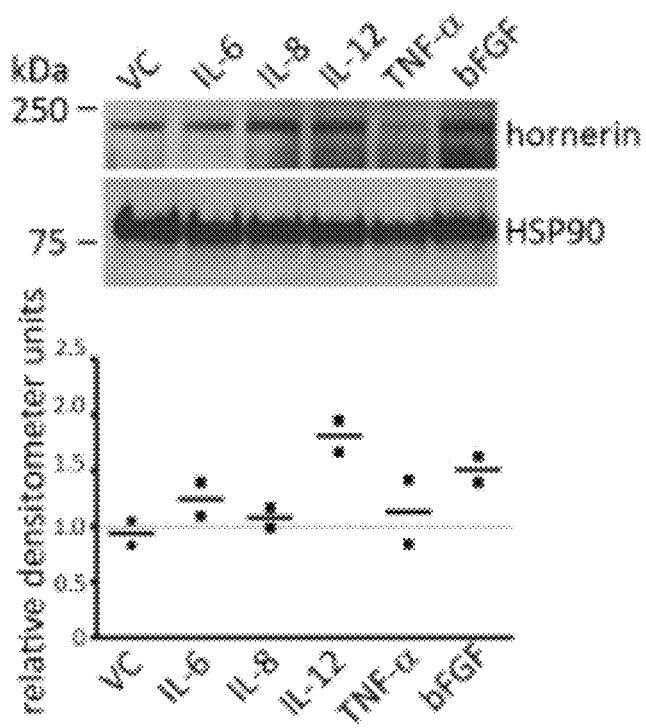
Figure 18C:
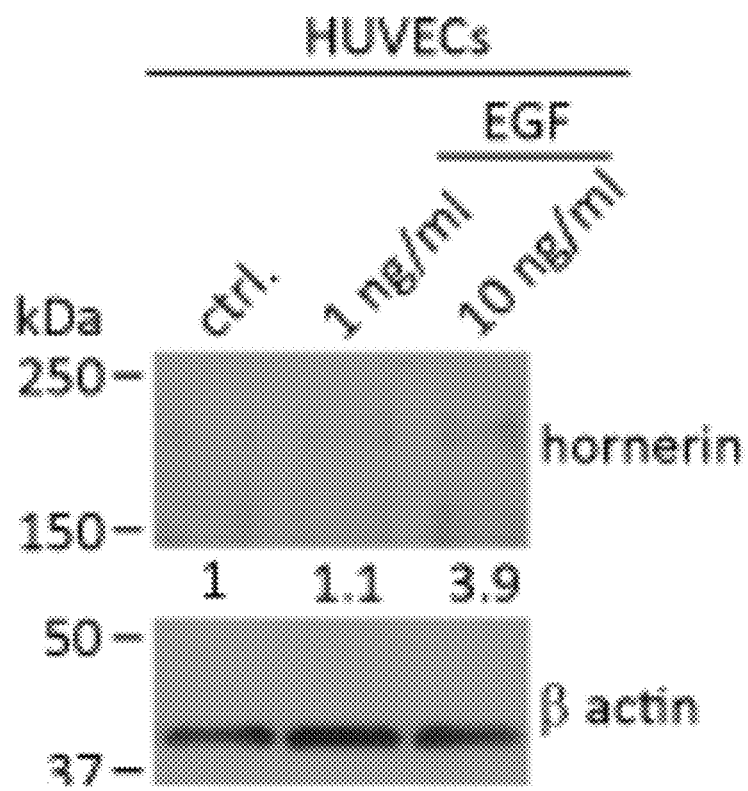
Figure 18D:
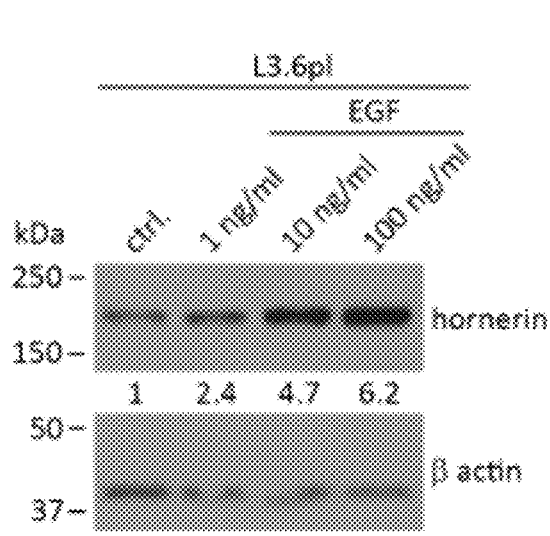
Figure 18E:
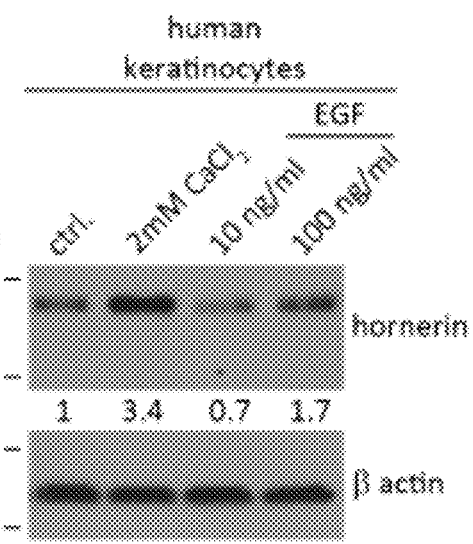

The implication of hornerin in a VEGF-independent signaling cascade that modulates tumor vessel parameters prompts a need to discover the factors present in the L3.6pl secretome that were responsible for hornerin upregulation. Knowledge of the signaling pathways that govern hornerin expression in any biological context, however, remains limited, with calcium indicated as one of the few regulatory molecules in the epidermis (Makino et al., 2001; Henry et al., 2011). Knowledge of expression modulators could direct further studies into the signaling and mechanism of hornerin in tumor angiogenesis. To assess the potential for growth factor-mediated hornerin upregulation, the highest expressed non-VEGF growth factors in the TCM were determined and HUVECs treated with these factors at published B-max concentrations (FIGS. 18A and 18B) were investigated. The results disclosed herein suggested that interleukin 12 (IL-12) and basic FGF (bFGF) might stimulate hornerin expression. It is also established that the L3.6pl cell line produces relatively high levels of epidermal growth factor (EGF) and that in tumor models signaling through the EGF receptor potentiates endothelial cell survival (Baker et al., 2002). It was also observed that hornerin expression increased in HUVECs in response to EGF stimulation, suggesting that one potential mechanism of elevated hornerin in the tumor endothelium was due to tumor cell-derived EGF. However, these results remain to be explored in the tumor setting (FIG. 18C). Interestingly, it appeared that the response to EGF stimulation might be wide ranging, as a concentration-dependent increase in expression to EGF treatment in L3.6pl cells and a more modest response in keratinocytes (FIGS. 18D and 18E) were both observed. Elucidation of the factors, those that regulate hornerin and others that function downstream of hornerin, could have substantial clinical relevance by opening additional avenues of therapeutic intervention targeting the tumor vasculature.

While the present disclosure did reveal a critical role for endothelial cell-hornerin in regulating vessel parameters that are characteristic of the tumor vasculature, the function of hornerin in other cell types in the tumor microenvironment can also be investigated. Future work utilizing conditional knockdown models of hornerin in different cell lineages could provide additional clarity. Preliminary evidence presented in this study suggests that hornerin knockdown does not alter accumulation of leukocytes in the tumor microenvironment. It should not be overlooked that the current understanding attached to hornerin expression, regulation, and function has developed on a foundation laid by other closely related S100 fused-type protein family members: however, very little experimental data exist to validate these assumptions. The fact that hornerin was expressed and functional in the novel biological context revealed herein suggested that much remains to be learned about hornerin at the fundamental level.

REFERENCES

All references listed below, as well as all references cited in the instant disclosure, including but not limited to all patents, patent applications and publications thereof, scientific journal articles, and database entries (e.g., GENBANK® biosequence database entries and all annotations available therein) are incorporated herein by reference in their entireties to the extent that they supplement, explain, provide a background for, or teach methodology, techniques, and/or compositions employed herein.

Alexay et al. The PCT International Society of Optical Engineering 2705/63 (1996).
Al-Lazikani et al. Nat. Biotechnol. 30, 679-692 (2012).
Allen et al. Clin. Cancer Res. 17, 5299-5310 (2011).
Amemiya et al. (1988) Topics Curr Chem 147:121-144
Baker et al. Am. J. Pathol. 161, 929-938 (2002).
Barnes et al. Pharmaceutics 4, 442-478 (2012).
Baselga et al. N. Engl. J. Med. 366, 109-119 (2012).
Batchelor et al. Proc. Natl Acad. Sci. USA 110, 19059-19064 (2013).
Bauminger & Wilchek. Meth Enzymol 70:151-159 (1980).
Bergers & Hanahan. Nat. Rev. Cancer 8, 592-603 (2008).
Biswal et al. Technol. Cancer Res. Treat. 10, 417-429 (2011).
Blaskovich et al. Cancer Res 63:1270-1279 (2003).
Cameron et al. Bioorg Med Chem Lett 19:2075-2078 (2009).
Carmeliet & Jain. Nat. Rev. Drug Discov. 10, 417-427 (2011).
Casanovas et al. Cancer Cell 8, 299-309 (2005).
Cheng. Hum Gene Ther 7:275-282 (1996).
Christian et al. Radiology 232, 677-684 (2004).
Conconi et al. Peptides 25, 2179-2185 (2004).
David et al. Biochemistry 13:1014 (1974).
de Lussanet et al. NMR Biomed. 20, 717-725 (2007).
DeCosta Byfield et al. Mol Pharmacol 65:744-752 (2004).
Donato. Int. J. Biochem. Cell Biol. 33, 637-668 (2001).
Donzella et al. Nat Med 4:72-77 (1998).
Emanueli et al. Arterioscler Thromb Vasc Biol 24:2082-2087 (2004).
Emblem et al. Nat. Med. 19, 1178-1183 (2013).
European Patent No. 0 439 095).
Fleming et al. BMC Cancer 12, 266 (2012).
Fong et al. Cancer Res 59:99-106 (1999).
Gaustad et al. Neoplasia 10, 354-362 (2008).
GENBANK® Accession Nos. NC_000001.11; NC_000069.6; NM_001009931.2; NM_133698.2; NP_598459.2; NP_001009931.1.
Goldman et al. Cancer Res 57:1447-1451 (1997).
Goldman et al. (1997) Cancer Res 57:1447-1451
Gupta et al. J. Clin. Oncol. 21, 106-112 (2003).
Hallahan et al. Am J Clin Oncol 24:473-480 (2001a).
Hallahan et al. J Control Release 74:183-191 (2001b).
Hamzah et al. Nature 453, 410-414 (2008).
Hanahan & Weinberg. Cell 100, 57-70 (2000).
Hanahan & Weinberg. Cell 144, 646-674 (2011).
Hauschild et al. Br. J. Dermatol. 140, 1065-1071 (1999).
Henry et al. FASEB J. 25, 1567-1576 (2011).
Hunter et al. Nature 144:945 (1962).
Igarashi et al. Proc. Natl Acad. Sci. USA 100, 10664-10669 (2003).
Johnston et al. J. Clin. Oncol. 27, 5538-5546 (2009).
Katada et al. J. Proteomics 75, 1803-1815 (2012).
Kaufman et al. J. Clin. Oncol. 27, 5529-5537 (2009).
Kayakabe et al. Rheumatology 51, 1571-1579 (2012).
Kelly et al. Neoplasia 8, 1011-1018 (2006).
Kelly et al. PLoS Med. 5, e85 (2008).
Kiessling et al. Neoplasia 6, 213-223 (2004).
Kindler et al. Lancet Oncol. 12, 256-262 (2011).
Kizawa et al. Biochimie 93, 2038-2047 (2011).
Kumar et al. J. Cell Biol. 211, 1057-1075 (2015).
Kypriotou et al. Exp. Dermatol. 21, 643-649 (2012).
Lang et al. Lancet Oncol. 14, 125-133 (2013).
Leclerc et al. Biochim. Biophys. Acta 1793, 993-1007 (2009).
Li et al. J. Immunol. 170, 3369-3376 (2003).
Littlefield et al. (2008) Inorg Chem 47:2798-2804.
Makino et al. J. Biol. Chem. 276, 47445-47452 (2001).
Makino et al. J. Histochem. Cytochem. 51, 485-492 (2003).
Manome et al. Cancer Res 54:5408-5413 (1994).
Marenholz et al. Biochem. Biophys. Res. Commun. 322, 1111-1122 (2004).
McCormack et al. Biomed. Opt. Express 5, 2247-2261 (2014).
Muller & Scherle Nature Rev Can 6:613-625 (2006).
Nabel. Vectors for Gene Therapy. In *Current Protocols in Human Genetics*, John Wiley & Sons, New York, New York, USA (1997).
Nakamura et al. Cancer Res. 66, 9134-9142 (2006).
Neri et al. Nat Biotechnol 15:1271-1275 (1997).
Nielsen et al. Pharmaceutics 4, 563-589 (2012).
Ning et al. Opt. Lett. 40, 910-913 (2015a).
Ning et al. Sci. Rep. 5, 18775 (2015b).
Nosov et al. J. Clin. Oncol. 30, 1678-1685 (2012).
Nygren J Histochem Cytochem 30:407 (1982).
O'Connor et al. Br. J. Cancer 96, 189-195 (2007).
Pain et al. J Immunol Meth 40:219 (1981).
Park et al. Adv Pharmacol 40:399-435 (1997).
Pasqualini et al. Nat Biotechnol 15:542-546 (1997).
Pawar et al. Cancer Biol. Ther. 12, 510-522 (2011).
PCT International Patent Application Publication No. WO 2016/205397.
Rachow et al. PLoS ONE 8, e55116 (2013).
Reynolds et al. PLoS ONE 6, e22471 (2011).

Rothenfusser et al. Human Immunology 63:1111-1119 (2002).
Rugo et al. J Clin Oncol 23:5474-5483 (2005).
Saltzman & Fung Adv Drug Deliv Rev 26:209-230 (1997).
Sawyer et al. Bioorg Med Chem Lett 14:3581-3584 (2004).
Seaman et al. PLoS ONE 6, e20807 (2011).
Senger et al. Science 219, 983-985 (1983).
Sgadari et al. Blood 87, 3877-3882 (1996).
Shin et al. Proc. Natl Acad. Sci. USA 110, 19414-19419 (2013).
Shojaei. Cancer Lett. 320, 130-137 (2012).
Sutoh Yoneyama et al. Eur. J. Cell Biol. 93, 157-169 (2014).
Takada et al. Phytomedicine 17, 1114-1119 (2010).
Takaishi et al. J. Biol. Chem. 280, 4696-4703 (2005).
Tofts et al. J. Magn. Reson. Imaging 10, 223-232 (1999).
Turkbey et al. Diagn. Interv. Radiol. 16, 186-192 (2010).
U.S. Patent Application Publication No. 2018/0360755.
U.S. Pat. Nos. 4,551,482; 5,490,840; 5,510,103; 5,574,172; 5,651,991; 5,688,931; 5,714,166; 5,786,387; 5,855,900; 5,858,410; 5,922,356; 5,922,545; 5,994,392; 6,071,890; 6,106,866; 6,127,339; 8,481,307.
Ueda et al. Cancer Res. 72, 4318-4328 (2012).
Wang & Hu. Science 335, 1458-1462 (2012).
Wang et al. PLoS One 6:e23513 (2011).
Wedam et al. J. Clin. Oncol. 24, 769-777 (2006).
Whipple & Korc. Langenbecks Arch. Surg. 393, 901-910 (2008).
Wu et al. J. Invest. Dermatol. 129, 1446-1458 (2009).
Xie et al. Cell Signal. 25, 2185-2197 (2013).
Yonenaga et al. Oncology 69, 159-166 (2005).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for treating a tumor and/or a metastatic cell derived therefrom and/or for suppressing growth of the tumor and/or the metastatic cell derived therefrom, the method comprising contacting a cell of the tumor and/or the metastatic cell derived therefrom and/or an endothelial cell associated therewith with an effective amount of a hornerin inhibitor to reduce a biological activity of a hornerin gene product expressed in the cell of the tumor, the metastatic cell derived therefrom, and/or the endothelial cell associated therewith, wherein the hornerin inhibitor comprises an siRNA that is designed to hybridize to a hornerin gene product present within the cell of the tumor and/or the metastatic cell derived therefrom and/or the endothelial cell associated therewith, optionally wherein the hornerin gene product is a human hornerin gene product and/or comprises an open reading frame encoding SEQ ID NO: 34, to thereby inhibit a biological activity of the hornerin gene product in the cell of the tumor and/or the metastatic cell derived therefrom and/or the endothelial cell associated therewith, and further wherein the tumor is a tumor of the breast, ovary, colon, or rectum and/or the metastatic cell derived therefrom is a metastatic cell derived from a tumor of the breast, ovary, colon, or rectum, thereby treating the tumor and/or suppressing the growth of the tumor and/or the metastatic cell derived therefrom.

2. The method of claim 1, wherein the effective amount of the hornerin inhibitor is effective to decrease tumor leakiness, increase tumor oxygenation, increase apoptosis of the cell of the tumor and/or the metastatic cell derived therefrom and/or the endothelial cell associated therewith, reduce growth of the tumor, or any combination thereof in order to treat the tumor and/or suppress the growth thereof.

3. The method of claim 1, wherein the cell of the tumor and/or the metastatic cell derived therefrom and/or the endothelial cell associated therewith is present within a subject, optionally a human subject.

4. The method of claim 1, wherein the contacting results from administering an effective amount of an anti-hornerin siRNA into the tumor.

5. The method of claim 1, further comprising contacting the tumor and/or administering to the subject one or more additional anti-tumor treatments.

6. The method of claim 5, wherein the one or more additional anti-tumor treatments are selected from the group consisting of radiotherapy, chemotherapy, immunotherapy, anti-inflammatory therapy, and combinations thereof.

7. The method of claim 5, wherein the one or more additional anti-tumor treatments comprises an anti-VEGF therapy, optionally an anti-VEGFR2 therapy.

8. The method of claim 7, wherein the anti-VEGFR2 therapy comprises use of an anti-VEGFR2 antibody or VEGFR2-binding fragment thereof and/or a small molecule anti-VEGFR2 inhibitor.

9. The method of claim 8, wherein the anti-VEGFR2 antibody or VEGFR2-binding fragment thereof is selected from the group consisting of ramucirumab or a VEGFR2-binding fragment thereof.

10. The method of claim 8, wherein the small molecule anti-VEGFR2 inhibitor is selected from the group consisting of tivozanib (1-[2-chloro-4-(6,7-dimethoxyquinolin-4-yl)oxyphenyl]-3-(5-methyl-1,2-oxazol-3-yl)urea), axitinib (N-M ethyl-2-[[3-[(E)-2-pyridin-2-ylethenyl]-1H-indazol-6-yl]sulfanyl]benzamide), lenvatinib (4-[3-Chloro-4-(cyclopropylcarbamoylamino)phenoxy]-7-methoxy-quinoline-6-carboxamide), pazopanib (5-({4-[(2,3-Dimethyl-2H-indazol-6-yl)methylamino]pyrimidin-2-yl}amino)-2-methylbenzenesulfonamide), regorafenib (4-[4-({[4-Chloro-3-(trifluoromethyl)phenyl]carbamoyl}amino)-3-fluorophenoxy]-N-methylpyridine-2-carboxamide hydrate), sorafenib (4-[4-({[4-chloro-3-(trifluoromethyl)phenyl]carbamoylamino]phenoxy]-N-methyl-pyridine-2-carboxamide), sunitinib (N-(2-Diethylaminoethyl)-5-[(Z)-(5-fluoro-2-oxo-1H-indol-3-ylidene)methyl]-2,4-dimethyl-1H-pyrrole-3-carboxamide), vandetanib (N-(4-bromo-2-fluorophenyl)-6-methoxy-7-[(1-methylpiperidin-4-yl)methoxy]quinazolin-4-amine), pharmaceutically acceptable salts thereof, and combinations thereof.

11. The method of claim 7, wherein the anti-VEGF therapy comprises use of an anti-VEGF antibody or a VEGF-binding fragment thereof.

12. The method of claim 7, wherein the anti-VEGF antibody or VEGF-binding fragment thereof is selected from the group consisting of bevacizumab and ranibizumab.

* * * * *